(12) United States Patent
Leonard et al.

(10) Patent No.: US 9,221,804 B2
(45) Date of Patent: Dec. 29, 2015

(54) SECONDARY ALCOHOL QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Anne Fourie, San Diego, CA (US); Xiaohua Xue, San Diego, CA (US); Maxwell D. Cummings, Ambler, PA (US)

(73) Assignee: JANSSEN PHARMACEUTICA NV (BE)

( * ) Notice: Subject to any disclaimer, the term of this patent is extended or adjusted under 35 U.S.C. 154(b) by 0 days.

(21) Appl. No.: 14/053,906

(22) Filed: Oct. 15, 2013

(65) Prior Publication Data
US 2015/0105372 A1 Apr. 16, 2015

(51) Int. Cl.
| | |
|---|---|
| *A61K 31/47* | (2006.01) |
| *C07D 215/227* | (2006.01) |
| *C07D 413/06* | (2006.01) |
| *A61K 31/4709* | (2006.01) |
| *A61K 45/06* | (2006.01) |
| *C07D 401/06* | (2006.01) |
| *C07D 401/14* | (2006.01) |

(52) U.S. Cl.
CPC .............. *C07D 413/06* (2013.01); *A61K 31/47* (2013.01); *A61K 31/4709* (2013.01); *A61K 45/06* (2013.01); *C07D 215/227* (2013.01); *C07D 401/06* (2013.01); *C07D 401/14* (2013.01)

(58) Field of Classification Search
CPC ... A61K 31/47; A61K 31/4709; A61K 45/06; C07D 215/227; C07D 401/06; C07D 401/14; C07D 413/06
USPC .......................................... 546/159; 514/312
See application file for complete search history.

(56) References Cited

U.S. PATENT DOCUMENTS

| | | | |
|---|---|---|---|
| 3,472,859 A | 10/1969 | Lesher | |
| 4,656,283 A | 4/1987 | Doehner, Jr. | |
| 4,710,507 A | 12/1987 | Campbell et al. | |
| 4,910,327 A | 3/1990 | Doehner, Jr. | |
| 4,927,926 A | 5/1990 | Corominas et al. | |
| 5,409,930 A | 4/1995 | Spada et al. | |
| 5,780,634 A | 7/1998 | Inoue et al. | |
| 6,248,739 B1 | 6/2001 | Turner et al. | |
| 6,451,812 B1 * | 9/2002 | End et al. | 514/312 |
| 6,624,159 B2 | 9/2003 | Anderson et al. | |
| 6,686,356 B2 | 2/2004 | Strohbach et al. | |
| 6,743,805 B2 * | 6/2004 | End et al. | 514/312 |
| 7,053,105 B2 | 5/2006 | Angibaud et al. | |
| 7,652,014 B2 | 1/2010 | Mabire et al. | |
| 7,902,225 B2 | 3/2011 | Guillemont et al. | |
| 8,017,606 B2 | 9/2011 | Andries et al. | |
| 8,389,739 B1 | 3/2013 | Thacher et al. | |
| 2003/0166675 A1 | 9/2003 | Yang | |
| 2005/0131014 A1 | 6/2005 | Collini et al. | |
| 2007/0072844 A1 | 3/2007 | Jones et al. | |
| 2008/0188521 A1 | 8/2008 | Grimm et al. | |

(Continued)

FOREIGN PATENT DOCUMENTS

| | | |
|---|---|---|
| CN | 101143845 | 3/2008 |
| CN | 101899011 | 12/2010 |

(Continued)

OTHER PUBLICATIONS

Codarri, Nature Immunology, vol. 12(6), Jun. 2011, p. 560-568.*
U.S. Appl. No. 14/053,682.
U.S. Appl. No. 14/053,736.
U.S. Appl. No. 14/053,773.
U.S. Appl. No. 14/053,797.
U.S. Appl. No. 14/053,653.
U.S. Appl. No. 14/053,707.

(Continued)

*Primary Examiner* — D M Seaman
(74) *Attorney, Agent, or Firm* — Yuriy P. Stercho

(57) ABSTRACT

The present invention comprises compounds of Formula I.

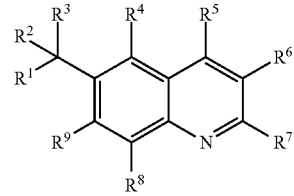

Formula I wherein:
$R^1$, $R^2$, $R^3$, $R^4$, $R^5$, $R^6$, $R^7$, $R^8$, and $R^9$ are defined in the specification.
The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

23 Claims, No Drawings

(56) References Cited

U.S. PATENT DOCUMENTS

| | | |
|---|---|---|
| 2009/0197859 A1 | 8/2009 | Collantes et al. |
| 2009/0286829 A1 | 11/2009 | Heidelbaugh et al. |
| 2010/0311760 A1 | 12/2010 | de Vicente Fidalgo et al. |
| 2011/0124870 A1 | 5/2011 | Guillemont et al. |
| 2012/0322837 A1 | 12/2012 | Maeba et al. |

FOREIGN PATENT DOCUMENTS

| | | | |
|---|---|---|---|
| EP | | 371564 A2 | 6/1990 |
| EP | | 709377 A1 | 5/1996 |
| EP | | 1106612 A1 | 6/2001 |
| EP | | 2368886 A1 | 9/2011 |
| GB | | 2095668 A | 10/1982 |
| JP | | 48026772 | 4/1973 |
| JP | | 2000169451 A | 6/2000 |
| WO | WO | 9718208 A1 | 5/1997 |
| WO | WO | 9721701 A1 | 6/1997 |
| WO | WO | 9744339 A1 | 11/1997 |
| WO | WO | 9855124 A1 | 12/1998 |
| WO | WO | 9932450 A1 | 7/1999 |
| WO | WO | 9950660 A1 | 10/1999 |
| WO | WO | 0001386 A1 | 1/2000 |
| WO | WO | 0001411 A1 | 1/2000 |
| WO | WO | 0001714 A1 | 1/2000 |
| WO | WO | 0039082 A2 | 7/2000 |
| WO | WO | 0040561 A1 | 7/2000 |
| WO | WO | 0040563 A1 | 7/2000 |
| WO | WO | 0047574 A1 | 8/2000 |
| WO | WO | 0156552 A2 | 8/2001 |
| WO | WO | 0162234 A2 | 8/2001 |
| WO | WO | 0164194 A2 | 9/2001 |
| WO | WO | 0164195 A2 | 9/2001 |
| WO | WO | 0164196 A2 | 9/2001 |
| WO | WO | 0164197 A2 | 9/2001 |
| WO | WO | 0164198 A2 | 9/2001 |
| WO | WO | 0164199 A2 | 9/2001 |
| WO | WO | 0164217 A2 | 9/2001 |
| WO | WO | 0164218 A2 | 9/2001 |
| WO | WO | 0164226 A2 | 9/2001 |
| WO | WO | 0164246 A2 | 9/2001 |
| WO | WO | 0164252 A2 | 9/2001 |
| WO | WO | 0202558 A1 | 1/2002 |
| WO | WO | 0204445 A1 | 1/2002 |
| WO | WO | 0204462 A1 | 1/2002 |
| WO | WO | 0224682 A1 | 3/2002 |
| WO | WO | 0224686 A2 | 3/2002 |
| WO | WO | 0224687 A1 | 3/2002 |
| WO | WO | 0228837 A1 | 4/2002 |
| WO | WO | 0243733 A1 | 6/2002 |
| WO | WO | 02051835 A1 | 7/2002 |
| WO | WO | 02064142 A1 | 8/2002 |
| WO | WO | 02070487 A1 | 9/2002 |
| WO | WO | 02085364 A1 | 10/2002 |
| WO | WO | 03/000705 | 1/2003 |
| WO | WO | 03053971 A1 | 7/2003 |
| WO | WO | 03053972 A1 | 7/2003 |
| WO | WO | 03082350 A2 | 10/2003 |
| WO | WO | 2004019932 A1 | 3/2004 |
| WO | WO | 2004024693 A1 | 3/2004 |
| WO | WO | 2004037792 A2 | 5/2004 |
| WO | WO | 2005054201 A1 | 6/2005 |
| WO | WO | 2005054210 A1 | 6/2005 |
| WO | WO | 2005058843 A1 | 6/2005 |
| WO | WO | 2005070430 A1 | 8/2005 |
| WO | WO | 2005075428 A1 | 8/2005 |
| WO | WO | 2006003146 A1 | 1/2006 |
| WO | WO | 2006013896 A1 | 2/2006 |
| WO | | 2006025683 | 3/2006 |
| WO | WO | 2006052718 A2 | 5/2006 |
| WO | WO | 2007014940 A2 | 2/2007 |
| WO | WO | 2007014941 A2 | 2/2007 |
| WO | WO | 2007088978 A1 | 8/2007 |
| WO | WO | 2008051805 A2 | 5/2008 |
| WO | WO | 2008068267 A1 | 6/2008 |
| WO | WO | 2008098104 A8 | 8/2008 |
| WO | WO | 2008112525 A2 | 9/2008 |
| WO | WO | 2008144767 A1 | 11/2008 |
| WO | WO | 2009091735 A1 | 7/2009 |
| WO | WO | 2009140138 A1 | 11/2009 |
| WO | WO | 2010068296 A1 | 6/2010 |
| WO | WO | 2010127208 A1 | 11/2010 |
| WO | WO | 2010151740 A4 | 12/2010 |
| WO | WO | 2011020861 A1 | 2/2011 |
| WO | WO | 2011112264 A1 | 9/2011 |
| WO | WO | 2011130707 A2 | 10/2011 |
| WO | WO | 2012064744 A2 | 5/2012 |
| WO | WO | 2012116137 A2 | 8/2012 |
| WO | WO | 2012158784 A2 | 11/2012 |
| WO | WO | 2013061074 A1 | 5/2013 |
| WO | WO | 2013064231 A1 | 5/2013 |
| WO | WO | 2013079223 A1 | 6/2013 |

OTHER PUBLICATIONS

International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.
Bink A, (A fungicidal piperazine-1-carboxamidine induces mitochondrial fission-dependent apoptosis in yeast), FEMS Yeast Research (2010), 10(7), 812-818.
Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.
Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.
Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.
Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.
Aghera V, (Synthesis, spectral and microbial studies of some novel quinoline derivatives via Vilsmeier-Haack reagent) Journal; (online computer file) URL: http://www.arkat-usa.org/get-file/25177/.
Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.
Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.
Hirao I, (Studies on the synthesis of quinoline compounds. I. Syntheses of 3,3'-dicarboxy-1,1'-diethyl-4,4'-dioxo-1,1',4,4'-tetrahydrobiquinolines), Memoirs of the Kyushu Institute of Technology, Engineering (1984), 14, 13-16.
Abdul-Ahad P, (Trends in dehydrogenase inhibitory potencies of some quinolones, using quantum chemical indices), European Journal of Medicinal Chemistry (1982), 17(4), 301-6.
Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.
Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.
Dong C, (Diversification of T-helper-cell lineages: finding the family root of IL-17-producing cells), Nat Rev Immunol (2006), 6(4), 329-333.
McKenzie B, (Understanding the IL-23-IL-17 immune pathway), Trends Immunol (2006), 27(1), 17-23.

(56) References Cited

OTHER PUBLICATIONS

Ivanov II B, (The orphan nuclear receptor RORgammat directs the differentiation program of proinflammatory IL-17+ T helper cells), Cell (2006), 126(6), 1121-33.
Cua, D (Interleukin-23 rather than interleukin-12 is the critical cytokine for autoimmune inflammation of the brain), Nature (2003), 421(6924), 744-748.
Langrish C, (IL-23 drives a pathogenic T cell population that induces autoimmune inflammation), J Exp Med (2005), 201(2), 233-240.
Tonel G, (Cutting edge: A critical functional role for IL-23 in psoriasis), J Immunol (2010), 185(10), 5688-5691.
Barczyk A, (Interleukin-17 in sputum correlates with airway hyperresponsiveness to methacholine), Respir Med (2003), 97(6), 726-733.
Lock C, (Gene-microarray analysis of multiple sclerosis lesions yields new targets validated in autoimmune encephalomyelitis) Nat Med (2002), 8(5), 500-8.
Papp K, (Brodalumab, an anti-interleukin-17-receptor antibody for psoriasis), N Engl J Med (2012), 366(13), 1181-1189.
Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4-Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxy-methyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
U.S. Appl. No. 14/513,426.
U.S. Appl. No. 14/513,455.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12//053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated Sep. 12, 2004.
U.S. Appl. No. 14/053,906, Notice of Allowance dated Mar. 23, 2015.
Dorwald F. A. "Slide Reactions in Organic Synthesis", 2005, Wiley: VCH, Weinheim pg. IX of Preface p. 1-15.
Venkatesh, et al. "Role of the Development Scientist in Compound Lead Selection and Optimization", J. Pharm. Sci. vol. 89, No. 2, pp. 145-154 2000.
Hiro, STN Document No. 102: 149081 Abstract of Memoirs of the Kyushu Institute of Technology, Engineering (1984), vol. 14, pp. 13-16.
STN Search Report Mar. 12, 2015, RN 1347913-41-0.

\* cited by examiner

SECONDARY ALCOHOL QUINOLINYL MODULATORS OF RORγT

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4$^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor ROR-gamma t directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8.; Langrish, C. L., Y. Chen, et al. (2005). "IL-23 drives a pathogenic T cell population that induces autoimmune inflammation." J Exp Med 201(2): 233-40; Yen. D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk. N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

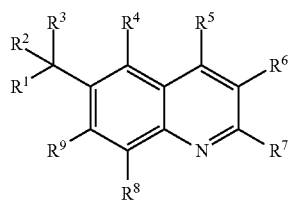

Formula I $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said piperidinyl, pyridyl, pyridyl N-oxide, pyrimidinyl, pyridazyl, pyrazinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl (including $C(O)CH_3$), $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{1-4}$alkyl (including $C_{(1-2)}$alkyl), $CF_3$, $CH_2CF_3$, Cl, F, —CN, $OC_{(1-4)}$alkyl (including $OCH_3$), $N(C_{(1-4)}$alkyl$)_2$ (including $N(CH_3)_2$), —$(CH_2)_3$ $OCH_3$, $SC_{(1-4)}$alkyl (including $SCH_3$), OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl (including $CH_3$), $SCH_3$, $OC_{(1-2)}$alkyl (including $OCH_3$), $CF_3$, —CN, and F; and wherein said triazolyl, oxazolyl, isoxazolyl, pyrrolyl, and thiazolyl are optionally substituted with two substituents independently selected from the group consisting of $SO_2CH_3$, $SO_2NH_2$, $C(O)NH_2$, —CN, $OC_{(1-2)}$alkyl, $(CH_2)_{(2-3)}$ $OCH_3$, $SCH_3$, $CF_3$, F, Cl, and $C_{(1-2)}$alkyl (including $CH_3$); and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)$ $NHSO_2CH_3$, $SO_2CH_3$, $SO_2NH_2$, $C(O)NH_2$, —CN, $OC_{(1-4)}$alkyl, $(CH_2)_{(2-3)}OCH_3$, $SC_{(1-4)}$alkyl, $CF_3$, F, Cl, and $C_{(1-4)}$alkyl; and wherein said azetidinyl is optionally substituted with $CH_3$, $C(O)NH_2$, $CO_2C(CH_3)_3$, $SO_2CH_3$, or $C(O)CH_3$;

$R^2$ is H;
$R^3$ OH, $OCH_3$, or $NH_2$;
$R^4$ is H, or F;
$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, 4-hydroxy-piperidinyl, azetidin-1-yl, or fur-2-yl;
$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, $C_{(1-4)}$alkyl (including $CH_3$), $OC_{(1-4)}$alkyl, C(O) $C_{(1-4)}$alkyl, $CO_2H$, $CO_2C_{(1-4)}$alkyl, $NH_2$, $NHC_{(1-2)}$ alkyl, $N(C_{(1-2)}$alkyl$)_2$, $SO_2NH_2$, $SONH_2$, $SO_2NHC_{(1-2)}$ alkyl, $SON(CH_3)_2$, $SO_2N(C_{(1-2)}$alkyl$)_2$, $SCH_3$, $OCH_2CF_3$, $SO_2CH_3$, $CF_3$, Cl, F, OH, and $OCF_3$; or $R^6$ is —O-phenyl, —NHphenyl, —N($C_{(1-3)}$alkyl)phenyl, —N($CO_2C(CH_3)_3$)phenyl, N(COCH$_3$)phenyl, —O-pyridyl, —NHpyridyl, —N($C_{(1-3)}$alkyl)pyridyl, N($CO_2C$ $(CH_3)_3$)pyridyl, N(COCH$_3$)pyridyl, —O-pyrimidinyl, —NHpyrimidinyl, —N($C_{(1-3)}$alkyl)pyrimidinyl, N($CO_2C(CH_3)_3$)pyrimidinyl, N(COCH$_3$)pyrimidinyl, —O-pyridazyl, —NHpyridazyl, —N($C_{(1-3)}$alkyl)pyridazyl, N($CO_2C(CH_3)_3$)pyridazyl, N(COCH$_3$)pyridazyl, —O-pyrazinyl, —NHpyrazinyl, —N($C_{(1-3)}$ alkyl)pyrazinyl, N($CO_2C(CH_3)_3$)pyrazinyl, or N(COCH$_3$)pyrazinyl; wherein said pyrimidinyl, pyridazyl, or pyrazinyl portions thereof are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl portions thereof or said pyridyl portions thereof are optionally substituted with up to two substituents independently selected from the group consisting of $OCF_3$, $OCHF_2$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$ alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$ alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally substituted with $CH_3$; or $R^6$ is —$CH_2R^{6'}$, wherein $R^{6'}$ is pyridyl, phenyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said pyridyl or phenyl is optionally substituted with up to two substituents independently selected from the group consisting of $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$ cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, CON $(CH_3)_2$, Cl, F, —CN, $CO_2H$, OH, $CH_2OH$, NHC $OC_{(1-2)}$alkyl, $COC_{(1-2)}$alkyl, $SCH_3$, $CO_2C_{(1-4)}$alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally substituted with $CH_3$;
$R^7$ is H, Cl, —CN, $C_{(1-4)}$alkyl, $OC_{(1-4)}$alkylCF$_3$, $OCF_3$, $OCHF_2$, $OCH_2CH_2OC_{(1-4)}$alkyl, $CF_3$, $SCH_3$, $C_{(1-4)}$ alkylNA$^1$A$^2$ (including $CH_2NA^1A^2$), $CH_2OC_{(2-3)}$ alkylNA$^1$A$^2$, NA$^1$A$^2$, $C(O)NA^1A^2$, $CH_2NHC_{(2-3)}$ alkylNA$^1$A$^2$, $CH_2N(CH_3)C_{(2-3)}$alkylNA$^1$A$^2$, $NHC_{(2-3)}$ alkylNA$^1$A$^2$, $N(CH_3)C_{(2-4)}$alkylNA$^1$A$^2$, $OC_{(2-4)}$ alkylNA$^1$A$^2$, $OC_{(1-4)}$alkyl, $OCH_2$-(1-methyl)-imidazol- 2-yl, phenyl, thiophenyl, furyl, pyrazolyl, imidazolyl, pyridyl, pyridazyl, pyrazinyl, pyrimidinyl, indazolyl, phenyl, or

[structure: styryl group]

wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, $CH_3$, $CF_3$, and $OCH_3$;

$A^1$ is H or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl;

or $A^1$ and $A^2$ may be taken together with their attached nitrogen to form a ring selected from the group consisting of:

[structures of rings]

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$), $CF_3$, $NH_2$, $NHCH_3$, —CN, or F;

$R^9$ is H, or F;

and pharmaceutically acceptable salts thereof;

provided that azetidin-3-yl(4-chloro-2-methoxy-3-(4-(trifluoromethyl)benzyl)quinolin-6-yl)methanol, and tert-butyl 4-((4-chloro-2-methoxy-3-(4-(trifluoromethyl)benzyl)quinolin-6-yl)(hydroxy)methyl)piperidine-1-carboxylate are excluded from the embodiment.

DETAILED DESCRIPTION OF THE INVENTION

The present invention comprises compounds of Formula I.

Formula I

[structure of Formula I: quinoline with substituents $R^1$, $R^2$, $R^3$, $R^4$, $R^5$, $R^6$, $R^7$, $R^8$, $R^9$]

$R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said piperidinyl, pyridyl, pyridyl N-oxide, pyrimidinyl, pyridazyl, pyrazinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$ alkyl (including C(O)CH₃), C(O)NH₂, C(O)NHC₍₁₋₂₎alkyl, C(O)N(C₍₁₋₂₎alkyl)₂, NHC(O)C₍₁₋₄₎alkyl, NHSO₂C₍₁₋₄₎alkyl, C₍₁₋₄₎alkyl (including C₍₁₋₂₎alkyl), CF₃, CH₂CF₃, Cl, F, —CN, OC₍₁₋₄₎alkyl (including OCH₃), N(C₍₁₋₄₎alkyl)₂ (including N(CH₃)₂), —(CH₂)₃OCH₃, SC₍₁₋₄₎alkyl (including SCH₃), OH, CO₂H, CO₂C₍₁₋₄₎alkyl, C(O)CF₃, SO₂CF₃, OCF₃, OCHF₂, SO₂CH₃, SO₂NH₂, SO₂NHC₍₁₋₂₎alkyl, SO₂N(C₍₁₋₂₎alkyl)₂, C(O)NHSO₂CH₃, or OCH₂OCH₃; and optionally substituted with up to two additional substituents independently selected from the group consisting of Cl, C₍₁₋₂₎alkyl (including CH₃), SCH₃, OC₍₁₋₂₎alkyl (including OCH₃), CF₃, —CN, and F; and wherein said triazolyl, oxazolyl, isoxazolyl, pyrrolyl, and thiazolyl are optionally substituted with two substituents independently selected from the group consisting of SO₂CH₃, SO₂NH₂, C(O)NH₂, —CN, OC₍₁₋₂₎alkyl, (CH₂)₍₂₋₃₎OCH₃, SCH₃, CF₃, F, Cl, and C₍₁₋₂₎alkyl (including CH₃); and said thiadiazolyl and oxadiazolyl are optionally substituted with C₍₁₋₂₎alkyl; and said pyridyl, pyridyl-N-oxide, pyrimidinyl, pyridazyl, and pyrazinyl are optionally substituted with up to three additional substituents independently selected from the group consisting of C(O)NHC₍₁₋₂₎alkyl, C(O)N(C₍₁₋₂₎alkyl)₂, NHC(O)C₍₁₋₄₎alkyl, NHSO₂C₍₁₋₄₎alkyl, C(O)CF₃, SO₂CF₃, SO₂NHC₍₁₋₂₎alkyl, SO₂N(C₍₁₋₂₎alkyl)₂, C(O)NHSO₂CH₃, SO₂CH₃, SO₂NH₂, C(O)NH₂, —CN, OC₁₋₄alkyl, (CH₂)₍₂₋₃₎OCH₃, SC₍₁₋₄₎alkyl, CF₃, F, Cl, and C₍₁₋₄₎alkyl; and wherein said azetidinyl is optionally substituted with CH₃, C(O)NH₂, CO₂C(CH₃)₃, SO₂CH₃, or C(O)CH₃;

$R^2$ is H;

$R^3$ OH, OCH₃, or NH₂;

$R^4$ is H, or F;

$R^5$ is H, Cl, —CN, CF₃, SC₍₁₋₄₎alkyl, OC₍₁₋₄₎alkyl, OH, C₍₁₋₄₎alkyl, N(CH₃)OCH₃, NH(C₍₁₋₄₎alkyl), N(C₍₁₋₄₎alkyl)₂, 4-hydroxy-piperidinyl, azetidin-1-yl, or fur-2-yl; provided that $R^5$ may not be H if $R^7$ is also H;

$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, C₍₁₋₄₎alkyl (including CH₃), OC₍₁₋₄₎alkyl, C(O)C₍₁₋₄₎alkyl, CO₂H, CO₂C₍₁₋₄₎alkyl, NH₂, NHC₍₁₋₂₎alkyl, N(C₍₁₋₂₎alkyl)₂, SO₂NH₂, SONH₂, SO₂NHC₍₁₋₂₎alkyl, SON(CH₃)₂, SO₂N(C₍₁₋₂₎alkyl)₂, SCH₃, OCH₂CF₃, SO₂CH₃, CF₃, Cl, F, OH, and OCF₃; or $R^6$ is —O-phenyl, —NHphenyl, —N(C₍₁₋₃₎alkyl)phenyl, —N(CO₂C(CH₃)₃)phenyl, N(COCH₃)phenyl, —O-pyridyl, —NHpyridyl, —N(C₍₁₋₃₎alkyl)pyridyl, N(CO₂C(CH₃)₃)pyridyl, N(COCH₃)pyridyl, —O-pyrimidinyl, —NHpyrimidinyl, —N(C₍₁₋₃₎alkyl)pyrimidinyl, N(CO₂C(CH₃)₃)pyrimidinyl, N(COCH₃)pyrimidinyl, —O-pyridazyl, —NHpyridazyl, —N(C₍₁₋₃₎alkyl)pyridazyl, N(CO₂C(CH₃)₃)pyridazyl, N(COCH₃)pyridazyl, —O-pyrazinyl, —NHpyrazinyl, —N(C₍₁₋₃₎alkyl)pyrazinyl, N(CO₂C(CH₃)₃)pyrazinyl, or N(COCH₃)pyrazinyl; wherein said pyrimidinyl, pyridazyl, or pyrazinyl portions thereof are optionally substituted with Cl, F, CH₃, SCH₃, OC₍₁₋₄₎alkyl, —CN, CONH₂, SO₂NH₂, or SO₂CH₃; and wherein said phenyl portions thereof or said pyridyl portions thereof are optionally substituted with up to two substituents independently selected from the group consisting of OCF₃, OCHF₂, SO₂C₍₁₋₄₎alkyl, CF₃, CHF₂, pyrazolyl, triazolyl, imidazolyl, tetrazolyl, oxazolyl, thiazolyl, C₍₁₋₄₎alkyl, C₍₃₋₄₎cycloalkyl, OC₍₁₋₄₎alkyl, N(CH₃)₂, SO₂NH₂, SO₂NHCH₃, SO₂N(CH₃)₂, CONH₂, CONHCH₃, CON(CH₃)₂, Cl, F, —CN, CO₂H, OH, CH₂OH, NHCOC₍₁₋₂₎alkyl, COC₍₁₋₂₎alkyl, SCH₃, CO₂C₍₁₋₄₎alkyl, NH₂, NHC₍₁₋₂₎alkyl, and OCH₂CF₃; and wherein said pyrazolyl, triazolyl, imidazolyl, tetrazolyl, oxazolyl, and thiazolyl are optionally substituted with CH₃; or $R^6$ is —CH₂R^{6'}, wherein $R^{6'}$ is pyridyl, phenyl, benzothiophenyl, thiophenyl, pyrimidinyl, pyridazyl, or pyrazinyl; wherein said pyrimidinyl, pyridazyl, or pyrazinyl are optionally substituted with Cl, F, CH₃, SCH₃, OC₍₁₋₄₎alkyl, —CN, CONH₂, SO₂NH₂, or SO₂CH₃; and wherein said pyridyl or phenyl is optionally substituted with up to two substituents independently selected from the group consisting of OCF₃, SO₂C₍₁₋₄₎alkyl, CF₃, CHF₂, pyrazolyl, triazolyl, imidazolyl, tetrazolyl, oxazolyl, thiazolyl, C₍₁₋₄₎alkyl, C₍₃₋₄₎cycloalkyl, OC₍₁₋₄₎alkyl, N(CH₃)₂, SO₂NH₂, SO₂NHCH₃, SO₂N(CH₃)₂, CONH₂, CONHCH₃, CON(CH₃)₂, Cl, F, —CN, CO₂H, OH, CH₂OH, NHCOC₍₁₋₂₎alkyl, COC₍₁₋₂₎alkyl, SCH₃, CO₂C₍₁₋₄₎alkyl, NH₂, NHC₍₁₋₂₎alkyl, and OCH₂CF₃; and wherein said pyrazolyl, triazolyl, imidazolyl, tetrazolyl, oxazolyl, and thiazolyl are optionally substituted with CH₃;

$R^7$ is H, Cl, —CN, C₍₁₋₄₎alkyl, OC₍₁₋₄₎alkylCF₃, OCF₃, OCHF₂, OCH₂CH₂OC₍₁₋₄₎alkyl, CF₃, SCH₃, C₍₁₋₄₎alkylNA¹A² (including CH₂NA¹A²), CH₂OC₍₂₋₃₎alkylNA¹A², NA¹A², C(O)NA¹A², CH₂NHC₍₂₋₃₎alkylNA¹A², CH₂N(CH₃)C₍₂₋₃₎alkylNA¹A², NHC₍₂₋₃₎alkylNA¹A², N(CH₃)C₍₂₋₄₎alkylNA¹A², OC₍₂₋₄₎alkylNA¹A², OC₍₁₋₄₎alkyl, OCH₂-(1-methyl)-imidazol-2-yl, phenyl, thiophenyl, furyl, pyrazol, imidazolyl, pyridyl, pyridazyl, pyrazinyl, pyrimidinyl, indazolyl, phenyl, or

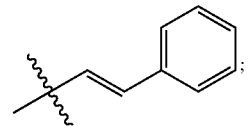 [SMILES: */C=C/c1ccccc1]

wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, CH₃, CF₃, and OCH₃;

$A^1$ is H or C₍₁₋₄₎alkyl;

$A^2$ is H, C₍₁₋₄₎alkyl, C₍₁₋₄₎alkylOC₍₁₋₄₎alkyl, C₍₁₋₄₎alkylOH, C(O)C₍₁₋₄₎alkyl, or OC₍₁₋₄₎alkyl;

or $A^1$ and $A^2$ may be taken together with their attached nitrogen to form a ring selected from the group consisting of:

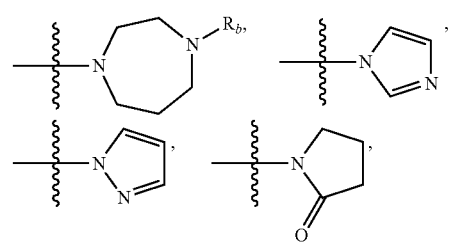

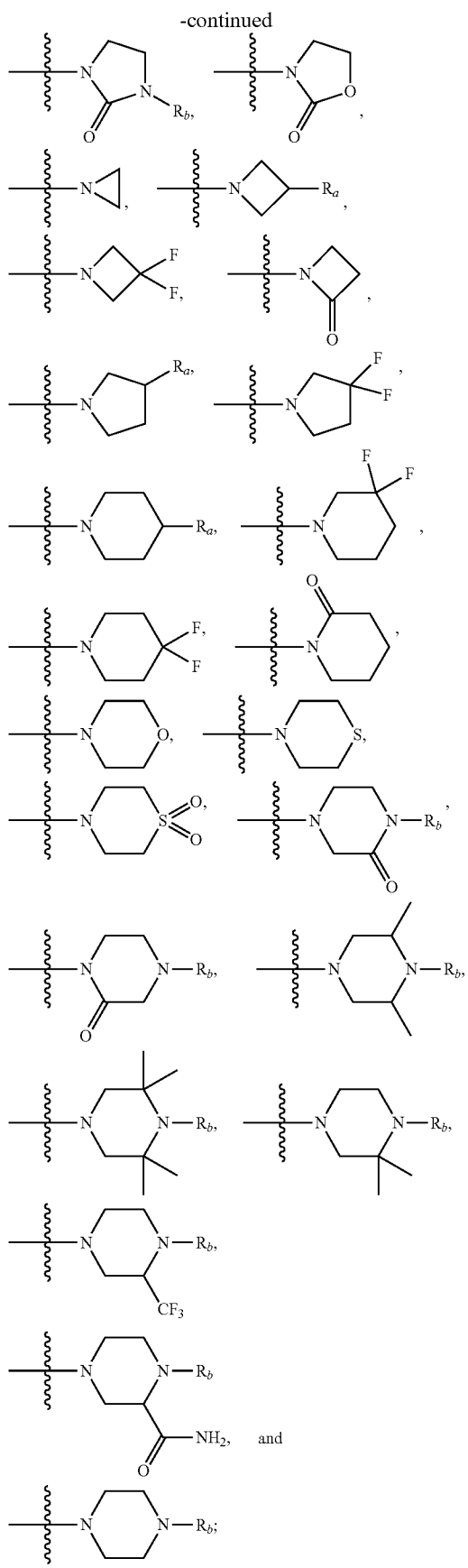

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl (including $CH_3$), $OC_{(1-3)}$alkyl (including $OCH_3$), $CF_3$, $NH_2$, $NHCH_3$, —CN, or F;

$R^9$ is H, or F;

and pharmaceutically acceptable salts thereof;

provided that azetidin-3-yl(4-chloro-2-methoxy-3-(4-(trifluoromethyl)benzyl)quinolin-6-yl)methanol, and tert-butyl 4-((4-chloro-2-methoxy-3-(4-(trifluoromethyl)benzyl) quinolin-6-yl)(hydroxy)methyl)piperidine-1-carboxylate are excluded from the embodiment.

In another embodiment of the invention:

$R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $C(O)CH_3$, $C(O)NH_2$, $C_{(1-4)}$alkyl (including $CH_3$), $CF_3$, Cl, F, —CN, $OCH_3$, $N(CH_3)_2$, —$(CH_2)_3OCH_3$, $SCH_3$, OH, $CO_2H$, $CO_2C_{(1-4)}$alkyl, $SO_2CH_3$, or $OCH_2OCH_3$; and optionally substituted with up to two additional substituents independently selected from the group consisting of Cl, $CH_3$, and $OCH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $SO_2CH_3$, or $C(O)CH_3$;

$R^2$ is H;

$R^3$ is OH, $OCH_3$, or $NH_2$;

$R^4$ is H, or F;

$R^5$ is H, Cl, —CN, $CF_3$, $SCH_3$, $OC_{(1-3)}$alkyl (including $OC_{(1-2)}$alkyl), OH, $C_{(1-4)}$alkyl, $N(CH_3)OCH_3$, $NH(C_{(1-2)}$alkyl) (including $NH(CH_3)$), $N(C_{(1-2)}$alkyl)$_2$, 4-hydroxy-piperidinyl, azetidin-1-yl, or fur-2-yl; provided that $R^5$ may not be H if $R^7$ is also H;

$R^6$ is pyridyl or phenyl, either of which is optionally substituted with Cl, F, $CF_3$, $SO_2CH_3$, —CN, or $OCF_3$; or $R^6$ is —O-phenyl, —NHphenyl, —N($C_{(1-3)}$alkyl)phenyl, —N($CO_2C(CH_3)_3$)phenyl, —O-pyridyl, —NHpyridyl, —N($C_{(1-3)}$alkyl)pyridyl, or —N($CO_2C(CH_3)_3$)pyridyl wherein said phenyl portions thereof or said pyridyl portions thereof are optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN; or $R^6$ is —$CH_2R^{6'}$, wherein $R^{6'}$ is pyridyl, phenyl, benzothiophenyl, or thiophenyl; wherein said pyridyl or phenyl is optionally substituted with $OCF_3$, $SO_2CH_3$, $CF_3$, $CHF_2$, imidazol-1-yl, pyrazol-1-yl, 1,2,4-triazol-1-yl, $CH_3$, $OCH_3$, Cl, F, or —CN;

$R^7$ is H, Cl, —CN, $C_{(1-4)}$alkyl (including $C_{(1-2)}$alkyl), $OCH_2CF_3$, $OCH_2CH_2OCH_3$, $CF_3$, $SCH_3$, $NA^1A^2$, $C(O)NHCH_3$, $N(CH_3)CH_2CH_2NA^1A^2$, $OCH_2CH_2NA^1A^2$, $OC_{(1-3)}$alkyl (including $OC_{(1-2)}$alkyl), $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

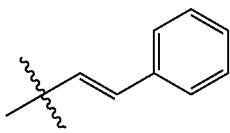 [SMILES: */C=C/c1ccccc1]

wherein said imidazolyl or pyrazolyl can be optionally substituted with a CH$_3$ group;

A$^1$ is H or C$_{(1-4)}$alkyl (including C$_{(1-2)}$alkyl);
A$^2$ is H, C$_{(1-4)}$alkyl (including C$_{(1-2)}$alkyl), C$_{(1-4)}$alkylOC$_{(1-4)}$alkyl (including CH$_2$CH$_2$OCH$_3$), C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

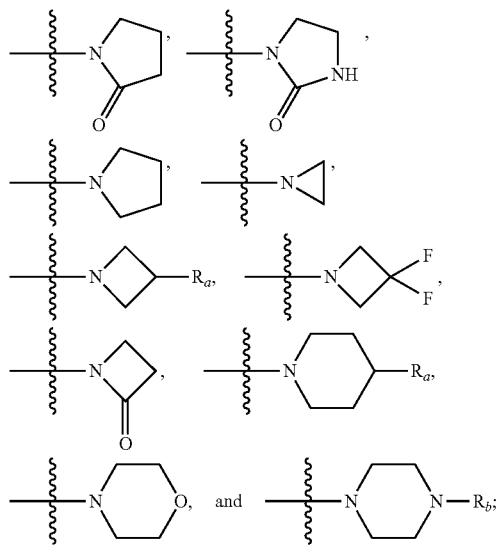

R$_a$ is H, F, OCH$_3$, or OH;
R$_b$ is CH$_3$, or phenyl;
R$^8$ is H, CH$_3$, OCH$_3$, or F;
R$^9$ is H, or F;
and pharmaceutically acceptable salts thereof;
provided that azetidin-3-yl(4-chloro-2-methoxy-3-(4-(trifluoromethyl)benzyl)quinolin-6-yl)methanol, and tert-butyl 4-((4-chloro-2-methoxy-3-(4-(trifluoromethyl)benzyl) quinolin-6-yl)(hydroxy)methyl)piperidine-1-carboxylate are excluded from the embodiment.

In another embodiment of the invention:
R$^1$ is azetidinyl, pyrazolyl, imidazolyl, triazolyl, thiazolyl, pyridyl, pyrimidinyl, piperidinyl, phenyl, isoxazolyl, or oxazolyl; wherein said piperidinyl, pyridyl, imidazolyl, phenyl, and pyrazolyl are optionally substituted with C(O)CH$_3$, C(O)NH$_2$, C$_{(1-2)}$alkyl (including CH$_3$), CF$_3$, Cl, —CN, or OCH$_3$; and optionally substituted with up to two additional CH$_3$ groups; and wherein said triazolyl, oxazolyl, and isoxazolyl, are optionally substituted with one or two CH$_3$ groups; and wherein said azetidinyl is optionally substituted with CO$_2$C(CH$_3$)$_3$;
R$^2$ is H;
R$^3$ is OH;
R$^4$ is H or F;
R$^5$ is H, —CN, CF$_3$, CH$_3$, Cl, OC$_{(1-2)}$alkyl (including OCH$_3$), OH, C$_{(1-4)}$alkyl (including CH$_3$), NH(CH$_3$), N(C$_{(1-2)}$alkyl)$_2$, or 4-hydroxy-piperidinyl;

R$^6$ is phenyl, or pyridyl; wherein said phenyl or said pyridyl is optionally substituted with Cl, OCF$_3$, F, or —CN; or R$^6$ is —O-phenyl, —NHphenyl, —N(C$_{(1-3)}$alkyl)phenyl, or —N(CO$_2$C(CH$_3$)$_3$)phenyl; wherein said phenyl portion thereof is optionally substituted with Cl, F, or —CN; or R$^6$ is —CH$_2$R$^{6'}$, wherein R$^{6'}$ is pyridyl, or phenyl, wherein said phenyl is optionally substituted with pyrazol-1-yl, 1,2,4-triazol-1-yl, OCH$_3$, SO$_2$CH$_3$, Cl, F, CF$_3$, or —CN; and wherein said pyridyl is optionally substituted with CF$_3$;
R$^7$ is Cl, NA$^1$A$^2$, —CN, C$_{(1-2)}$alkyl (including CH$_2$CH$_3$), OC$_{(1-2)}$alkyl (including OCH$_3$), CONHCH$_3$, or CF$_3$,
A$^1$ is C$_{(1-2)}$alkyl;
A$^2$ is C$_{(1-4)}$alkyl, CH$_2$CH$_2$OCH$_3$, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

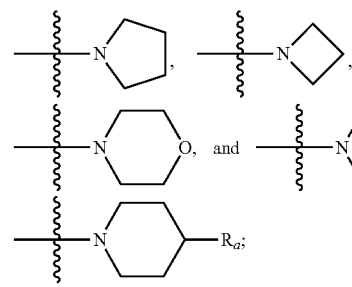

R$_a$ is OCH$_3$, or OH;
R$_b$ is CH$_3$, or phenyl;
R$^8$ is H, OCH$_3$, F, or CH$_3$;
R$^9$ is H, or F;
and pharmaceutically acceptable salts thereof; provided that azetidin-3-yl(4-chloro-2-methoxy-3-(4-(trifluoromethyl) benzyl)quinolin-6-yl)methanol, and tert-butyl 4-((4-chloro-2-methoxy-3-(4-(trifluoromethyl)benzyl)quinolin-6-yl)(hydroxy)methyl)piperidine-1-carboxylate are excluded from the embodiment.

In another embodiment of the invention
R$^1$ is N-Boc-azetidin-3-yl, 1,3,5-trimethyl-pyrazol-4-yl, 1-methyl-imidazol-5-yl, 1,2-dimethyl-imidazol-5-yl, 1-methyl-1,2,3-triazol-5-yl, pyrid-4-yl, 2,6-dimethyl-pyrid-3-yl, N-acetyl-piperidin-4-yl, phenyl, 3,5-dimethyl-isoxazol-4-yl, 3-methyl-isoxazol-5-yl, or 2,4-dimethyl-oxazol-5-yl; wherein said phenyl is optionally substituted with Cl, or CN;
R$^2$ is H;
R$^3$ is OH;
R$^4$ is H;
R$^5$ is H, or Cl;
R$^6$ is phenyl, wherein said phenyl is optionally substituted with Cl; or R$^6$ is —CH$_2$R$^{6'}$, wherein R$^{6'}$ is pyridyl, or phenyl, wherein said phenyl is optionally substituted with pyrazol-1-yl, SO$_2$CH$_3$, F, CF$_3$, or —CN; and wherein said pyridyl is optionally substituted with CF$_3$;
R$^7$ is Cl, azetidin-1-yl, CH$_2$CH$_3$, or OCH$_3$;
R$^8$ is H, or CH$_3$;
R$^9$ is H;
and pharmaceutically acceptable salts thereof.

Another embodiment of the invention is a compound selected from the group consisting of:

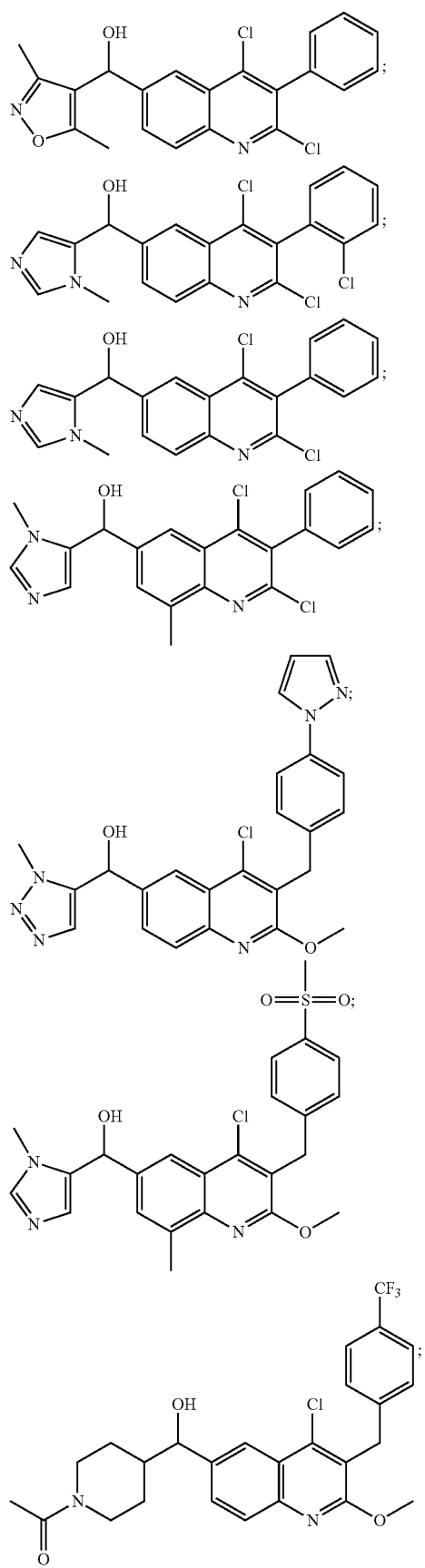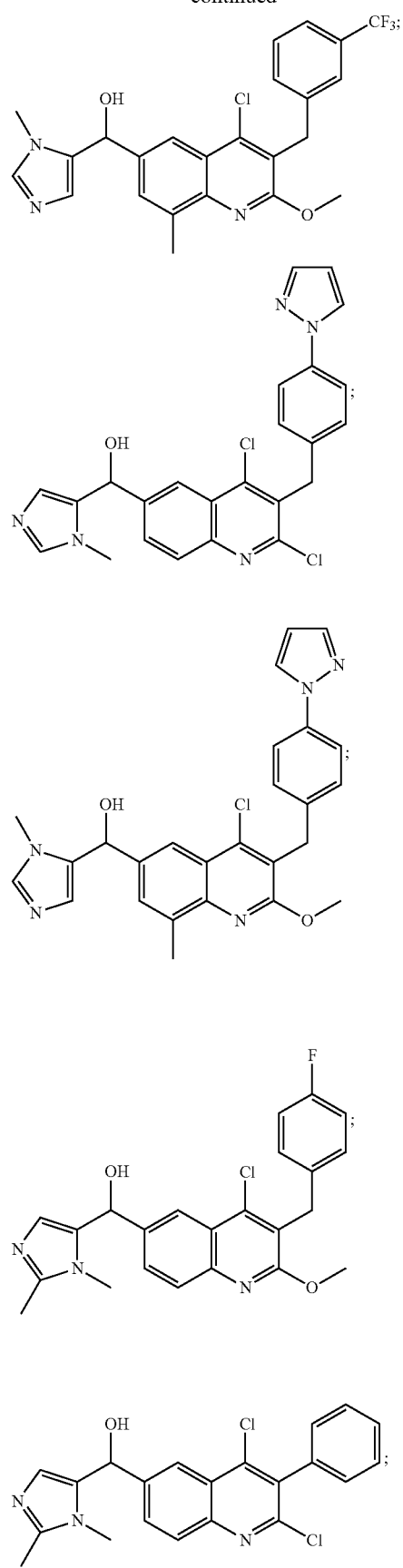

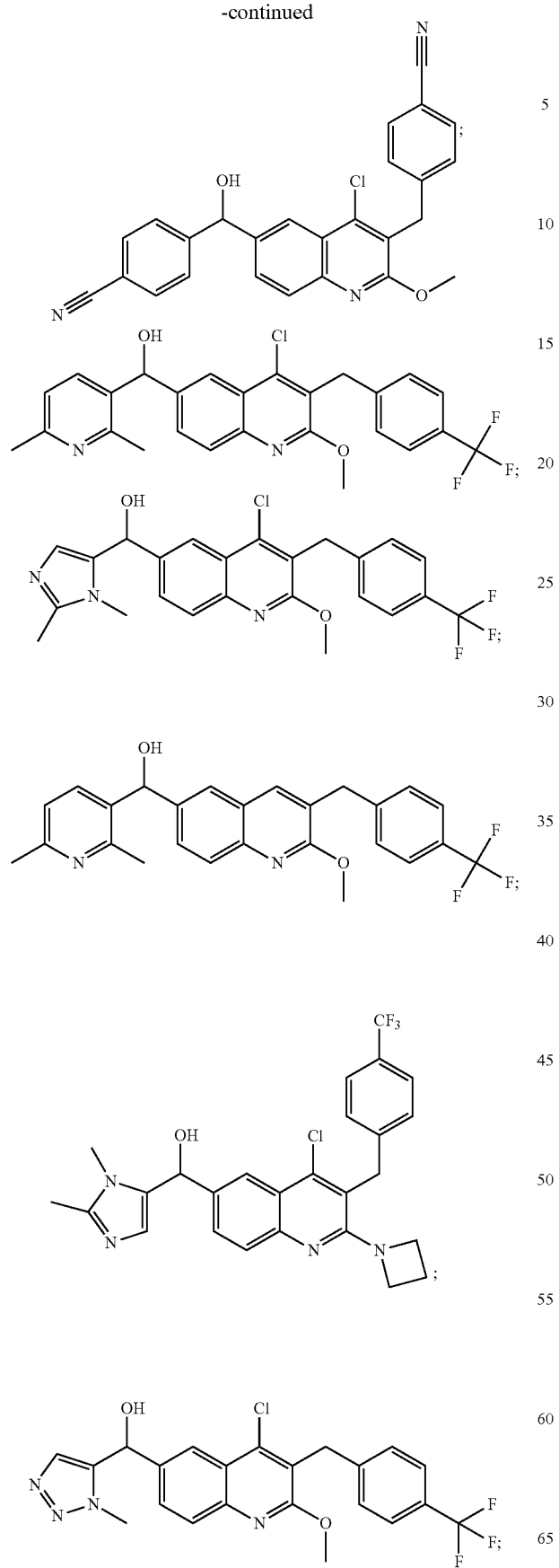
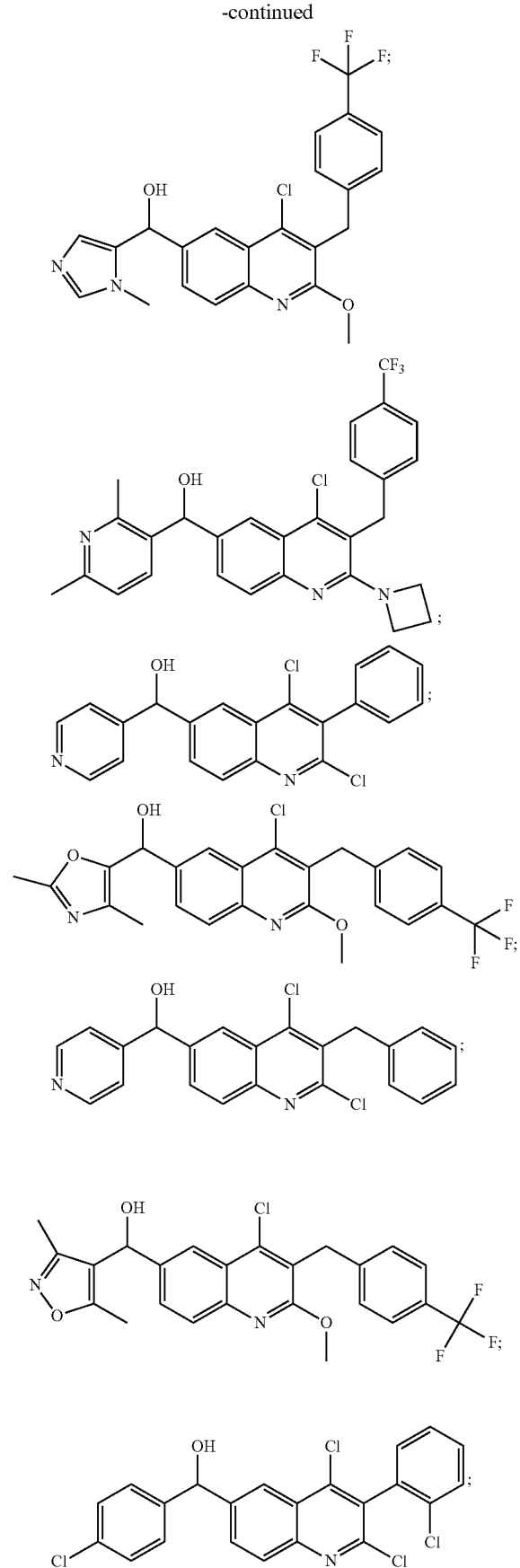

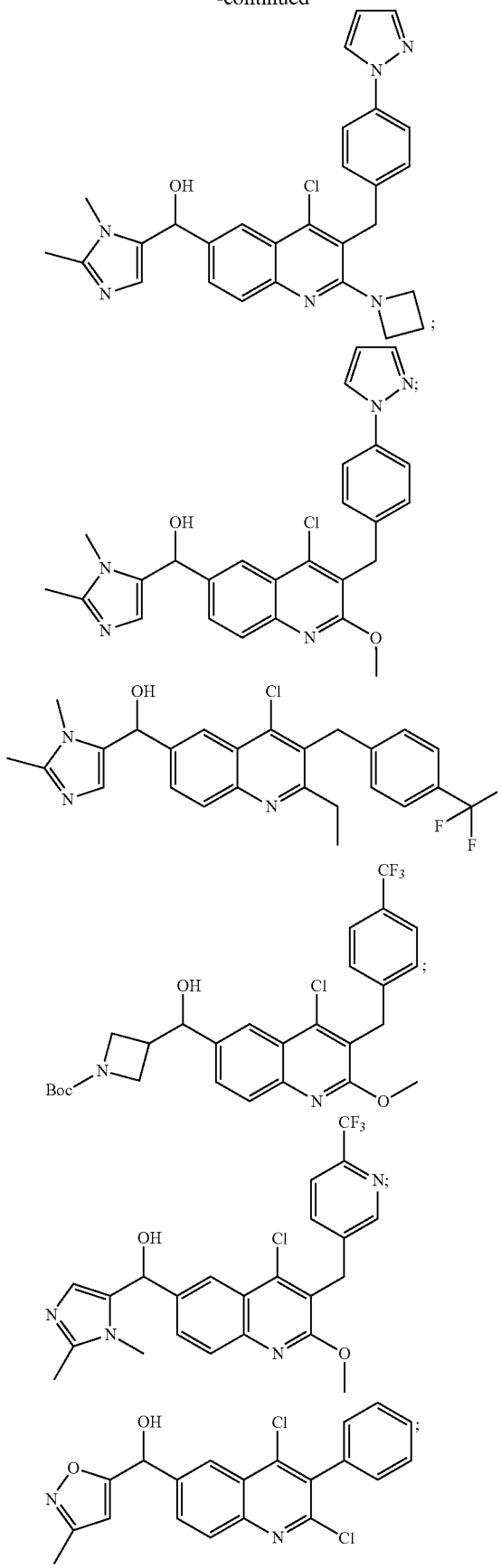
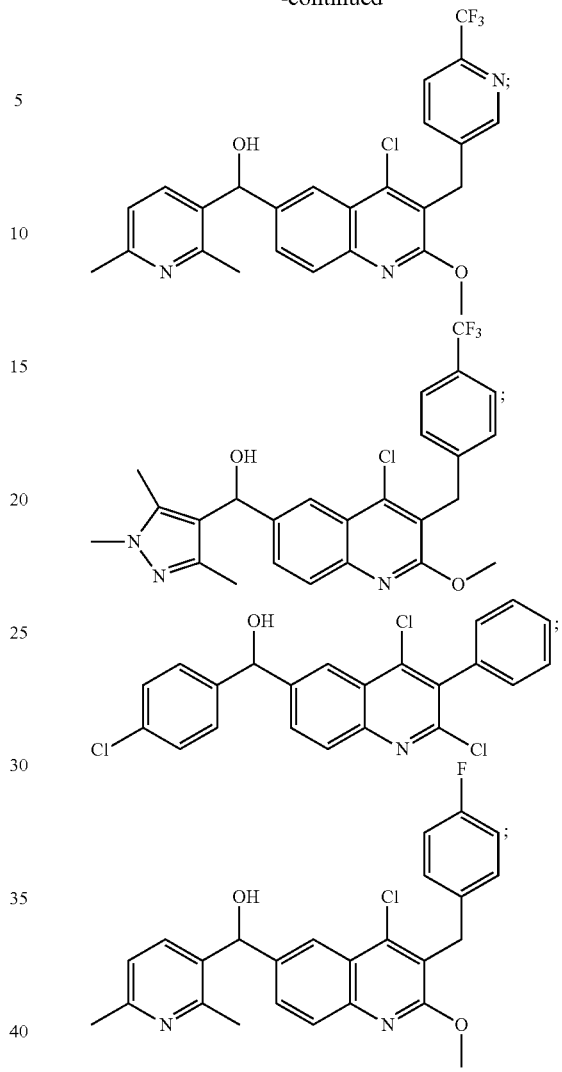

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

DEFINITIONS

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$cycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding.

In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of formula (I) may comprise a radioactive isotope selected from the group of $^3H$, $^{11}C$, $^{18}F$, $^{122}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.

Å angstrom
Ac acetyl
Ac$_2$O acetic anhydride
Boc tert-butyloxy carbonyl
BHT butylated hydroxytoluene
br broad
Bu butyl
n-BuLi n-butyl lithium
d doublet
dba dibenzylideneacetone
DCM dichloromethane
Dess-Martin periodinane 1,1,1-tris(acetyloxy)-1,1-dihydro-1,2-benziodoxol-3-(1H)-one
DMA dimethylacetamide
DMAP 4-dimethylaminopyridine
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
EtMgBr ethylmagnesium bromide
ESI electrospray ionization
Et ethyl
Et$_2$O diethyl ether
EtOAc ethyl acetate
EtOH ethyl alcoh
FCC flash column chromatography
HATU O-(7-azabenzotriazol-1-yl)-N,N,N',N'-tetramethyluronium hexafluorophosphate
HPLC high pressure liquid chromatography
Hunig's base diisopropylethylamine
Hz hertz
i-PrOH isopropyl alcohol
KHMDS potassium bis(trimethylsilyl)amide
LCMS liquid chromatography-mass spectrometry
m multiplet
M molar (moles/liter)
Meldrum's acid 2,2-dimethyl-1,3-dioxane-4,6-dione
MeOH methanol
MHz megahertz
min minutes
mL mililiters
MTBE methyl tertiary butyl ether
nm nanometers
NaOiPr sodium isopropoxide
NMR nuclear magnetic resonance
Ph phenyl
PPA poly phosphoric acid
ppm parts per million
Pr propyl
q quartet
RP-HPLC reverse phase high pressure liquid chromatography
s singlet
t triplet
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Scheme 1 describes the preparation of 6-bromo or 6-iodoquinolines of Formula IV by various methods wherein $R^6$=Ar, —CH$_2$Ar, —OAr, and —NA$^5$Ar and wherein Ar is a phenyl ring or a heteroaryl ring and $A^5$ is H, alkyl, C(O)alkyl, or CO$_2$alkyl as described in the detailed description of the invention. In path 1, cyclization of 4-haloanilines II with 2-substituted malonic acids III can be done in refluxing phosphorus oxychloride to provide 6-haloquinolines IV, wherein $R^5$ and $R^7$ are Cl. The 2-substituted malonic acids III wherein $R^6$ is —CH$_2$Ar, can be obtained through commercial sources or can be prepared by addition of benzaldehydes to Meldrum's acid or dialkyl malonates as described by D. B. Ramachary et al. (*Tetrahedron Letters* 47 (2006) 651-656) followed by aqueous base hydrolysis under either microwave conditions or by heating at temperatures between 100 and 115° C., or treatment with an acid such as trifluoracetic acid in water at temperatures ranging from room temperature to 100° C. Path 2 illustrates how one skilled in the art could generate amides VI by acylation of 4-haloanilines II with substituted acid chlorides V (X=Cl, acid chlorides V are either commercially available or prepared from the corresponding carboxylic acid precursors by procedures known to those skilled in the art) or by coupling with substituted carboxylic acids V (X=OH) in the presence of an appropriate coupling reagent such as EDCI or HATU and a base such as triethylamine. The amides VI can then undergo a formylation-cyclization reaction under Vilsmeier-Haack conditions (POCl$_3$/DMF) as described in WO2007014940 providing 2-chloroquinolines IV wherein $R^5$ is H and $R^7$ is Cl. Path 3 describes the acylation of methyl 2-aminobenzoates VII with acid chlorides V (X=Cl) or with substituted acids V(X=OH) using a coupling agent as previously described to form amide intermediates, which can be further treated with a base, such as sodium ethoxide, Scheme 1

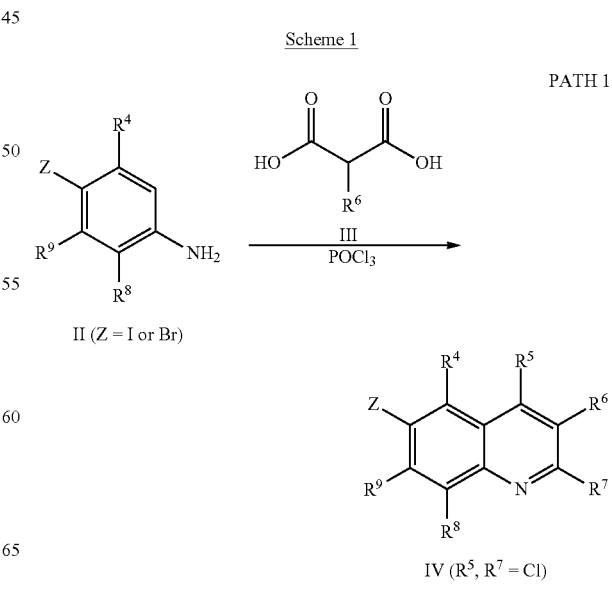

Scheme 1

PATH 1

II (Z = I or Br)

IV ($R^5$, $R^7$ = Cl)

PATH 2

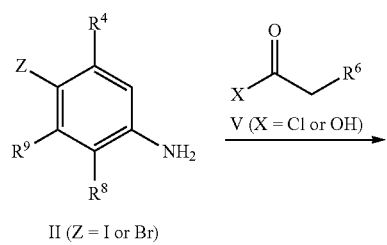

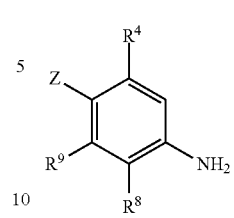

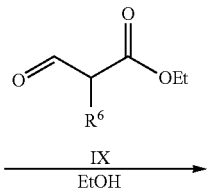

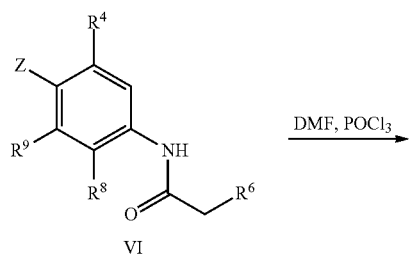

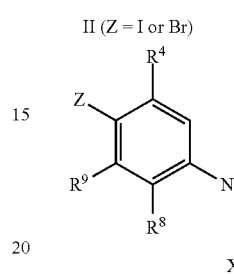

PATH 3

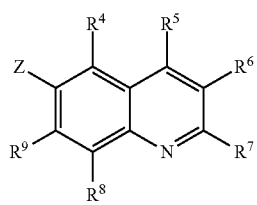

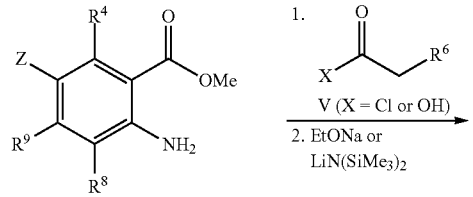

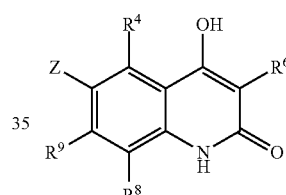

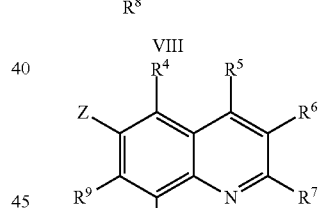

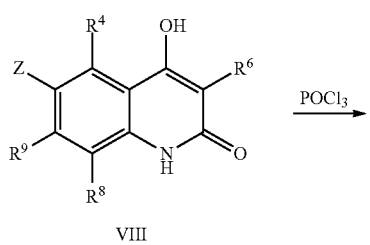

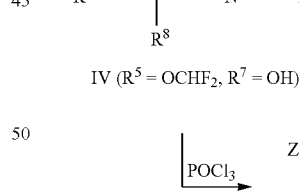

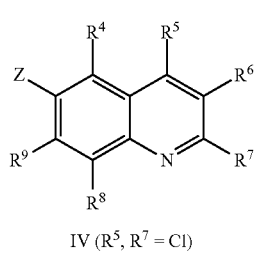

lithium bis(trimethylsilyl)amide or potassium bis(trimethylsilyl)amide, to afford 6-halo-4-hydroxyquinolin-2(1H)-ones VIII. Conversion of hydroxyquinolin-2(1H)-ones VIII to 2,4-dichloroquinolines IV can be carried out in refluxing phosphorus oxychloride. Path 4 describes how one skilled in the art could generate 6-haloquinolines of Formula IV by condensation of anilines II and aldehydes IX in ethanol to form compounds of Formula X which can be further cyclized in polyphosphoric acid at high temperatures followed by treatment with phosphorus oxychloride as previously described to provide 6-haloquinolinones IV wherein $R^5$ is Cl and $R^7$ is H. Path 5 describes how one skilled in the art could generate compounds of Formula IV wherein $R^5$ is difluoromethoxy and $R^7$ is hydroxyl and compounds of Formula IV wherein both $R^5$ and $R^7$ are difluoromethoxy by treating hydroxyquinolin-2(1H)-ones VIII with 2-chloro-2,2-difluoroacetate and a base such as potassium carbonate in a polar aprotic solvent such as DMF. The 6-haloquinolin-2-one IV ($R^5$ is $OCHF_2$ and $R^7$ is OH) can be subsequently treated with phosphorus oxychloride as previously described to provide 6-haloquinolines IV wherein $R^5$ is difluoromethoxy and $R^7$ is Cl.

Scheme 2 illustrates how one skilled in the art could generate 6-haloquinolines of Formula IV by various methods wherein $R^6$=Ar, —$CH_2$Ar, —OAr, and —$NA^5$Ar and wherein Ar is a phenyl ring or a heteroaryl ring and $A^5$ is H, alkyl, C(O)alkyl or $CO_2$alkyl as described in the detailed description of the invention and wherein $R^5$ is Cl and $R^7$ is $CF_3$ (path 1), $R^5$ is $CF_3$ and $R^7$ is Cl (path 2), and $R^5$ and $R^7$ are both $CF_3$ (path 3). In path 1, cyclization of 2-aminobenzoic acids XI with 1,1,1-trifluoropropan-2-ones XII in Eaton's reagent at elevated temperatures could yield 4-hydroxy-2-trifluoromethylquinolines XIII, which upon heating in phosphorus oxychloride at temperatures between 100-120° C. can give 6-haloquinolines IV, wherein $R^5$ is Cl and $R^7$ is $CF_3$. In path 2, 1-halo-4-fluorobenzenes XIV could be deprotonated with lithium diisopropylamide at −78° C. followed by addition of ethyl trifluoroacetate to afford 2-fluorophenyl-2,2,2-trifluoroethanones XV. Displacement of the 2-fluoro substituent in XV with sodium azide followed by reduction of azide intermediates, for example with tin (II) chloride dihydrate, yields anilines XVI. Acylation of anilines XVI with acid chlorides V (X=Cl) or carboxylic acids V (X=OH) as described above leads directly to cyclized quinolin-2(1H)-ones XVII. Heating 4-(trifluoromethyl)quinolin-2(1H)-ones XVII with phosphorus oxychloride in the presence of diisopropylethylamine yields 6-haloquinolines VI wherein $R^5$ is $CF_3$ and $R^7$ is Cl. 6-Halo-2,4-bis(trifluoromethyl)quinolines IV could also be formed by the reaction sequence illustrated in path 3. Cyclization of XVI with 1,1,1-trifluoropropan-2-ones XII in the presence of tributylamine in a polar solvent, such as DMF or DMSO, at high temperatures can provide 6-halo-2,4-bis(trifluoromethyl)quinolines IV wherein $R^5$ and $R^7$ are $CF_3$. In path 3,6-bromo-2,4-bis(trifluoromethyl) quinolines IV (Z=Br) can be transformed into 6-iodo-2,4-bis(trifluoromethyl)quinolines IV (Z=I), with NaI, CuI, and N,N'-dimethylethylenediamine in t-BuOH at high temperatures under microwave conditions.

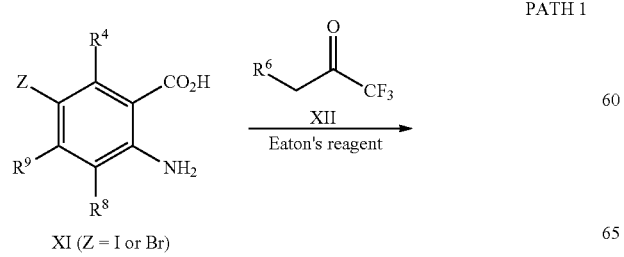

Scheme 2

PATH 3

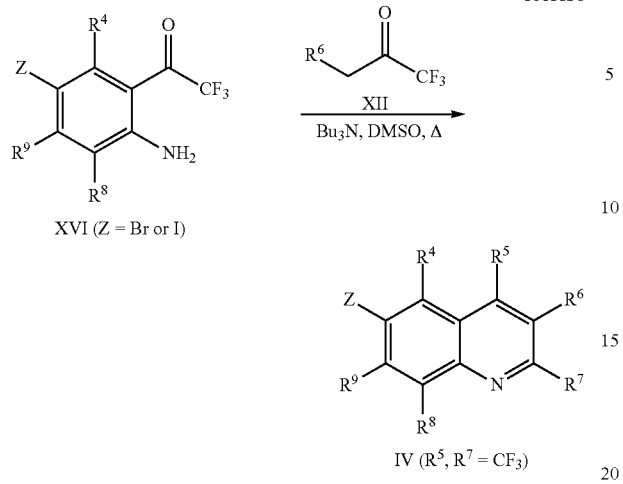

XVI (Z = Br or I)

IV ($R^5$, $R^7$ = $CF_3$)

Scheme 3

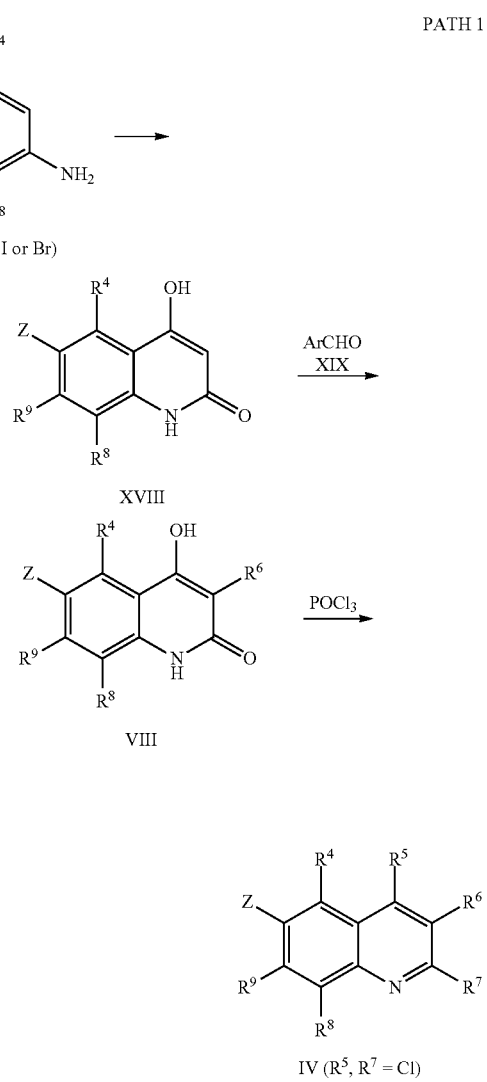

PATH 1

II (Z = I or Br)

XVIII

VIII

IV ($R^5$, $R^7$ = Cl)

Scheme 3 illustrates how one skilled in the art could generate 6-haloquinolines of Formula IV by various methods wherein $R^6$=—$CH_2Ar$ and Ar is a phenyl ring or a heteroaryl as described in the detailed description of the invention. In path 1, hydroxyquinolin-2(1H)-ones XVIII [prepared by condensation of readily available 6-bromo or 6-iodoanilines II with Meldrum's acid and then subsequently heated in the presence of Eaton's reagent or PPA as described by W. T. Gao, et al. (*Synthetic Communications* 2010, 40, 732)] can be condensed with substituted aldehydes of the formula ArCHO (XIX) in the presence of a Hantzsch ester, such as diethyl 2,6-dimethyl-1,4-dihydropyridine-3,5-dicarboxylate, in solvents like ethanol or pyridine to afford substituted 6-halo-4-hydroxyquinolin-2(1H)-ones VIII wherein $R^6$ is —$CH_2Ar$. Subsequent heating of quinolines VIII in the presence of phosphorus oxychloride at temperatures between 80-120° C. with or without a solvent, such as acetonitrile, can provide the 6-haloquinolines IV wherein $R^5$ and $R^7$ are Cl. In path 2, hydroxyquinolin-2(1H)-ones XVIII can be transformed into the dichloroquinolines XX with phosphorus oxychloride as described above. Deprotonation at the C3-position of the quinoline ring with a base such as lithium diisopropylamine in a solvent such as tetrahydrofuran at low temperatures such as −78° C. to 0° C. followed by addition of benzyl halide reagents XXI can provide 6-haloquinolines IV wherein $R^6$ is —$CH_2Ar$ and both $R^5$ and $R^7$ are Cl. Compounds of Formula IV, wherein $R^7$ is alkyl, can be prepared as illustrated in path 3. Intermediates of Formula XXII can be prepared by deprotonation of β-keto esters, such as ethyl 3-oxobutanoate or ethyl 3-oxopentanoate, with a base like sodium hydride followed by alkylation with substituted alkyl halides. Intermediates of Formula XXII can also be prepared by condensation of β-keto esters, such as ethyl 3-oxobutanoate or ethyl 3-oxopentanoate with aldehydes in the presence of piperdine and acetic acid in a solvent such as benzene followed by palladium catalyzed hydrogenation in a solvent such as ethanol. Condensation with 4-haloanilines II in the presence of an acid, such as para-toluenesulfonic acid (PTSA), in refluxing toluene with concomitant removal of water followed by intramolecular cyclization at elevated temperature affords 4-hydroxy quinolines XIII, wherein $R^7$ is alkyl. The hydroxyl group can then be converted to a chloro group by heating in acetonitrile with phosphorus oxychloride to provide 6-haloquinolines IV wherein $R^5$ is Cl and $R^7$ is alkyl.

PATH 2

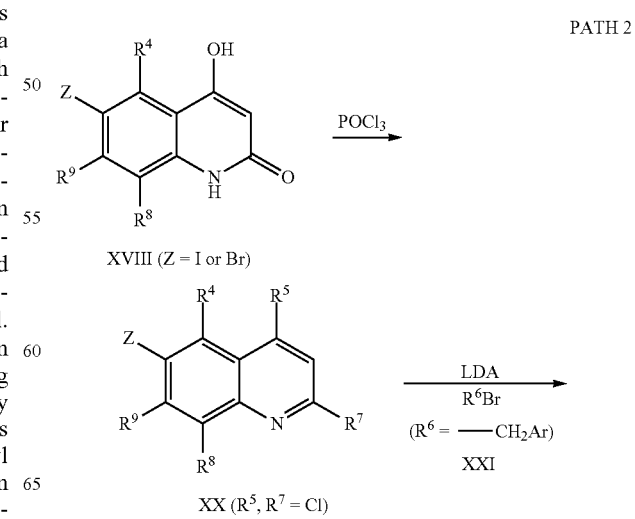

XVIII (Z = I or Br)

XX ($R^5$, $R^7$ = Cl)

XXI ($R^6$ = —$CH_2Ar$)

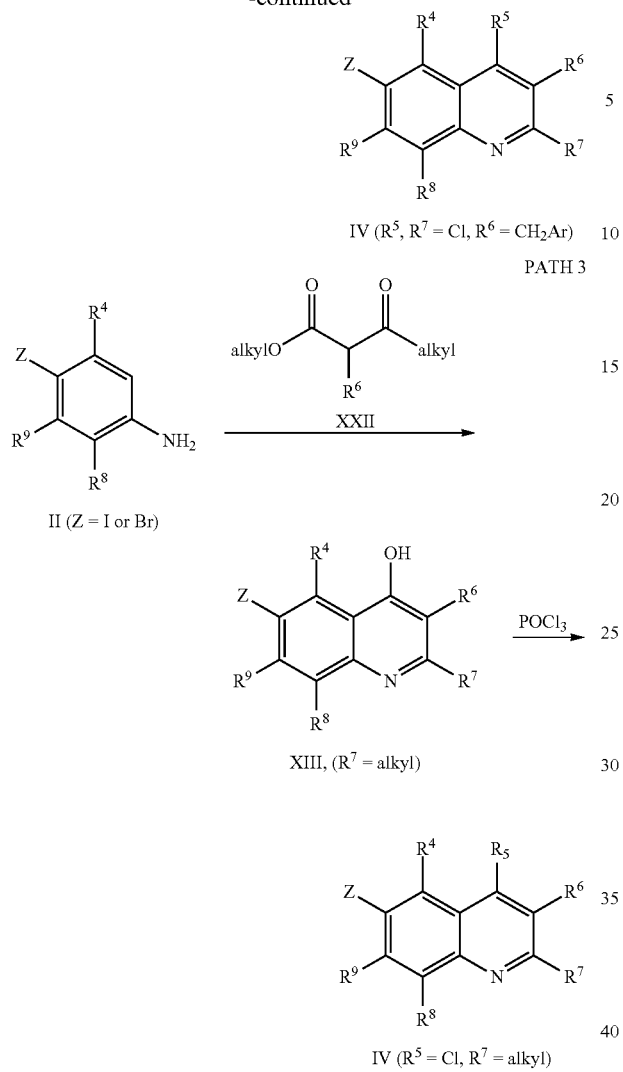

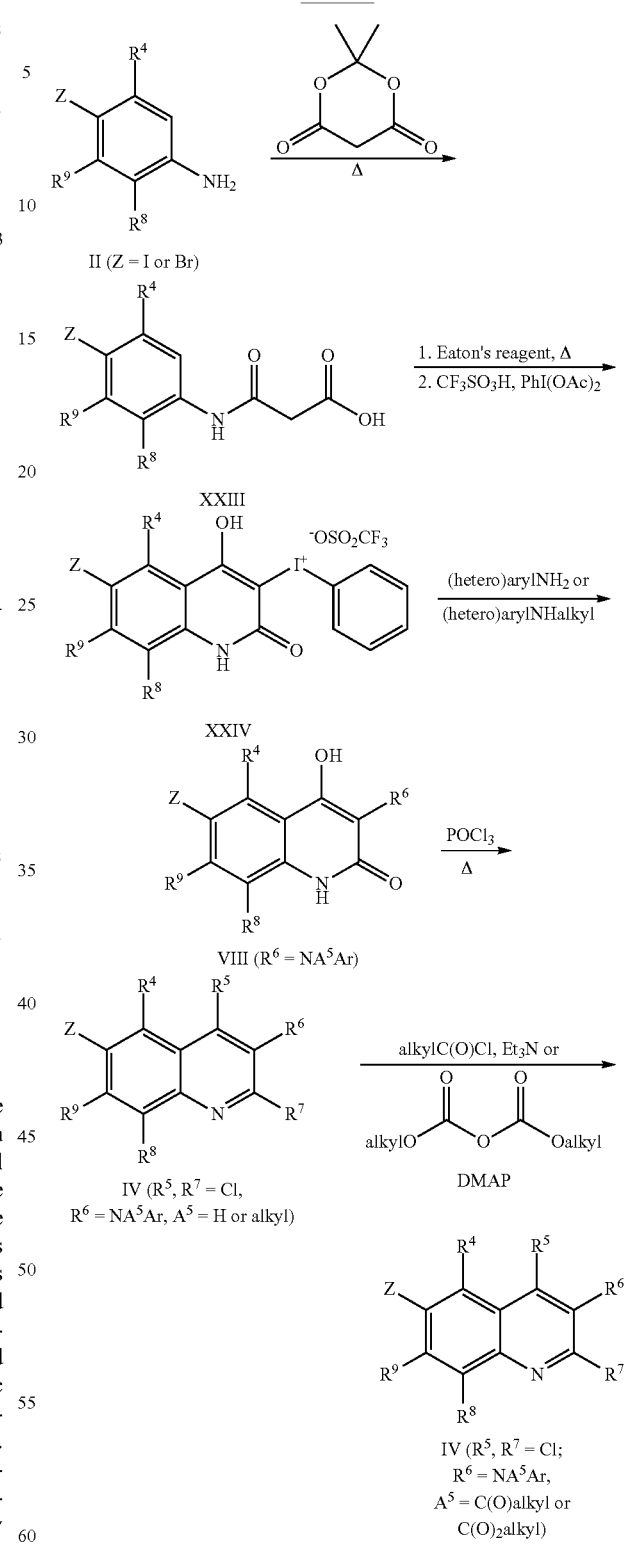

An alternative route for one skilled in the art to prepare 6-haloquinolines IV where $R^6$ is —$NA^5Ar$ wherein Ar is a phenyl ring or a heteroaryl ring and $A^5$ is H, alkyl, C(O)alkyl or $CO_2$alkyl as described in the detailed description of the invention is shown in Scheme 4. 4-Haloanilines II can be heated with 2,2-dimethyl-1,3-dioxan-4,6-dione (Meldrum's acid) to form 3-((4-halophenyl)amino)-3-oxopropanoic acids XXIII. Cyclization of XXIII in Eaton's reagent at elevated temperature can then afford 4-hydroxyquinolinone intermediates (Synth. Commun. 2010, 40, 732), which can be treated with (diacetoxyiodo)benzene and trifluoromethanesulfonic acid to yield 4-hydroxyquinolinone phenyliodoniumtrifluoromethane sulfonates XXIV (Org. React. 2001, 57, 327). Reaction of these intermediates with arylamines or heteroarylamines could yield substituted 3-amino-4-hydroxyquinolinones VIII (Monatsh. Chem. 1984, 115 (2), 231), which may be heated in phosphorus oxychloride to afford 2,4-dichloroquinolines IV. In cases where $R^6$ is a secondary amine, these intermediates may be further functionalized to form amides by reaction with an acid chloride and a tertiary amine base, or to form carbamates by reaction with a dialkyl dicarbonate, such as di-tert-butyl dicarbonate, and DMAP in a polar solvent such as THF or DMF.

6-Haloquinolines VI where $R^5$ is Cl, $R^7$ is H and $R^6$ is $NA^5Ar$ or OAr can also be prepared by the methods shown in Scheme 5. In path 1, 4-haloanilines II can be reacted with in situ generated methoxymethylene Meldrum's acid to form enamines XXV which can cyclize by heating in the range of 250-300° C. in a non-polar, high-boiling solvent such as diphenyl ether, to provide 4-hydroxyquinolines XXVI (Madrid, P. B. et al., Bioorg. Med. Chem. Lett., 2005, 15, 1015). 4-Hydroxyquinolines XXVI may be nitrated at the 3-position by heating with nitric acid in an acidic solvent, such as propionic acid, to provide 3-nitro-4-hydroxyquinolines XXVII (path 2). Heating these intermediates with $POCl_3$ and reduction of the nitro group, for instance using tin(II) chloride dihydrate, provides 3-amino-4-chloroquinolines XXVIII. N-Arylation or N-heteroarylation can be accomplished using aryl or heteroaryl boronic acids and a copper salt, such as $Cu(OAc)_2$, in the presence of a tertiary amine base. Alternatively, the primary amines can be further elaborated by N-alkylation or acylation with an alkyl halide or alkyl acid chloride and a base to provide 6-haloquinolines of Formula VI wherein $R^5$ is Cl, $R^6$ is —$NA^5Ar$ wherein Ar is a phenyl ring or a heteroaryl ring and $A^5$ is H, alkyl, or C(O)alkyl as described in the detailed description of the invention, and $R^7$ is H. Alternatively, 4-hydroxyquinolines XXVI may be brominated at the 3-position by heating with N-bromosuccinimide in acetic acid to furnish 3-bromo-4-hydroxyquinolines XXIX (path 3). Displacement of the 3-bromo substituent can be accomplished by heating with an aryl or heteroaryl potassium phenoxide salt in the presence of copper powder and copper (I) bromide in a polar solvent, such as DMF, as described in Collini, M. D. et al., US 20050131014. The resulting 4-hydroxyquinolines XXX can be heated in $POCl_3$ to provide 6-haloquinolines VI where R is Cl, $R^6$ is —OAr, wherein Ar is a phenyl ring or a heteroaryl ring as described in the detailed description of the invention, and $R^7$ is H.

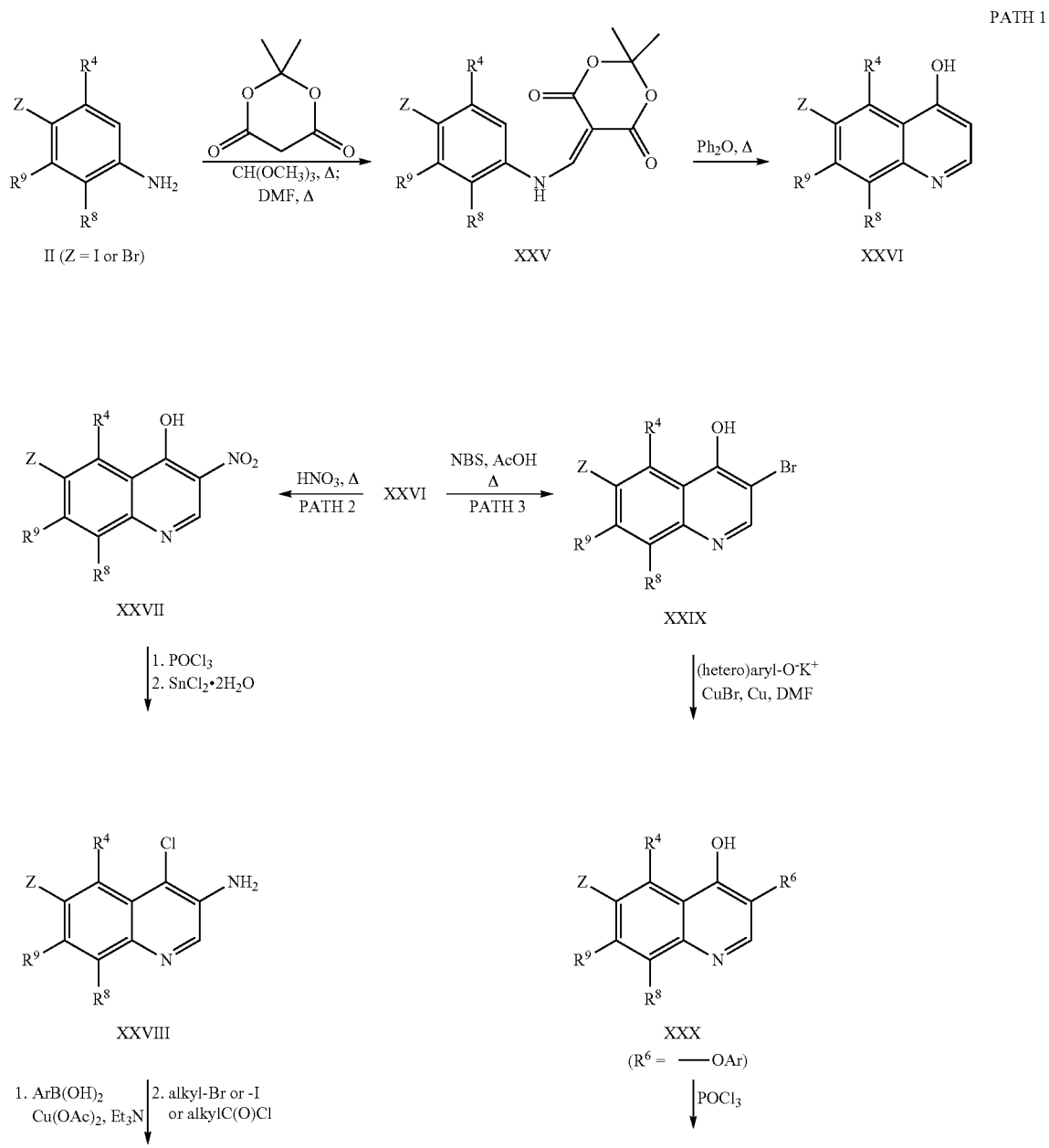

Scheme 5

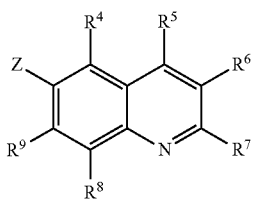

VI (R$^5$ = Cl, R$^7$ = H,
R$^6$ = ——NA$^5$Ar)

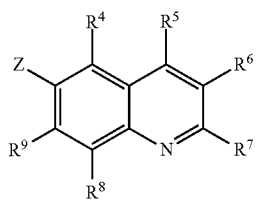

VI (R$^5$ = Cl, R$^7$ = H,
R$^6$ = ——OAr)

Scheme 6 provides methods used to displace the 2-Cl of 6-haloquinolines IV with oxygen or nitrogen neuclophiles. As shown in path 1, displacement of the 2-Cl with sodium alkoxides can be accomplished in an alcoholic solvent such as methanol, ethanol or isopropanol or at elevated temperatures or in a non-polar solvent such as toluene (Alan Osborne et al. *J. Chem. Soc. Perkin Trans.* 1 (1993) 181-184 and *J. Chem. Research (S)*, 2002, 4) to provide substituted quinolines IV, wherein R$^7$ is Oalkyl. Likewise 6-haloquinolines of Formula IV where R$^7$ is NA$^1$A$^2$ can be obtained by displacement of the 2-Cl group with substituted amines (path 2).

lines IV in an appropriate solvent such as tetrahydrofuran can either be premixed with commercially available aldehydes XXXII or aldehydes XXXII prepared as described in Scheme 7 at −78° C. followed by addition of n-BuLi or can be pretreated with n-BuLi (or iPrMgCl) at −78° C. prior to the addition of the aldehydes XXXII to afford the secondary alcohols of Formula 1, wherein R$^2$=H and R$^3$=OH. If a cycloheteroaliphatic aldehyde is used as R$^1$CHO, such as tert-butyl 4-formylpiperidine-1-carboxylate, the ter-butyl carboxylate group can be removed with an acid such as trifluoroacetic acid and the resulting piperidine nitrogen can be Scheme 6

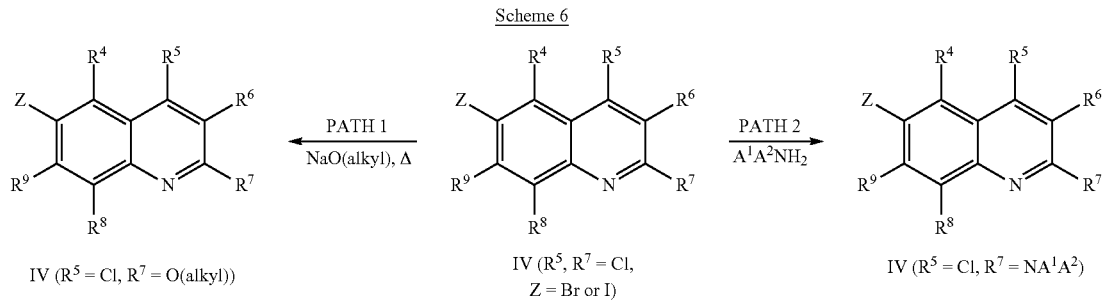

IV (R$^5$ = Cl, R$^7$ = O(alkyl))

IV (R$^5$, R$^7$ = Cl,
Z = Br or I)

IV (R$^5$ = Cl, R$^7$ = NA$^1$A$^2$)

Scheme 7 depicts the synthesis of aldehydes of the Formula XXXII. As shown in path 1, aryl or heteroaryl halides XXXI are transformed into the corresponding organolithium or organomagnesium reagents with n-BuLi or a Grignard (such as i-PrMgCl or EtMgCl), respectively, and then trapped with dimethylformamide to provide aldehydes XXXII. Alternatively, as shown in path 2, aryl or heteroaryl compounds XXXIII with an acidic proton can be deprotonated with n-BuLi and trapped with dimethylformamide to provide aldehydes XXXII.

acylated with acid chlorides or anhydrides, such as acetic anhydride, to form the corresponding amide. In path 2, 6-haloquinolines IV can be treated with n-BuLi or i-PrMgCl to form the corresponding aryllithium or aryl Grignard intermediate, respectively, which when trapped with dimethylformamide can afford aldehydes XXXIV. Addition of an organolithium or organomagnesium reagent (R$^1$-M), generated as described in Scheme 7 above, to aldehyde XXXIV could provide secondary alcohols of the Formula I, wherein R$^2$=H and R$^3$=OH.

Scheme 7

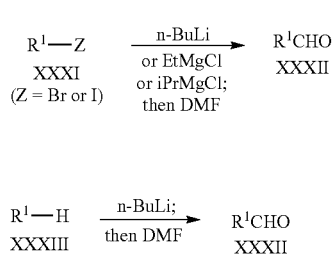

Scheme 8

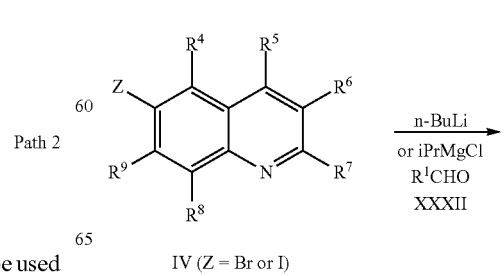

Scheme 8 exemplifies synthetic methods that could be used to prepare compounds of Formula I. In path 1, 6-haloquino-

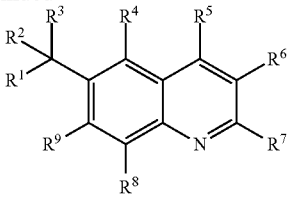

I (R² = H, R³ = OH)

Path 2

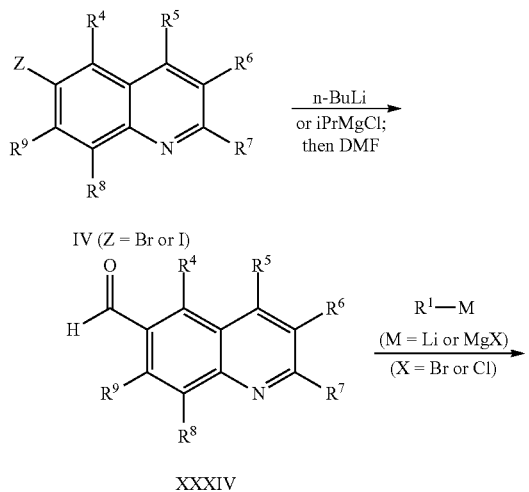

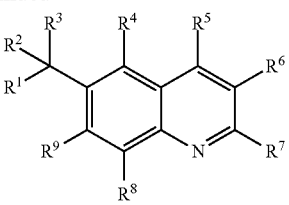

I (R² = H, R³ = OH)

Scheme 9 describes an alternative synthesis of compounds of Formula I. Benzoic acids XXXV can be converted to the N,O-dimethyl hydroxamic acid derivatives XXXVI, which following treatment with an organolithium or organomagnesium reagent that is commercially available or generated as described in Scheme 7 above, provides ketones XXXVII. The nitro group can then be reduced with reagents such as tin (II) chloride under standard conditions well known in the art, to provide ketoanilines XXXVIII. The ketoanilines XXXVIII can be condensed with malonic acids III in phosphorus oxychloride as previously described to form 6-ketoquinolines XXXIX wherein $R^5$ and $R^7$ are Cl. Conversion of the chlorine at the 2-position can be achieved as described above to provide ketoquinolines XL wherein $R^5$ is Cl and $R^7$ is Oalkyl. Reduction of the keto group with a reductant such as sodium borohydride in a solvent such as methanol provides compounds of Formula 1, wherein $R^2$=H and $R^3$=OH.

Scheme 9

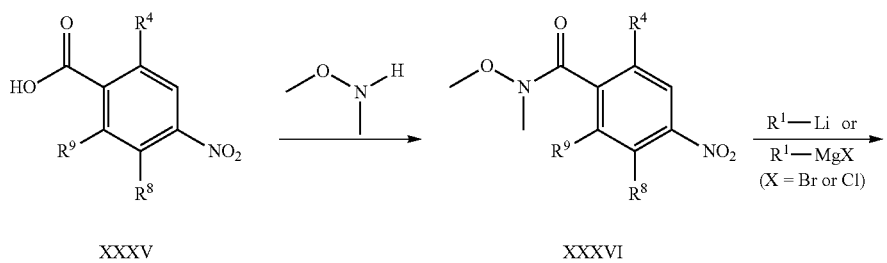

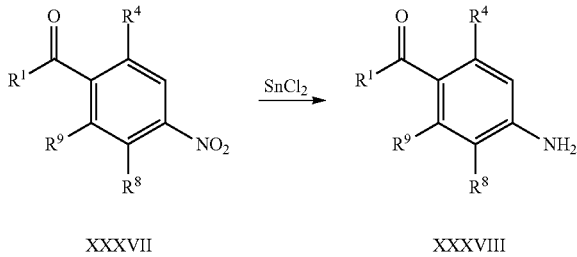

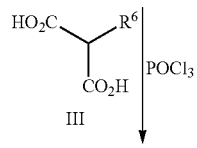

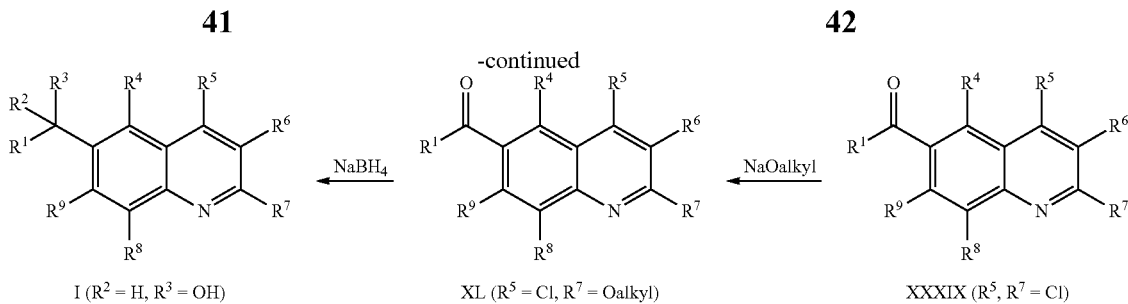

Scheme 10 illustrates methods used to synthesize compounds of Formula I wherein either the chlorine at $R^5$, $R^7$ or at both $R^5$ and $R^7$ positions are replaced with nitrogen, oxygen, sulfur or alkyl groups. In path 1 and 4, nucleophilic displacement of 2,4-dichloroquinolines of Formula I ($R^5$ and $R^7$ are Cl) with NaO(alkyl), NaS(alkyl), such as NaOMe, NaSMe, NaOEt, or NaO$^i$Pr, in an appropriate solvent, such as MeOH, EtOH, i-PrOH or DMF at elevated temperatures or with substituted hydroxy reagents such as 2-methoxyethanol in the presence of a base like sodium hydride in a non-polar solvent such as toluene (as described above) could provide compounds of Formula I wherein $R^5$ is Cl and $R^7$ is O(alkyl), O(CH$_2$)$_2$OCH$_3$ or S(alkyl) and compounds of Formula I wherein $R^5$ and $R^7$ are O(alkyl) or S(alkyl). Likewise, nucleophilic displacement of 2,4-dichloroquinolines of Formula I ($R^5$ and $R^7$ are Cl) with primary or secondary alkyl amines, heterocycles amines, or N,O-dimethylhydroxylamine in polar solvents such as MeOH, EtOH, or Et$_2$NCHO, or DMF could provide quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$. NHC$_{(2-3)}$alkylNA$^1$A$^2$ or N(CH$_3$)C$_{(2-4)}$alkylNA$^1$A$^2$, wherein A$^1$ and A$^2$ are as defined above. Replacement of chlorine at positions 2 and 4 of quinolines of Formula I ($R^5$ and $R^7$ are Cl) with alkyl groups could be carried out using Zn(alkyl)$_2$ in the presence of K$_2$CO$_3$ and a palladium catalyst, such as PdCl$_2$(dppf), to afford 2-alkyl and 2,4-dialkylguinolines of Formula I (path 3).

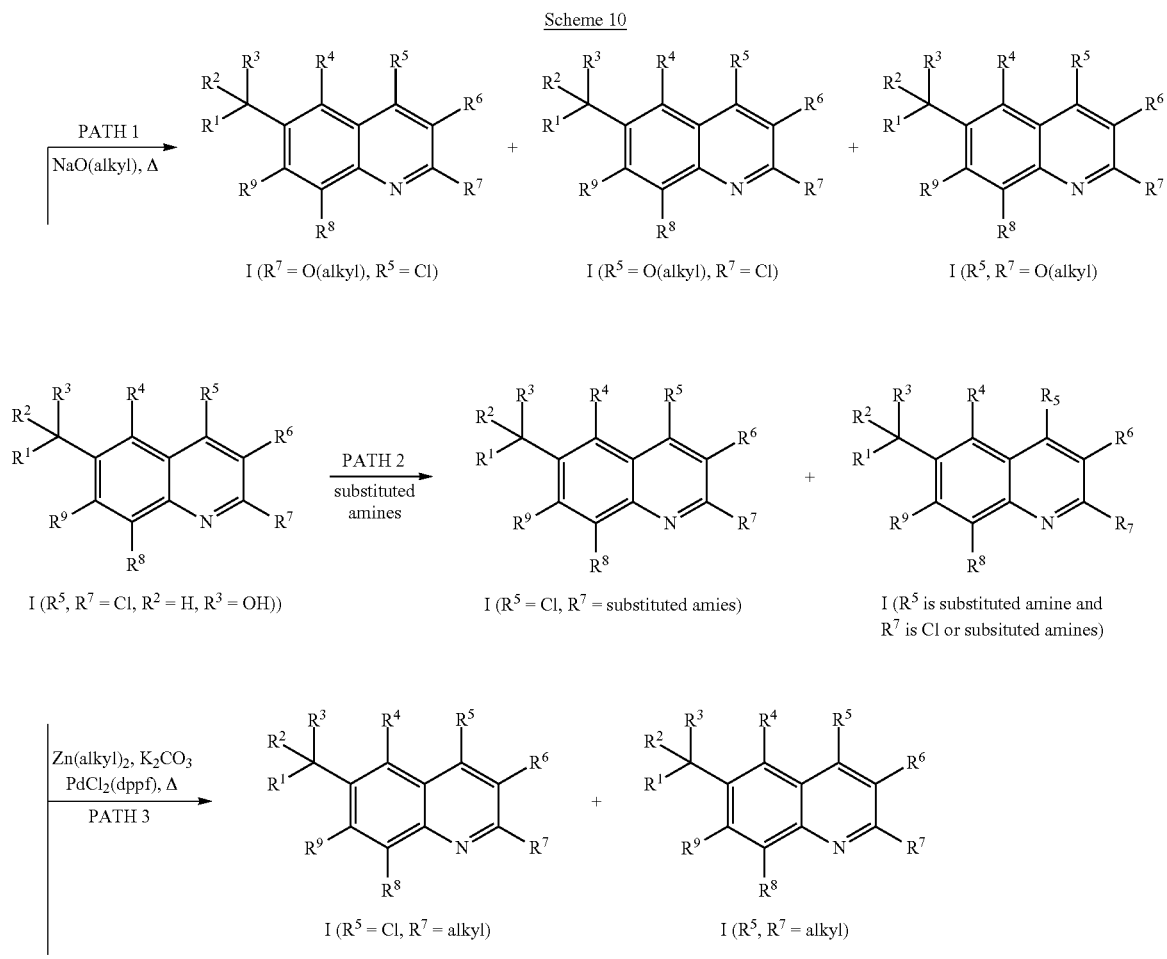

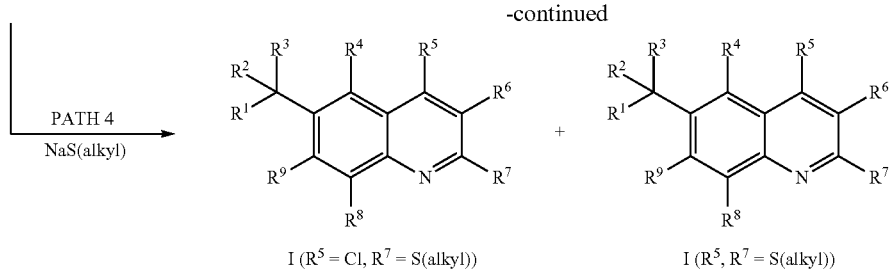

Synthetic routes to compounds of Formula I, wherein R is Cl or CN, and $R^7$ is CN or aryl, are illustrated in Scheme 11. In path 1, cyanation of the 2,4-dichloroquinolines of Formula I with $Zn(CN)_2$ in the presence of Zn, a palladium catalyst, such as $Pd_2dba_3$, and a ligand, such as dppf or X-phos, at high temperatures can provide 2-CN and 2,4-diCN quinolines of Formula I. The 2,4-dichloroquinolines of Formula I can also undergo a Suzuki reaction with $ArB(OH)_2$ or $ArB(OR)_2$ and a palladium catalyst, such as $PdCl_2(dppf)$, yielding compounds of Formula I wherein $R^7$ is phenyl, substituted phenyl and five or six-membered heteroaryls such as furan, pyridine, pyridazine, pyrazine, pyrimidine, pyrrole, pyrazole or imidazole (path 2).

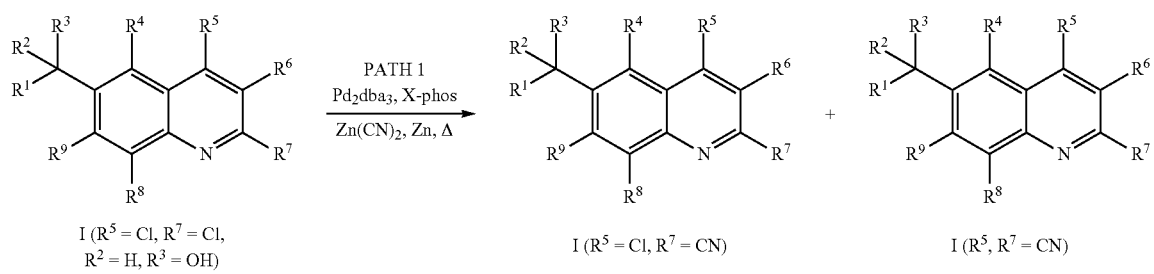

Scheme 11

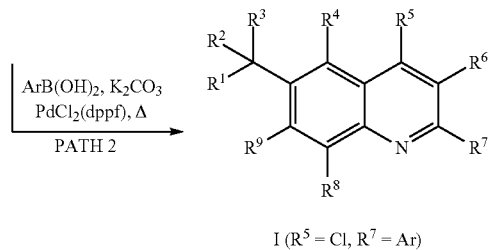

As illustrated in Scheme 12, compounds of Formula I wherein $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as described above. Palladium catalyzed hydrogenation, as shown in path 4, could also provide compounds of Formula 1, wherein $R^5$ is H.

Scheme 12
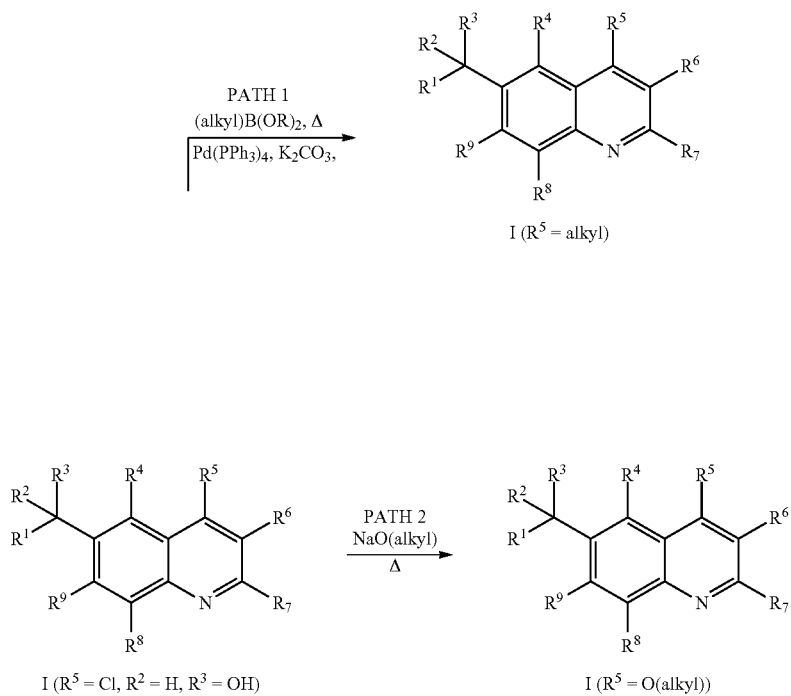
Scheme 13 describes methods known to those skilled in the art which could lead to compounds of Formula I wherein $R^3$=OMe. Compounds of Formula 1 can be treated with base, such as NaH, and alkylated with MeI in DMF to provide compounds of Formula I wherein $R^3$ is OMe.

Scheme 13

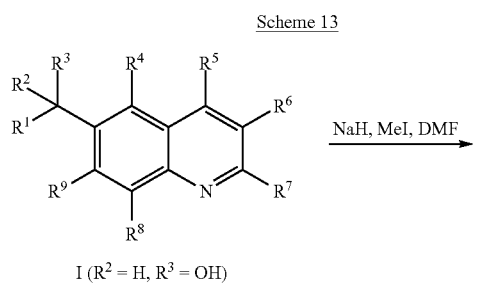

as described in Scheme 7) with 2-methylpropane-2-sulfinamide in refluxing THF. Addition of n-BuLi to the reaction mixture of aldimines XLI and 6-bromo or 6-iodoquinolines IV at −78° C. followed by cleavage of tert-butanesulfinyl group with HCl in MeOH liberates amines I, wherein $R^3$=$NH_2$. Alternatively, compounds of Formula I, wherein $R^3$ is OH, can be treated with sodium hydride followed by addition of acetic anhydride or acetyl chloride and stirred at room temperature over a 24 to 72 hour period to provide the intermediate acetate wherein $R^3$ is OAc. The acetate can then be combined with a solution of ammonia in methanol and heated at temperatures between 60 and 85° C. to provide compounds of Formula I, wherein $R^3$ is $NH_2$.

Scheme 14

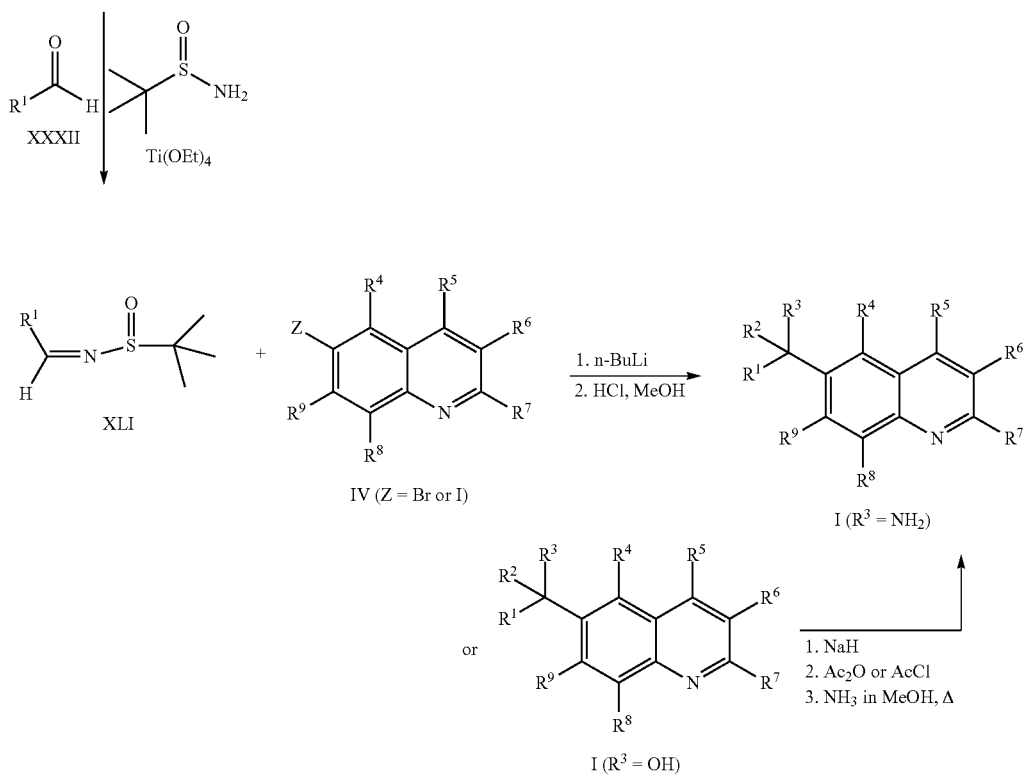

-continued

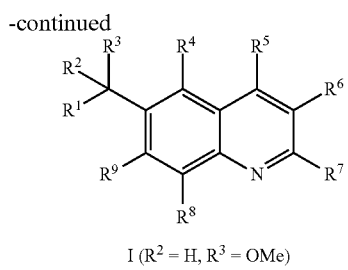

Synthetic routes that can lead to compounds of Formula I, wherein $R^3$ is $NH_2$, are illustrated in Scheme 14. Aldimines XLI may be prepared by Ti(OEt)$_4$ mediated condensation of commercially available aldehydes XXXII (or those prepared As shown in Scheme 15, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert CN to a carboxylic acid XLII (path 2). Once formed the acid can be further coupled to substituted amines using appropriated coupling reagents such as EDCI or HATU in the presence of a base such as triethylamine or Hunig's base to provide compounds of Formula I wherein $R^7$ is $CONA^1A^2$.

Scheme 15

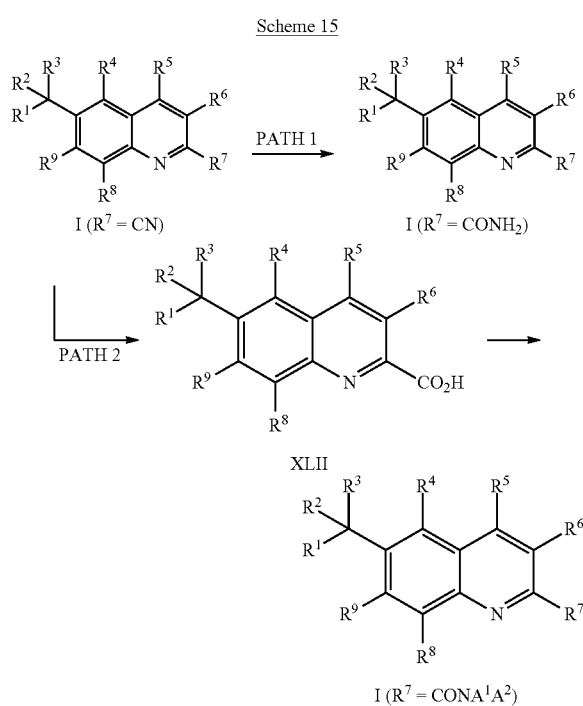

Synthesis of compounds of Formula I, wherein $R^7$ is an aminoalkylaminomethylene or an aminoalkoxymethylene, can be prepared from 2-methylquinolines as shown in Scheme 16. Bromination of 2-methylquinolines of Formula I can be accomplished with N-bromosuccinimide in acetic acid at elevated temperatures as described in WO2010151740, to provide the methylbromide intermediates XLIII. Nucleophilic displacement of the bromide under basic conditions using procedures known in the art could afford compounds of Formula I wherein $R^7$ is —$CH_2N(H)C_{(2-3)}alkylNA^1A^2$ or —$CH_2N(CH_3)C_{(2-3)}alkylNA^1A^2$ (path 1) or $CH_2OC_{(2-3)}alkylNA^1A^2$ (path 2) and $A^1$ and $A^2$ are defined above.

Scheme 17 outlines alternative synthetic methods to compounds of Formula I wherein $R^6$ is Ar wherein Ar is defined as phenyl ring, or heteroaryl ring as defined in the detailed description of the invention, which could be used by one skilled in the art. Acylation of anilines VII with benzyloxyacetyl chloride in the presence of a base such as triethylamine in a solvent such as dichloromethane affords amides XLIV. Amides XLIV can undergo an intramolecular cyclization reaction with a base such as potassium bis(trimethylsilyl)amide in a solvent such as tetrahydrofuran to provide 6-halo-4-hydroxyquinolin-2(1H)-ones VIII, wherein $R^6$ is OBn. Conversion to the 2,4-dichloroquinolines IV can be accomplished in phosphorus oxychloride as previously described. The coupling of 6-haloquinolines IV and aldehydes of Formula XXXII followed by displacement of the 2 or 4-chloro using procedures previously described provides quinolines of Formula XLV wherein $R^6$ is OBn and $R^1$, $R^2$, $R^5$ and $R^7$ are defined above. Palladium-catalyzed hydrogenation of compounds of Formula XLV that are substituted with a benzyloxy at C-3 can provide intermediate quinolin-3-ols XLVI. The quinoline-3-ols XLVI can be converted into the corresponding triflates XLVII with trifluoromethanesulfonic acid in the presence of a base, such as pyridine, in a solvent such as dichloromethane. The triflates XLVII can be converted into compounds of Formula I, wherein $R^6$ is aryl or heteroaryl as defined above, by a palladium-catalyzed cross coupling with organoboron reagents of the formula $R^6B(OR)_2$ in the presence of a base, such as potassium carbonate, in a solvent mixture such as 1,4-dioxane/water.

Scheme 16

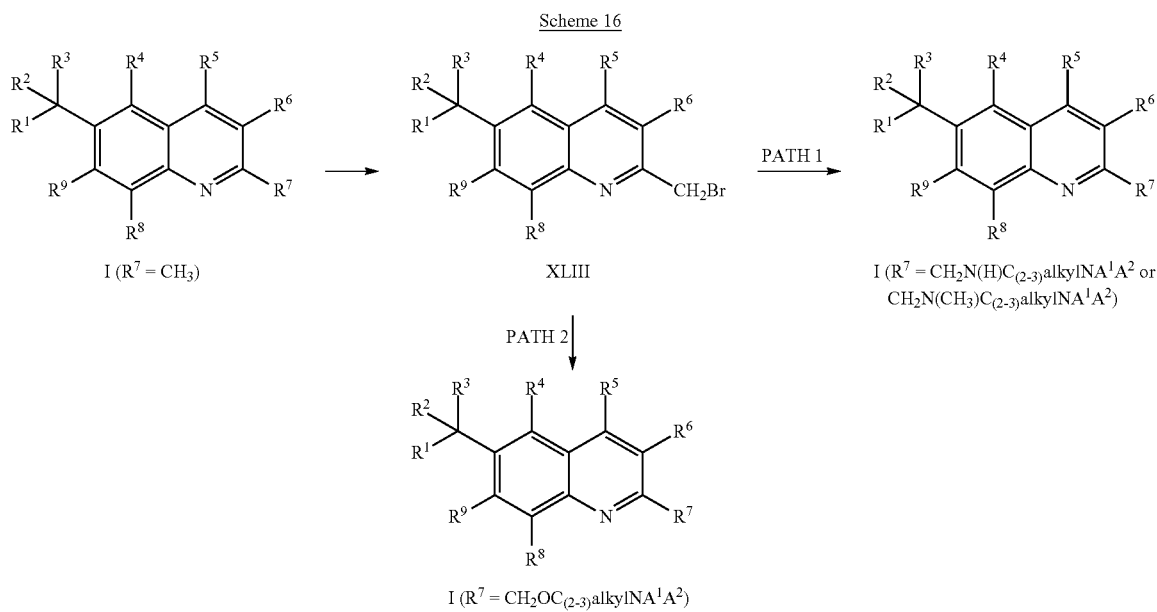

Scheme 17

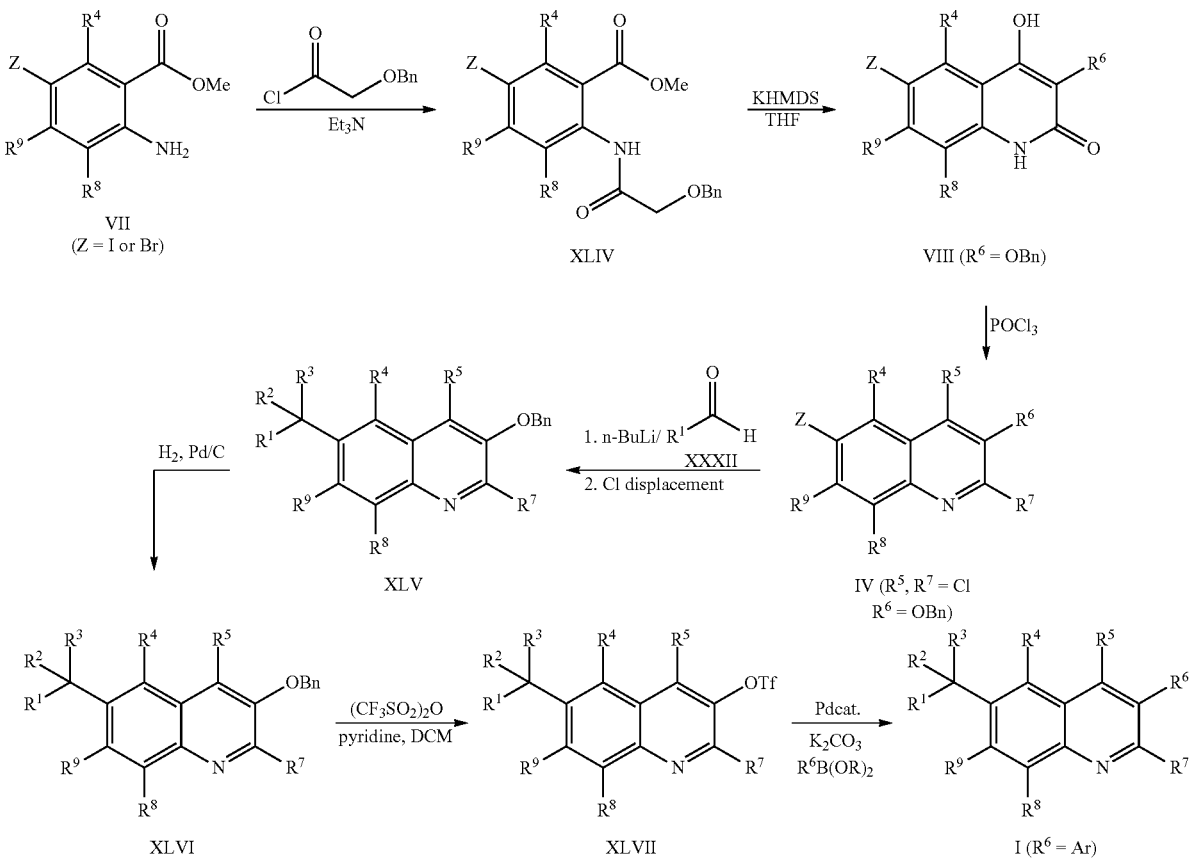

Compounds of Formula I wherein $R^1$ or $R^6$ are pyridyl can be treated with m-chloroperbenzoic acid in a chlorinated solvent at ambient temperature to 40° C. to form the pyridyl-N-oxides of Formula I.

EXAMPLES

Compounds of the present invention can be prepared by methods known to those who are skilled in the art. The following examples are only meant to represent examples of the invention and are in no way meant to be a limit of the invention.

Intermediate 1: Step a

Methyl 5-bromo-2-(2-phenylacetamido)benzoate

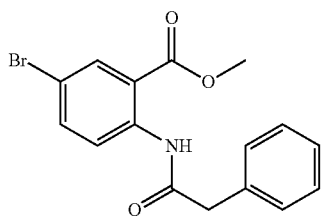 [SMILES: COC(=O)c1cc(Br)ccc1NC(=O)Cc1ccccc1]

To a mixture of methyl 2-amino-5-bromobenzoate (9.00 g, 39.1 mmol) and $Et_3N$ (7.6 mL, 54.8 mmol) in $CH_2Cl_2$ (90 mL) was added 2-phenylacetyl chloride (7.26 g, 46.9 mmol) at 4° C. dropwise. After completion of the addition, the cooling bath was removed and the mixture was stirred for 27 hours. TLC showed some of the starting material methyl 2-amino-5-bromobenzoate still remained. More 2-phenylacetyl chloride (1.88 g, 12.2 mmol) and $Et_3N$ (2.2 mL, 15.9 mmol) were added, and the mixture was stirred overnight. $K_2CO_3$ (aqueous) was added, the organic layer was separated, and the aqueous layer was extracted with $CH_2Cl_2$. The combined organic layers were washed with water, dried ($Na_2SO_4$), filtered, and concentrated in vacuo. $CH_3CN$ (100 mL) was added, and the precipitated solid was filtered, washed with $Et_2O$, and dried to provide the title compound. The filtrate was concentrated in vacuo, and the solid was filtered, washed with $Et_2O$, and dried to afford additional title compound.

Intermediate 1: Step b

6-Bromo-4-hydroxy-3-phenylquinolin-2(1H)-one

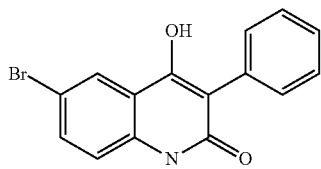 [SMILES: O=c1[nH]c2ccc(Br)cc2c(O)c1-c1ccccc1]

To a solution of methyl 5-bromo-2-(2-phenylacetamido) benzoate (7.71 g, 22.1 mmol, Intermediate 1: step a) in THF (50 mL) at −78° C. was added 1.0 M lithium bis(trimethylsilyl)amide in hexane (48.7 mL, 48.7 mmol) slowly, and the color changed from colorless to clear red. The mixture was stirred at −78° C. to room temperature for 4 hours, during which time the color changed to cloudy yellow. The reaction was quenched with water, and acidified with 37% HCl until pH 5. The precipitated solid was filtered, washed with water and Et$_2$O, and air dried to provide the title compound. More solid was precipitated from the filtrate after standing overnight. The solid was collected by filtering, washing with water and Et$_2$O, and air drying to afford additional title compound.

Intermediate 1: Step c

6-Bromo-2,4-dichloro-3-phenylquinoline

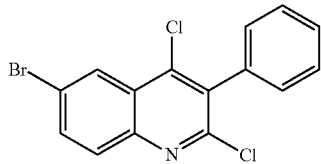 [SMILES: Clc1nc2ccc(Br)cc2c(Cl)c1-c1ccccc1]

A solution of 6-bromo-4-hydroxy-3-phenylquinolin-2 (1H)-one (8.50 g, 26.9 mmol. Intermediate 1: step b) in phosphoryl trichloride (51 mL, 547 mmol) was heated at 107° C. for 3.5 hours, and then cooled to room temperature. After evaporation of POCl$_3$ in vacuo, concentrated NH$_4$OH (aqueous) was added dropwise at 4° C. until pH 9. The precipitated solid was filtered, washed with water, and dried at 50° C. under vacuum overnight to provide the title compound.

The title compound was also prepared using the following procedure:

A mixture of 4-bromoaniline (10.0 g, 58.1 mmol), 2-phenylmalonic acid (11.0 g, 61.0 mmol), and phosphorus oxychloride (54.0 mL, 581 mmol) was heated in a 90° C. oil bath for 20 hours. The mixture was allowed to cool to room temperature and was diluted with CH$_2$Cl$_2$ in a large beaker (ca. 200 mL final volume). Ice (ca. 100 mL) was added and the mixture was stirred while monitoring the internal temperature; an ice bath was used to cool the mixture when the internal temperature reached 35° C. When the temperature of the mixture fell, the phases were separated and the aqueous phase was extracted once with CH$_2$Cl$_2$. The combined organic extracts were concentrated onto silica gel and the title compound was isolated by flash column chromatography (silica gel, 20-55% CH$_2$Cl$_2$-heptane).

Intermediate 2: Step a

Methyl 5-bromo-2-(2-(2-chlorophenyl acetamido)benzoate

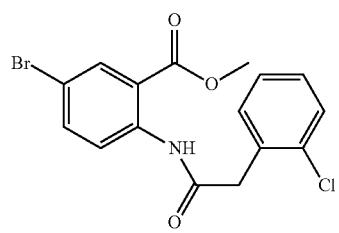 [SMILES: COC(=O)c1cc(Br)ccc1NC(=O)Cc1ccccc1Cl]

The title compound was prepared using 2-chlorophenylacetyl chloride in place of phenylacetyl chloride using the procedure described for Intermediate 1: step a.

Intermediate 2: Step b

6-Bromo-3-(2-chlorophenyl)-4-hydroxyquinolin-2 (1H)-one

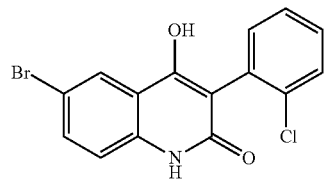 [SMILES: O=c1[nH]c2ccc(Br)cc2c(O)c1-c1ccccc1Cl]

The title compound was prepared using methyl 5-bromo-2-(2-(2-chlorophenyl)acetamido)benzoate (Intermediate 2: step a) in place of 5-bromo-2-(2-phenylacetamido)benzoate using the procedure described for Intermediate 1: step b.

Intermediate 2: Step c

6-Bromo-2,4-dichloro-3-(2-chlorophenyl)quinoline

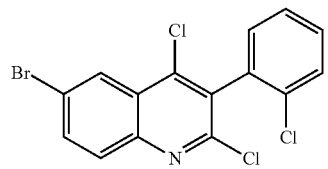 [SMILES: Clc1ccccc1-c1c(Cl)nc2ccc(Br)cc2c1Cl]

The title compound was prepared using 6-bromo-3-(2-chlorophenyl)-4-hydroxyquinolin-2(1H)-one (Intermediate 2: step b) in place of 6-bromo-4-hydroxy-3-phenylquinolin-2(1H)-one using the procedure described for Intermediate 1: step c.

Intermediate 3: Step a

6-Bromo-2,4-dichloro-8-methyl-3-phenylquinoline

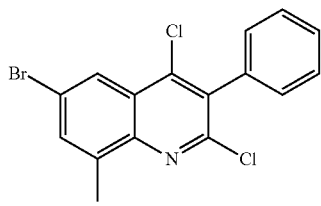 [SMILES: Cc1cc(Br)cc2c(Cl)c(-c3ccccc3)c(Cl)nc12]

A mixture of 2-phenylmalonic acid (7.62 g, 42.3 mmol) and POCl₃ (32.8 mL, 352 mmol) was stirred at reflux (130° C. aluminum block temp) for 10 minutes, and the resulting homogeneous yellow solution was cooled on an ice bath. 4-Bromo-2-methylaniline (6.56 g, 35.2 mmol) was added in one portion and the mixture was refluxed for 2 hours. The dark solution was allowed to cool to room temperature and was diluted with DCM (70 mL) and ice (100 mL), and stirred under ambient conditions for ~5-10 minutes at which point exothermic POCl₃ hydrolysis commenced (ice bath cooling), and was then stirred at room temperature for another 30 minutes. The light yellow aqueous layer was extracted with DCM (1×30 mL), and the combined dark homogeneous organic layers were dried (Na₂SO₄), filtered, and concentrated with silica gel. The silica-adsorbed residue was dry load flash chromatographed with a 20% DCM/heptane to 100% DCM gradient to provide the title compound as an off-white solid.

Intermediate 3: Step b 2,4-Dichloro-8-methyl-3-phenylquinoline-6-carbaldehyde

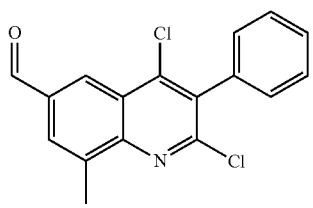 [SMILES: Cc1cc(C=O)cc2c(Cl)c(-c3ccccc3)c(Cl)nc12]

A −71° C. solution of n-BuLi (6.14 mL, 1.59 M in hexane, 9.77 mmol) under argon was treated with a solution of 6-bromo-2,4-dichloro-8-methyl-3-phenylquinoline (3.26 g, 8.81 mmol, Intermediate 3: step a) in THF (27 mL) as an intermittent fine stream over 28 minutes. After a few minutes, DMF (1.38 mL, 17.8 mmol) was added dropwise over 2 minutes to the reddish-brown reaction, and the resulting greenish-black mixture was stirred at −72° C. for 30 minutes. The reaction was removed from the cold bath and allowed to stir under ambient conditions for 10 minutes, and was then quenched in one portion with 5 M aqueous NH₄Cl (7 mL), partitioned with 4:1 EtOAc/heptane (50 mL) and 5:3 4 M aqueous NaCl/5 M aqueous NaBr (40 mL), and filtered. The filter cake was dissolved in 9:1 DCM/MeOH (15 mL), and this was combined with the clear yellow organic layer filtrate and dried (Na₂SO₄), filtered, and concentrated. The residue was dry load flash chromatographed with a 20% DCM/heptane to 100% DCM gradient to afford the title compound as a white solid.

Intermediate 4: Step a 5-(4-(1H-Pyrazol-1-yl)benzyl)-2,2-dimethyl-1,3-dioxane-4,6-dione

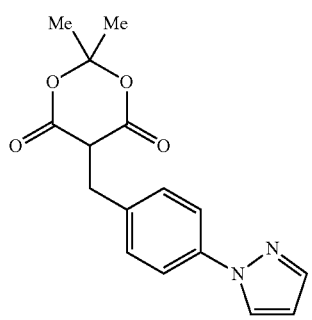 [SMILES: CC1(C)OC(=O)C(Cc2ccc(-n3cccn3)cc2)C(=O)O1]

L-Proline (4.07 g. 35.0 mmol) was added to a semi-heterogeneous mixture of 4-(H-pyrazol-1-yl)benzaldehyde (30.0 g, 174 mmol) and 2,2-dimethyl-1,3-dioxane-4,6-dione (25.6 g, 174 mmol) in ethanol (996 mL) at room temperature. After 40 minutes, diethyl 1,4-dihydro-2,6-dimethyl-3,5-pyridinedicarboxylate (44.1 g, 174 mmol) was added in one portion followed by ethanol (125 mL). After overnight stirring, the mixture was concentrated under reduced pressure to afford a yellow solid. Isopropanol (300 mL) was added and the heterogeneous mixture was sonicated for 30 minutes. The mixture was filtered and the filter cake was washed with isopropanol. The solids were collected and dried under vacuum to provide the title compound as a white solid.

Intermediate 4: Step b 2-(4-(1H-Pyrazol-1-yl)benzyl)malonic acid

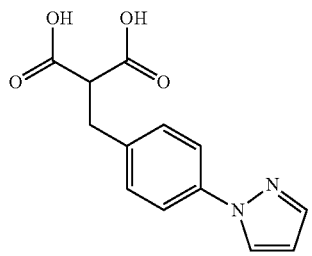 [SMILES: O=C(O)C(Cc1ccc(-n2cccn2)cc1)C(=O)O]

A mixture of 5-(4-(1H-pyrazol-1-yl)benzyl)-2,2-dimethyl-1,3-dioxane-4,6-dione (41.4 g, 137 mmol, Intermediate 4: step a) and 3 M aqueous NaOH solution (300 mL, 900 mmol) was heated for 48 hours at 110° C. The mixture was cooled to room temperature, diluted with water (200 mL) and extracted with EtOAc (1×100 mL). The aqueous layer was then acidified to pH 1 with concentrated aqueous HCl at 0° C. The resulting mixture was stirred at 0° C. for 1.5 hours, filtered and the filter cake was washed with water. The solids were collected and dried under vacuum at 40° C. to provide the title compound as a white solid.

Intermediate 4: Step c 3-(4-(1H-Pyrazol-1-yl)benzyl)-6-bromo-2,4-dichloroquinoline

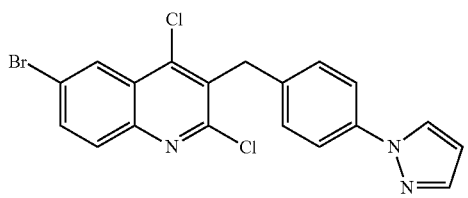 [SMILES: Clc1nc2ccc(Br)cc2c(Cl)c1Cc1ccc(-n2cccn2)cc1]

A mixture of 2-(4-(1H-pyrazol-1-yl)benzyl)malonic acid (3.37 g, 19.6 mmol, Intermediate 4: step b) and 4-bromoaniline (5.10 g, 19.6 mmol) in POCl$_3$ (18 mL) was heated at 105° C. for 3 hours, cooled to room temperature and evaporated in vacuo to remove excess POCl$_3$. The residue was poured into ice H$_2$O and treated with aqueous NH$_4$OH to pH 8-9 (temperature of the aqueous mixture was kept cold during addition). The precipitates were collected, rinsed with H$_2$O and dried under reduced pressure. After drying the resulting crude pale yellow solid was washed several times with Et$_2$O then acetonitrile and dried to provide the title compound as a pale yellow solid.

Intermediate 4: Step d 3-(4-(1H-Pyrazol-1-yl)benzyl)-6-bromo-4-chloro-2-methoxyquinoline

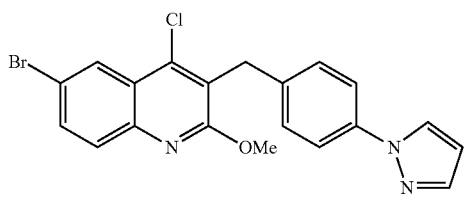 [SMILES: COc1nc2ccc(Br)cc2c(Cl)c1Cc1ccc(-n2cccn2)cc1]

A heterogeneous mixture of 3-(4-(1H-pyrazol-1-yl)benzyl)-6-bromo-2,4-dichloroquinoline (13.0 g, 30.0 mmol, Intermediate 4: step c), sodium methoxide (9.73 g, 180 mmol), and toluene (120 mL) was heated at 110° C. After 5.5 hours, the mixture was cooled to room temperature then filtered through Celite® rinsing with dichloromethane. The filtrate was concentrated to provide a crude yellow solid. The crude solid was purified by flash column chromatography (silica gel, 50% dichloromethane-hexanes initially, grading to 100% dichloromethane) to provide the title compound as a white solid.

Intermediate 5: Step a

Ethyl 3-oxo-2-(4-(trifluoromethyl)benzyl)pentanoate

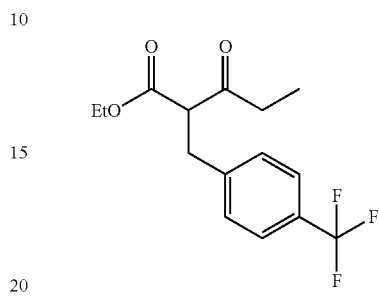

Sodium hydride (60% dispersion in mineral oil, 1.75 g, 43.7 mmol) was added in portions over 1 minute to an ice-cooled, stirring solution of ethyl 3-oxopentanoate (6.30 g, 43.7 mmol) in dry dimethoxyethane (87 mL). After 5 minutes, the flask was removed from the cooling bath and stirring continued at room temperature. After 30 minutes, a solution of 4-(trifluoromethyl)benzyl bromide (10.4 g, 43.7 mmol) in dry dimethoxyethane (10 mL) was added dropwise over 2 minutes. After 2.5 hours, ethyl acetate (300 mL) and water (100 mL) were added. The layers were separated. The organic layer was dried with sodium sulfate and the dried solution was filtered. The filtrate was concentrated and the residue was purified by flash-column chromatography on silica gel eluting with hexanes initially, grading to 50% dichloromethane-hexanes to provide the title compound as a colorless liquid.

Intermediate 5: Step b

6-Bromo-2-ethyl-3-(4-(trifluoromethyl)benzyl)quinolin-4-ol

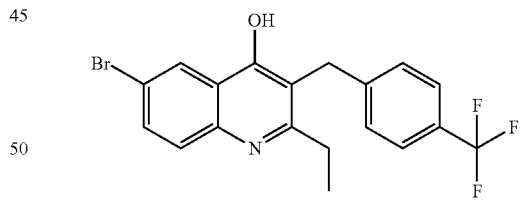

A round-bottomed flask equipped with a Dean-Stark apparatus was charged with ethyl 3-oxo-2-(4-(trifluoromethyl)benzyl)pentanoate (8.84 g, 29.2 mmol, Intermediate 5: step a), 4-bromoaniline (5.00 g, 29.2 mmol), para-toluenesulfonic acid (0.503 g, 2.9 mmol), and toluene (146 mL). The mixture was heated to 125° C. After 18 hours, the flask was cooled to room temperature. The toluene was removed by rotary evaporation to provide an amber colored solid. A mixture of the solid and diphenyl ether (29.1 mL) was heated to 220° C. After 70 minutes, the mixture was cooled to room temperature. Ether (100 mL) and hexanes (50 mL) were added. The mixture was allowed to stir for 30 minutes during which time a white solid crashed out of solution. The suspension was filtered through filter paper, rinsing with ether. The gummy solids were collected. Acetonitrile (20 mL) was added and the mixture was sonicated for 5 minutes. The slurry was filtered through filter paper and the solids were rinsed with acetonitrile. The off-white solids were collected, dried, and then used in the next step without further purification.

Intermediate 5: Step c

6-Bromo-4-chloro-2-ethyl-3-(4-(trifluoromethyl) benzyl)quinoline

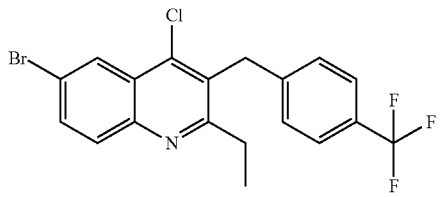 [SMILES: CCc1nc2ccc(Br)cc2c(Cl)c1Cc1ccc(C(F)(F)F)cc1]

A round-bottomed flask containing a mixture of 6-bromo-2-ethyl-3-(4-(trifluoromethyl)benzyl)quinolin-4-ol (4.00 g, 8.29 mmol, Intermediate 5: step b), phosphorous oxychloride (3.50 mL, 37.3 mmol) and acetonitrile (27 mL) was placed into a metal heating block at 90° C. After 65 minutes, the reaction mixture was cooled to room temperature. The acetonitrile and excess phosphorous oxychloride were removed by rotary evaporation. The residue was dissolved in dichloromethane (100 mL) and the solution was cooled in an ice-water bath. Ice (50 mL) was added. Concentrated aqueous ammonia solution was added dropwise until the pH=8-9 by litmus paper test. The biphasic mixture was separated and the aqueous layer was extracted with dichloromethane (50 mL). The combined organics were dried with sodium sulfate and the dried solution was filtered. Silica gel (8 g) was added to the filtrate and the solvents were removed by rotary evaporation to provide a free-flowing powder. The powder was loaded onto a silica gel column. Elution with hexanes initially, grading to 20% ethyl acetate-hexanes provided the title compound as an off-white solid.

Intermediate 6: Step a

Methyl 5-bromo-2-(3-phenylpropanamido)benzoate

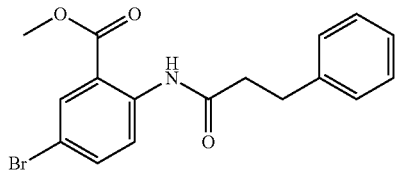 [SMILES: COC(=O)c1cc(Br)ccc1NC(=O)CCc1ccccc1]

Into a 100-mL round-bottom flask, was placed a solution of methyl 2-amino-5-bromobenzoate (5.0 g, 21.73 mmol), triethylamine (4.39 g, 43.38 mmol) and 3-phenylpropanoyl chloride (3.67 g, 21.76 mmol) in dichloromethane (50 mL). The resulting mixture was stirred for 12 hours at room temperature. The reaction was then quenched by the addition of 50 mL of water. The resulting mixture was extracted with 3×50 mL of dichloromethane. The combined organic layers were dried over anhydrous sodium sulfate, filtered and concentrated under vacuum. The residue was purified by chromatography over a silica gel column with ethyl acetate/petroleum ether (2:1) to provide the title compound as a white solid.

Intermediate 6: Step b

3-Benzyl-6-bromo-4-hydroxy-1,2-dihydroquinolin-2-one

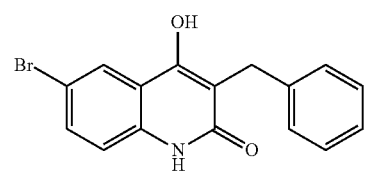 [SMILES: O=c1[nH]c2ccc(Br)cc2c(O)c1Cc1ccccc1]

Into a 50-mL round-bottom flask purged and maintained with an inert atmosphere of nitrogen, was placed a solution of methyl 5-bromo-2-(3-phenylpropanamido)benzoate (2.8 g, 7.8 mmol, Intermediate 6: step a) and KHMDS (47 mL, 15% in toluene) in tetrahydrofuran (50 mL). The resulting solution was stirred for 12 hours at room temperature. The reaction was then quenched by the addition of 2 mL of methanol and 10 mL of aqueous HCl (1 M). The resulting solution was extracted with 2×100 mL of ethyl acetate. The combined organic layers were dried over anhydrous sodium sulfate, filtered and concentrated under vacuum. The crude product was purified by re-crystallization from ethyl acetate to provide the title compound as a white solid.

Intermediate 6: Step c

3-Benzyl-6-bromo-2,4-dichloroquinoline

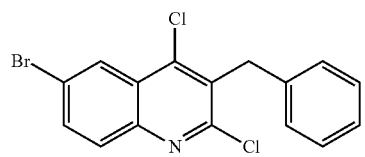 [SMILES: Clc1nc2ccc(Br)cc2c(Cl)c1Cc1ccccc1]

Into a 100-mL round-bottom flask, was placed a solution of 3-benzyl-6-bromo-4-hydroxy-1,2-dihydroquinolin-2-one (2.9 g, 8.78 mmol, Intermediate 6: step b) in POCl₃ (20 mL). The resulting solution was stirred for 1 hour at 110° C. The reaction was then quenched by the addition of 50 mL of water/ice. The pH value of the solution was adjusted to 7-8 with aqueous ammonia. The resulting solution was extracted with 3×50 mL of ethyl acetate. The combined organic layers were dried over anhydrous sodium sulfate, filtered and concentrated under vacuum. The residue was purified by chromatography over a silica gel column with ethyl acetate/petroleum ether (2:1) to provide the title compound as a white solid.

Intermediate 7: Step a 5-(4-Fluorobenzyl)-2,2-dimethyl-1,3-dioxane-4,6-dione

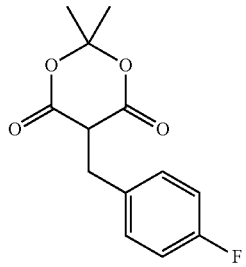 [SMILES: CC1(C)OC(=O)C(Cc2ccc(F)cc2)C(=O)O1]

Proline (5.748 g, 49.42 mmol) was added to a solution of 4-fluorobenzaldehyde (24.99 g, 197.3 mmol) and Meldrum's acid (29.01 g, 197.3 mmol) in EtOH (900 mL). The mixture was stirred at room temperature for 1.5 hours, then diethyl 1,4-dihydro-2,6-dimethyl-3,5-pyridinedicarboxylate (50.99 g, 197.3 mmol) was added along with an additional 100 mL of EtOH. The mixture was stirred overnight and EtOH was removed under reduced pressure. The residue was triturated with i-PrOH and filtered to provide the title compound as a white solid.

Intermediate 7: Step b 2-(4-Fluorobenzyl)malonic acid

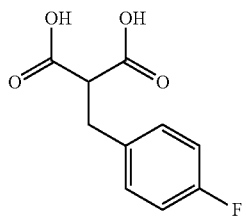 [SMILES: O=C(O)C(Cc1ccc(F)cc1)C(=O)O]

A solution of 5-(4-fluorobenzyl)-2,2-dimethyl-1,3-dioxane-4,6-dione (34.118 g, 135.26 mmol, Intermediate 7: step a) and 6 M aqueous NaOH (136 mL) was heated to 120° C. under a reflux condenser and positive pressure of nitrogen for two days. The mixture was allowed to cool to room temperature, water and ethyl acetate were added, and the layers were separated. The aqueous layer was acidified to pH 0 with 6 M aqueous HCl and the mixture was stirred at room temperature for 30 minutes. Dichloromethane was added to the mixture, the organic layer was separated, and the aqueous layer was extracted with excess ethyl acetate. The combined organic layers were dried (Na$_2$SO$_4$), filtered, and concentrated to dryness to provide the title compound.

Intermediate 7: Step c

6-Bromo-2,4-dichloro-3-(4-fluorobenzyl)quinoline

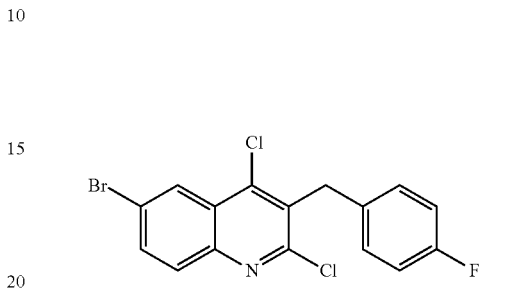

A mixture of 2-(4-fluorobenzyl)malonic acid (25.75 g, 112.9 mmol, Intermediate 7: step b) and 4-bromoaniline (19.43 g, 112.9 mmol) in POCl$_3$ (106 mL, 1129 mmol) was heated at 105° C. for 3 hours, then 80° C. overnight under a reflux condenser and positive pressure of nitrogen. The solution was allowed to cool to room temperature and was slowly poured in portions into a flask of room temperature water that was placed in a water bath. Ice was added as necessary to regulate the exotherm. The mixture was basified to pH 10 with concentrated aqueous NH$_4$OH. Dichloromethane was added, and without shaking, the organic layer was separated from the aqueous layer. The aqueous layer was further extracted with dichloromethane. The combined organic layers were dried over Na$_2$SO$_4$, filtered and concentrated to dryness. The crude material was triturated with acetonitrile, filtered, and dried in a high vacuum oven to provide the title compound.

Intermediate 7: Step d

6-Bromo-4-chloro-3-(4-fluorobenzyl)-2-methoxyquinoline

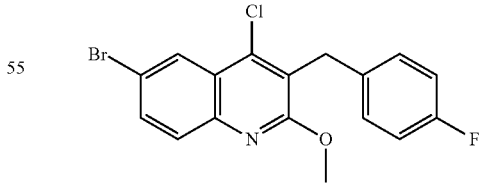

A mixture of 6-bromo-2,4-dichloro-3-(4-fluorobenzyl)quinoline (1.000 g, 2.597 mmol, Intermediate 7: step c) and sodium methoxide (0.732 g, 13.15 mmol) in toluene (13 mL) was heated to 105° C. under a reflux condenser and positive pressure of nitrogen overnight. The mixture was allowed to cool to room temperature, filtered through Celite®, and rinsed with dichloromethane. The filtrate was concentrated to dryness to provide the title compound which was used without further purification.

Intermediate 8: Step a

6-Bromo-4-hydroxyquinolin-2(1H)-one

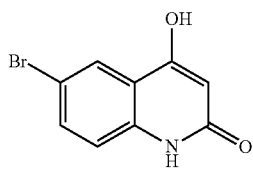

According to the general method described in Synthetic Communications 2010, 40, 732, a mixture of 4-bromoaniline (30.0 g, 174 mmol) and 2,2-dimethyl-1,3-dioxan-4,6-dione (25.1 g, 174 mmol) was heated to 80° C. for 1.5 hours and cooled to ambient temperature to receive 3-((4-bromophenyl) amino)-3-oxopropanoic acid. The acetone byproduct was removed under vacuum to provide the intermediate product as a dry solid. Eaton's reagent (100 mL) was added to the solid and the resulting mixture heated to 70° C. overnight then cooled to room temperature. The mixture was poured into water and the brown precipitate was filtered and rinsed with water. The brown precipitate was triturated with ethanol, then filtered to provide the title compound as a light brown solid.

Intermediate 8: Step b

6-Bromo-2,4-dichloroquinoline

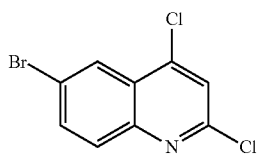 [SMILES: Clc1cc(Cl)c2cc(Br)ccc2n1]

A solution of 6-bromo-4-hydroxyquinolin-2(1H)-one (18.0 g, 75.1 mmol, Intermediate 8: step a) and POCl$_3$ (84 mL) was heated at 105° C. overnight. The solution was cooled to room temperature, then slowly poured portion-wise into a water bath, adding ice as needed to regulate the exotherm. Concentrated aqueous ammonium hydroxide was added to basify the mixture to pH 9-10. The solids that precipitated were filtered, rinsed with water and dried to provide the title compound as a brown solid.

Intermediate 8: Step c 4-((6-Bromo-2,4-dichloroquinolin-3-yl)methyl)benzonitrile

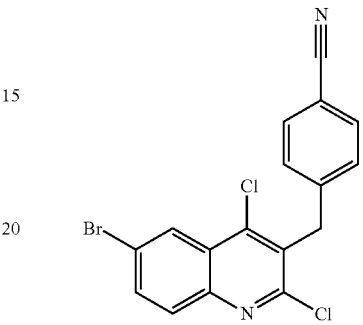

To a solution of diisopropylamine (1.40 mL, 9.96 mmol) in THF (12 mL) cooled to 0° C. was added n-butyllithium (2.5 M solution in hexanes, 3.80 mL, 9.50 mmol) dropwise via syringe. The reaction mixture was stirred at 0° C. for 10 minutes then cooled to −78° C. at which time a separate solution of 6-bromo-2,4-dichloroquinoline (1.80 g, 6.51 mmol, Intermediate 8: step b) in THF (29 mL) was added dropwise via syringe. The mixture was stirred at −78° C. for 30 minutes followed by the addition of 4-(bromomethyl) benzonitrile (1.52 g, 7.74 mmol) in THF (5 mL). After an additional 10 minutes of stirring at −78° C., the reaction was transferred to an ice bath and warmed to ambient temperature over 5 hours. The reaction was quenched with water and the aqueous phase was extracted with DCM. The organic phase was dried (Na$_2$SO$_4$), filtered, and concentrated. The crude product was purified by flash column chromatography (silica gel, 0-5% EtOAc-hexanes) to provide the title compound as a white solid.

Intermediate 8: Step d 4-((6-Bromo-4-chloro-2-methoxyquinolin-3-yl)methyl)benzonitrile

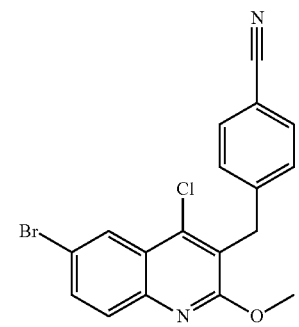 [SMILES: COc1nc2ccc(Br)cc2c(Cl)c1Cc1ccc(C#N)cc1]

A heterogeneous mixture of 4-((6-bromo-2,4-dichloroquinolin-3-yl)methyl)benzonitrile (650 mg, 1.16 mmol, Intermediate 8: step c) and sodium methoxide (314 mg, 5.81 mmol) in dry toluene (2.2 mL) was heated at 105° C. After 9 hours, the mixture was cooled to ambient temperature and filtered through Celite®, rinsing with DCM. The filtrate was concentrated and the crude was purified by flash column chromatography (silica gel, 0-5% EtOAc-hexanes) to provide the title compound as a white solid.

Intermediate 9: Step a

6-Bromo-3-((6-(trifluoromethyl)pyridin-3-yl)methyl) quinoline-2,4-diol

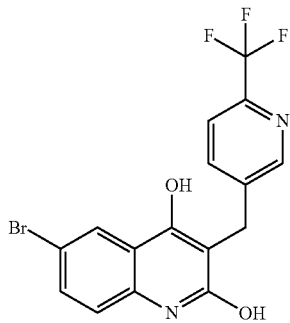 [SMILES: Oc1nc2ccc(Br)cc2c(O)c1Cc1ccc(C(F)(F)F)nc1]

6-Bromo-4-hydroxyquinolin-2(1H)-one (3.2 g, 18.3 mmol, Intermediate 8: step a), 6-(trifluoromethyl)nicotinaldehyde (4.0 g, 16.7 mmol), and diethyl 2,6-dimethyl-1,4-dihydropyridine-3,5-dicarboxylate (4.2 g, 16.7 mmol), in pyridine (34 mL) were heated to 105° C. for 3 hours. The solution was allowed to cool to ambient temperature, resulting in the formation of a solid. Minimal isopropanol was added to the mixture and the slurry was stirred for 1 hour, sonicated, and filtered. The filtered solids were rinsed with isopropanol and dried under continuous air flow to provide the title compound as an off-white solid. Additional product was recrystallized from the filtrate, filtered, and rinsed with isopropanol.

Intermediate 9: Step b

6-Bromo-2,4-dichloro-3-((6-(trifluoromethyl)pyridin-3-yl)methyl)quinoline

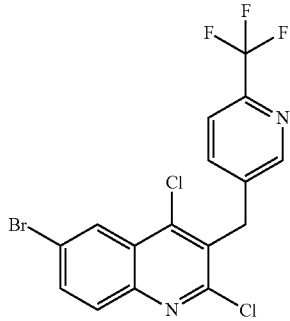 [SMILES: FC(F)(F)c1ccc(Cc2c(Cl)nc3ccc(Br)cc3c2Cl)cn1]

POCl$_3$ (1.5 mL) was added to a mixture of 6-bromo-3-((6-(trifluoromethyl)pyridin-3-yl)methyl)quinoline-2,4-diol (1.8 g, 4.6 mmol, Intermediate 9: step a) in acetonitrile (23 mL). The mixture was heated to 80° C. and refluxed overnight, forming an amber-colored solution. The solution was allowed to cool to ambient temperature and was quenched with water, resulting in the formation of a precipitate. Concentrated ammonium hydroxide was added to the suspension to attain pH 9-10, then the slurry was stirred for 1 hour. The solids were filtered then washed with 50:50 acetonitrile/water, followed by additional water, and dried in a high vacuum oven to provide the title compound.

Intermediate 9: Step c

6-Bromo-4-chloro-2-methoxy-3-((6-(trifluoromethyl)pyridin-3-yl)methyl)quinoline

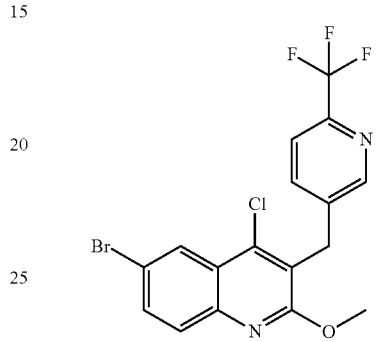

A mixture of 6-bromo-2,4-dichloro-3-((6-(trifluoromethyl)pyridin-3-yl)methyl)quinoline (1.0 g, 2.3 mmol, Intermediate 9: step b) and sodium methoxide (1.2 g, 22 mmol) in dry toluene (12 mL) was heated to 80° C. under a positive pressure of nitrogen overnight. The mixture was allowed to cool to ambient temperature. Aqueous saturated sodium bicarbonate solution was added to the mixture and the layers were separated. The aqueous layer was extracted with ethyl acetate. The combined organic layers were dried over sodium sulfate, filtered, and concentrated to dryness. The crude material was purified by flash column chromatography (silica gel, 0-20% EtOAc-hexane) to provide the title compound as a white solid.

Intermediate 10: Step a 2,2-Dimethyl-5-(4-(trifluoromethyl)benzyl)-1,3-dioxane-4,6-dione

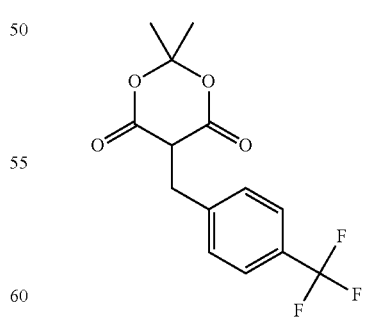

Similar procedures to those referenced in Tett. Lett. (2006), 651, D. Ramachary; Eur. J. Org. Chem. (2008), 975, D. Ramachary were employed. To a 5 L 3-necked flask fitted with an overhead mechanical stirrer was added 4-(trifluoromethyl)benzaldehyde (43.5 g, 250 mmol) followed by the addition of anhydrous EtOH (3,000 mL), Meldrum's acid (37.5 g, 260 mmol), diethyl 2,6-dimethyl-1,4-dihydropyridine-3,5-dicarboxylate (67.5 g, 266 mmol) and L-proline (6.0 g, 51 mmol) at room temperature. The yellowish reaction mixture was stirred at room temperature under N₂. An aliquot was removed after 4 hours and rinsed with EtOH and then Et₂O, and air dried. The ¹H NMR of this aliquot showed the reaction to be complete. The full reaction was stopped and the white precipitate from the reaction was collected by filtration and rinsed with EtOH and then Et₂O and dried under vacuum to provide the title compound in the first crop as a fine white solid. The yellowish mother liquors were concentrated and allowed to crystallize overnight from EtOH and the solid material was collected as before to provide the title compound.

Intermediate 10: Step b 2-(4-(Trifluoromethyl)benzyl)malonic acid

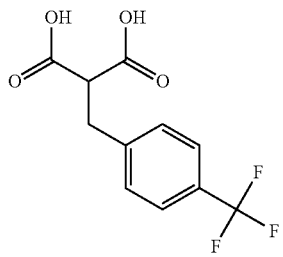 [SMILES: O=C(O)C(Cc1ccc(C(F)(F)F)cc1)C(=O)O]

To a 2 L flask containing 2,2-dimethyl-5-(4-(trifluoromethyl)benzyl)-1,3-dioxane-4,6-dione (65 g, 215 mmol, Intermediate 10: step a) was added a TFA/water solution (v/v, 560 mL/280 mL) at room temperature and the white suspension was heated between 70° C. and 78° C. in a large oil bath. The suspension did not dissolve until a temperature of 72° C. was reached. After approximately 40 minutes, the suspension became a clear homogeneous solution. After 3 hours. HPLC indicated that the reaction was complete. The mixture was concentrated on the rotary evaporator and azeotroped with toluene (4×100 mL) to afford the title compound as a white solid which was used without further purification.

Intermediate 10: Step c

6-Bromo-2,4-dichloro-3-(4-(trifluoromethyl)benzyl)quinoline

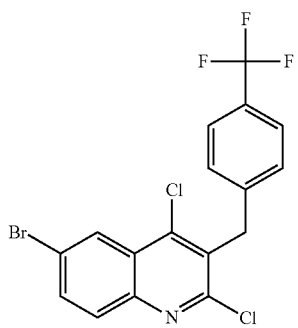 [SMILES: FC(F)(F)c1ccc(Cc2c(Cl)nc3ccc(Br)cc3c2Cl)cc1]

To a 500 mL 3-necked flask fitted with a reflux condenser and Drierite® drying tube, was added POCl₃ (190 mL), 2-(4-(trifluoromethyl)benzyl)malonic acid (28.5 g, 109 mmol, Intermediate 10: step b) and 4-bromoaniline (19 g, 110 mmol) at room temperature. The heterogeneous mixture was heated in an aluminum mantle to 100° C., which resulted in a light amber homogenous solution after approximately 10 minutes. The reaction was stirred at 110° C. for 6.5 hours, after which removal of an aliquot and TLC (20% hexane-DCM) showed the reaction to be complete. The contents were transferred to a 1 L single-necked round bottom flask and the POCl₃ was removed by evaporation. The resulting dark brown material was then poured onto ice chips (~500 g) in a 2 L Erlenmeyer flask pre-cooled to 0° C. DCM (~500 mL) was added and the solution was stirred at 0° C. as a solution of 6 M aqueous KOH (~500 mL) was added carefully. 5 N aqueous NH₄OH (~100 mL) was also added to bring the pH to ~8-9. The neutralization process was kept at 0° C. throughout. More DCM was added and the organic phase was separated. The aqueous portion was washed with DCM (3×250 mL) and the combined organics were washed with brine, dried over Na₂SO₄, filtered and concentrated to provide a brown solid. The crude solid was triturated with CH₃CN to provide the title compound as a white fluffy solid after filtration.

Intermediate 10: Step d

6-Bromo-4-chloro-2-methoxy-3-(4-(trifluoromethyl)benzyl)quinoline

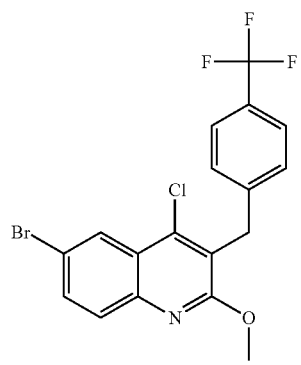 [SMILES: COc1nc2ccc(Br)cc2c(Cl)c1Cc1ccc(C(F)(F)F)cc1]

To a 1 L flask containing 6-bromo-2,4-dichloro-3-(4-(trifluoromethyl)benzyl)quinoline (32.5 g, 74.7 mmol, Intermediate 10: step c) was added toluene (550 mL) followed by solid sodium methoxide (40 g, 740 mmol, 97% purity) at room temperature. The suspension was stirred at reflux (~118° C.) in an aluminum mantle. TLC (50% hexane-DCM) and HPLC after 5.5 hours showed the reaction to be complete. The reaction mixture was filtered through Celite® while still warm (~80° C.) and rinsed with warm toluene (~70° C., 500 mL). The colorless filtrate was concentrated which then solidified to provide the title compound as an off white solid.

Intermediate 11: Step a tert-Butyl 4-((4-chloro-2-methoxy-3-(4-(trifluoromethyl)benzyl)quinolin-6-yl)(hydroxy)methyl)piperidine-1-carboxylate

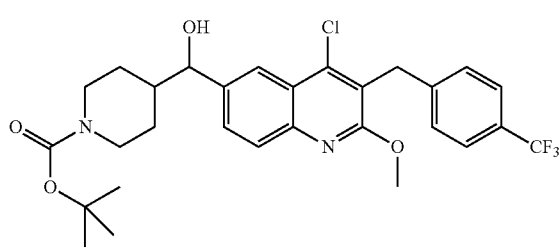 [SMILES: COc1nc2ccc(C(O)C3CCN(C(=O)OC(C)(C)C)CC3)cc2c(Cl)c1Cc1ccc(C(F)(F)F)cc1]

To a solution of 6-bromo-4-chloro-2-methoxy-3-(4-(trifluoromethyl)benzyl)quinoline (275 mg, 0.64 mmol, Intermediate 10: step d) in THF (8.75 mL) at −78° C. was added n-BuLi (1.6 M in hexanes, 519 μL, 0.83 mmol). The resulting solution was stirred at −78° C. for 5 minutes. Then, this mixture was cannulated over 20 minutes into a solution of tert-butyl 4-formylpiperidine-1-carboxylate (177 mg, 0.83 mmol) in THF (4 mL) at −78° C. The resulting mixture was stirred at −78° C. for 20 minutes then at 0° C. for 30 minutes. The reaction was then quenched with water and extracted with EtOAc. The organics were combined, dried (MgSO$_4$), filtered and concentrated to dryness. The residue was purified by FCC (0-30% EtOAc/heptane) to provide the title compound.

Intermediate 11: Step b (4-Chloro-2-methoxy-3-(4-(trifluoromethyl)benzyl)quinolin-6-yl)(piperidin-4-yl)methanol

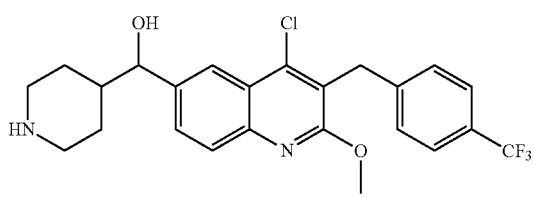 [SMILES: COc1nc2ccc(C(O)C3CCNCC3)cc2c(Cl)c1Cc1ccc(C(F)(F)F)cc1]

To a solution of tert-butyl 4-((4-chloro-2-methoxy-3-(4-(trifluoromethyl)benzyl)quinolin-6-yl)(hydroxy)methyl)piperidine-1-carboxylate (110 mg, 0.19 mmol, Intermediate 11: step a) in DCM (5 mL) was added TFA (75 μL, 0.97 mmol). The resulting solution was stirred at room temperature for 2 hours. TFA (75 μL, 0.97 mmol) was added and the mixture stirred at room temperature overnight. Then the reaction was diluted with DCM, cooled to 0° C., and the pH adjusted to ~pH 8 by the addition of 3 N aqueous NaOH dropwise. The layers were separated and the organics dried (MgSO$_4$), filtered and concentrated to dryness to afford the title compound which was used without further purification.

Intermediate 12: Step a 5-(4-Methylsulfonylbenzyl)-2,2-dimethyl-1,3-dioxane-4,6-dione

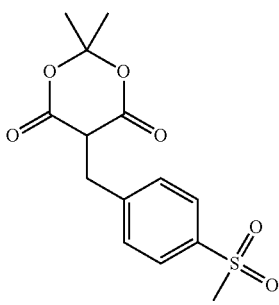 [SMILES: CC1(C)OC(=O)C(Cc2ccc(S(C)(=O)=O)cc2)C(=O)O1]

Proline (0.126 g, 1.086 mmol) was added to a solution of 4-(methylsulfonyl)benzaldehyde (1.00 g, 5.428 mmol) and Meldrum's acid (1.38 g, 5.428 mmol) in EtOH (10 mL). The mixture was stirred at room temperature for 1 hour and diethyl 1,4-dihydro-2,6-dimethyl-3,5-pyridinedicarboxylate (1.38 g, 5.428 mmol) was added. Stirring was continued for 3 hours and EtOH removed under reduced pressure. The residue was diluted with i-PrOH and filtered to provide the title compound as a white solid.

Intermediate 12: Step b 2-(4-Methylsulfonylbenzyl)malonic acid

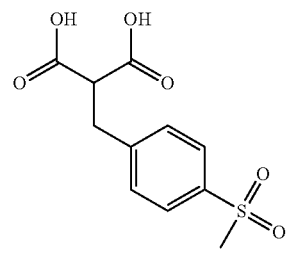 [SMILES: CS(=O)(=O)c1ccc(CC(C(=O)O)C(=O)O)cc1]

A solution of 5-(4-methylsulfonylbenzyl)-2,2-dimethyl-1,3-dioxane-4,6-dione (1.50 g, 4.802 mmol, Intermediate 12: step a) and 3 M aqueous NaOH (16 mL) was heated in the microwave at 75 W for 20 minutes at 120° C. The aqueous mixture was extracted with EtOAc (1×). The aqueous layer was acidified to pH 1 with concentrated aqueous HCl and extracted with EtOAc (2×). The combined EtOAc extracts were washed with H₂O, and brine, dried over Na₂SO₄, filtered and evaporated to dryness to afford the title compound as a white solid.

Intermediate 13: Step a

N-Methoxy-N,3-dimethyl-4-nitrobenzamide

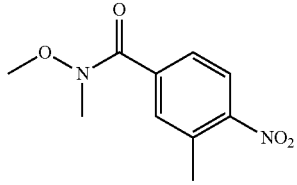 [SMILES: CON(C)C(=O)c1ccc([N+](=O)[O-])c(C)c1]

Triethylamine (7.6 mL, 54.65 mmol) was added slowly to a mixture of 3-methyl-4-nitrobenzoic acid (5 g, 27.33 mmol), N,O-dimethylhydroxylamine hydrochloride (2.99 g, 30.06 mmol), and EDCI (6.28 g, 32.79 mmol) in DCM (30 mL). The mixture was stirred at room temperature overnight, quenched with saturated aqueous NaHCO₃ and stirred at room temperature for 30 minutes. Water (50 mL) was added followed by additional DCM. The mixture was stirred for 10 minutes and layers were separated. The aqueous layer was again extracted with DCM. The combined organic layer was dried over Na₂SO₄, then filtered. The solvent was removed and the residual oil chromatographed (DCM/EtOAc) to provide the title compound as a white solid.

Intermediate 13: Step b (1-Methyl-1H-imidazol-5-yl)(3-methyl-4-nitrophenyl)methanone

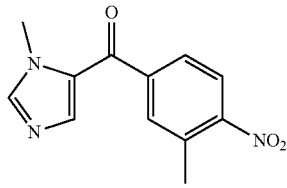 [SMILES: Cc1cc(C(=O)c2cncn2C)ccc1[N+](=O)[O-]]

A solution of EtMgBr (3.0 M in diethylether, 8.5 mL, 25.69 mmol) was added dropwise, over a 25 minute period to a solution of 5-bromo-1-methyl-1H-imidazole (4.1 g, 25.69 mmol) in dry DCM (25 mL). The mixture was stirred at room temperature for 15 minutes, cooled in an ice-brine bath and N-methoxy-N,3-dimethyl-4-nitrobenzamide (4.8 g, 21.41 mmol. Intermediate 13: step a) dissolved in 10 mL of DCM was added dropwise. A dark brown solid mass formed. The ice bath was removed and the mixture stirred at room temperature for 48 hours. Water was added to the suspension followed by 6 M aqueous HCl slowly to neutralize the mixture (pH=6-7). More DCM was added and the layers were separated. The organic layer was dried over Na₂SO₄, filtered and concentrated. Et₂O was added, the slurry sonicated, and the precipitates filtered to provide the title compound as a tan solid.

Intermediate 13: Step c (4-Amino-3-methylphenyl)(1-methyl-1H-imidazol-5-yl)methanone

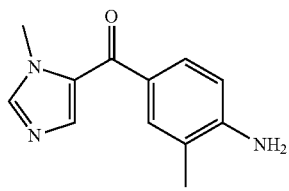 [SMILES: Cc1cc(C(=O)c2cncn2C)ccc1N]

A mixture of (1-methyl-1H-imidazol-5-yl)(3-methyl-4-nitrophenyl)methanone (3.3 g, 13.46 mmol, Intermediate 13: step b) and tin(II)chloride dihydrate (15.6 g, 67.28 mmol) in EtOH (80 mL) was stirred at reflux for 1 hour, cooled to room temperature overnight and evaporated in vacuo to remove most of the EtOH. The residue was poured into a 3 M aqueous NaOH/ice solution rinsing with EtOAc. The mixture was stirred at room temperature for 15 minutes and layers were separated. The aqueous layer was again extracted with EtOAc. The combined EtOAc extracts were washed with brine, dried (Na₂SO₄), filtered, and evaporated in vacuo to provide the crude product. The tan solid title compound was precipitated from Et₂O, collected by filtration and dried.

Intermediate 13: Step d (2,4-Dichloro-8-methyl-3-(4-(methylsulfonyl)benzyl)quinolin-6-yl)(1-methyl-1H-imidazol-5-yl)methanone

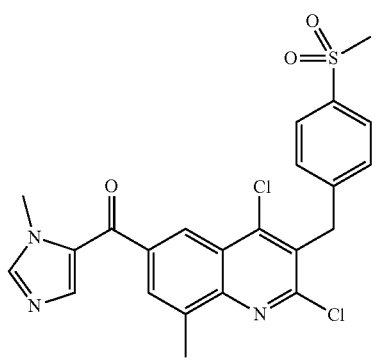 [SMILES: Cc1cc(C(=O)c2cncn2C)cc2c(Cl)c(Cc3ccc(S(C)(=O)=O)cc3)c(Cl)nc12]

A heterogeneous mixture of (4-amino-3-methylphenyl)(1-methyl-1H-imidazol-5-yl)methanone (0.8 g, 3.717 mmol, Intermediate 13: step c), 2-(4-methylsulfonylbenzyl)malonic acid (1.0 g, 3.717 mmol, Intermediate 12: step b) and POCl₃ (10 mL) was heated at 105° C. for 4 hours then cooled to room temperature and concentrated. Ice water was added to the residue and the mixture was treated with aqueous NH₄OH (kept adding ice during addition) to a basic pH 8-9. The mixture was stirred for 2 hours and filtered to provide a crude tan solid. The crude solids were dried completely, rinsed with Et₂O and dried under reduced pressure. The solids were diluted with DCM and filtered, rinsing several times. The filtrate was evaporated to dryness and the product precipitated with MeOH, filtered and dried to provide the title compound as a tan solid.

Intermediate 13: Step e (4-Chloro-2-methoxy-8-methyl-3-(4-(methylsulfonyl)benzyl)quinolin-6-yl)(1-methyl-1H-imidazol-5-yl)methanone

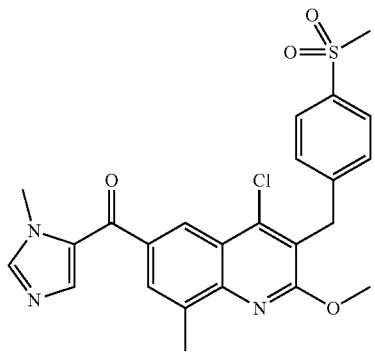 [SMILES: COc1nc2c(C)cc(C(=O)c3cncn3C)cc2c(Cl)c1Cc1ccc(S(C)(=O)=O)cc1]

A mixture of (2,4-dichloro-8-methyl-3-(4-(methylsulfonyl)benzyl)quinolin-6-yl)(1-methyl-1H-imidazol-5-yl)methanone (1.1 g, 2.15 mmol, Intermediate 13: step d) and dry sodium methoxide (0.58 g, 10.75 mmol) in toluene (10 mL) was heated in a sealed tube at 110° C. for 12 hours. The mixture was cooled to room temperature, diluted with DCM, stirred for 30 minutes at room temperature and the resulting suspension filtered through Celite®, rinsing several times with DCM. The solvents were removed under reduced pressure and the residue chromatographed (DCM/10% MeOH in DCM, gradient) to provide the title compound as a white solid after recrystallization from MeOH and drying under reduced pressure overnight.

Intermediate 14: Step a (3-(4-(1H-Pyrazol-1-yl)benzyl)-2,4-dichloro-8-methylquinolin-6-yl)(1-methyl-1H-imidazol-5-yl)methanone

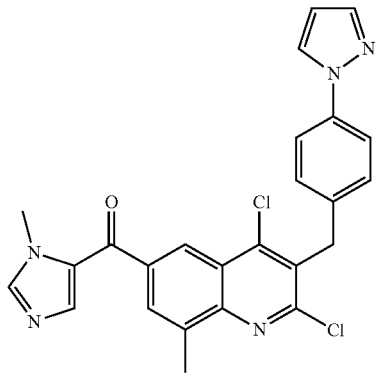 [SMILES: Cc1cc(C(=O)c2cncn2C)cc2c(Cl)c(Cc3ccc(-n4cccn4)cc3)c(Cl)nc12]

A heterogeneous mixture of 2-(4-(1H-pyrazol-1-yl)benzyl)malonic acid (2.42 g 9.29 mmol, Intermediate 4: step b), (4-amino-3-methylphenyl)(1-methyl-1H-imidazol-5-yl)methanone (2 g, 9.29 mmol, Intermediate 13: step c) and POCl$_3$ (10 mL) was heated at 105° C. for 4 hours. The mixture was cooled to room temperature, concentrated to remove excess POCl$_3$ and ice water was added. The mixture was treated with NH$_4$OH (kept adding ice during addition) to a basic pH 8-9 and the aqueous was then extracted with DCM. The DCM extracts were dried (Na$_2$SO$_4$), evaporated in vacuo and chromatographed (DCM/EtOAc, gradient) to provide the crude product. Pure product was precipitated with MeOH, filtered and dried to provide the title compound as a yellow solid.

Intermediate 14: Step b (3-(4-(1H-Pyrazol-1-yl)benzyl)-4-chloro-2-methoxy-8-methylquinolin-6-yl)(1-methyl-1H-imidazol-5-yl)methanone

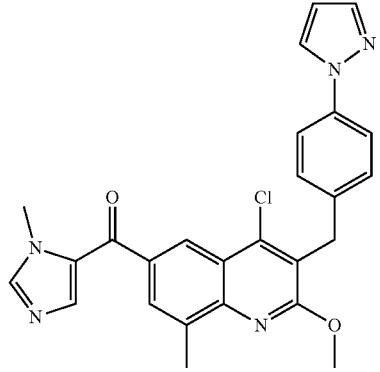 [SMILES: COc1nc2c(C)cc(C(=O)c3cncn3C)cc2c(Cl)c1Cc1ccc(-n2cccn2)cc1]

A mixture of (3-(4-(1H-pyrazol-1-yl)benzyl)-2,4-dichloro-8-methylquinolin-6-yl)(1-methyl-1H-imidazol-5-yl)methanone (1.05 g, 2.20 mmol, Intermediate 14: step a) and dry sodium methoxide (0.59 g, 11.02 mmol) in toluene (10 mL) was heated in a sealed tube at 110° C. for 12 hours. The mixture was cooled to room temperature, diluted with DCM, stirred for 30 minutes at room temperature and the resulting suspension filtered through Celite®, rinsing several times with DCM. The solvents were removed under reduced pressure and the residue chromatographed (DCM/10% MeOH in DCM, gradient) to provide the crude product.

Recrystallization from MeOH, filtering and drying under reduced pressure overnight provided the title compound.

Intermediate 15: Step a 2,2-Dimethyl-5-(3-(trifluoromethyl benzyl)-1,3-dioxane-4,6-dione

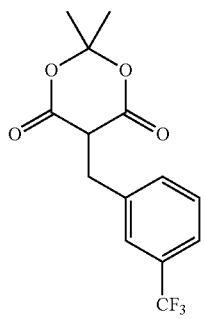 [SMILES: CC1(C)OC(=O)C(Cc2cccc(C(F)(F)F)c2)C(=O)O1]

Proline (0.52 g, 4.507 mmol) was added to a solution of 3-trifluoromethylbenzaldehyde (3 mL, 22.54 mmol) and Meldrum's acid (3.25 g, 22.54 mmol) in EtOH (50 mL). The mixture was stirred at room temperature for 3 hours and then diethyl 1,4-dihydro-2,6-dimethyl-3,5-pyridinedicarboxylate (5.71 g, 22.54 mmol) was added. Stirring was continued overnight and then the precipitate was isolated by filtration, rinsing with i-PrOH to provide the title compound.

Intermediate 15: Step b 2-(3-(Trifluoromethyl)benzyl)malonic acid

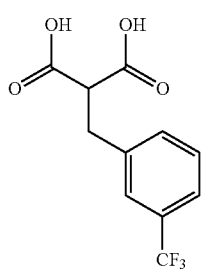 [SMILES: O=C(O)C(Cc1cccc(C(F)(F)F)c1)C(=O)O]

A solution of 2,2-dimethyl-5-(3-(trifluoromethyl)benzyl)-1,3-dioxane-4,6-dione (4.0 g, 13.23 mmol, Intermediate 15: step a) in 40% aqueous NaOH (20 mL) was heated in a 93° C. oil bath for 48 hours. The mixture was then cooled to room temperature and extracted with EtOAc. The aqueous layer was acidified to pH 2 with 6 N aqueous HCl then extracted with EtOAc (2×). The combined EtOAc extracts were washed with $H_2O$ followed by brine and dried over $Na_2SO_4$. The mixture was filtered, solvent was removed under reduced pressure and crude product purified by chromatography (10% MeOH/0.2% HOAc mixture in DCM) to afford the title compound as an off-white solid.

Intermediate 15: Step c (2,4-Dichloro-8-methyl-3-(3-(trifluoromethyl)benzyl)quinolin-6-yl)(1-methyl-1H-imidazol-5-yl)methanone

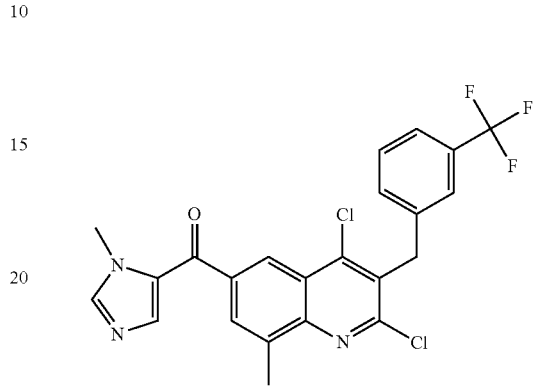

A heterogeneous mixture of (4-amino-3-methylphenyl)(1-methyl-1H-imidazol-5-yl)methanone (1.3 g, 6.04 mmol, Intermediate 13: step c), 2-(3-(trifluoromethyl)benzyl)malonic acid (2.06 g, 7.85 mmol, Intermediate 15: step b) and $POCl_3$ (10 mL) was heated at 105° C. for 4 hours. The mixture was cooled to room temperature and concentrated to remove excess $POCl_3$. Ice water was then added and the mixture treated with aqueous $NH_4OH$ (kept adding ice during addition) to a basic pH 8-9. The aqueous mixture was extracted with EtOAc (2×). The EtOAc extracts were dried over $Na_2SO_4$, evaporated in vacuo and chromatographed (DCM/EtOAc, gradient) to provide the title compound as an off-white solid.

Intermediate 15: Step d (4-Chloro-2-methoxy-8-methyl-3-(3-(trifluoromethyl)benzyl)quinolin-6-yl(1-methyl-1H-Imidazol-5-yl)methanone

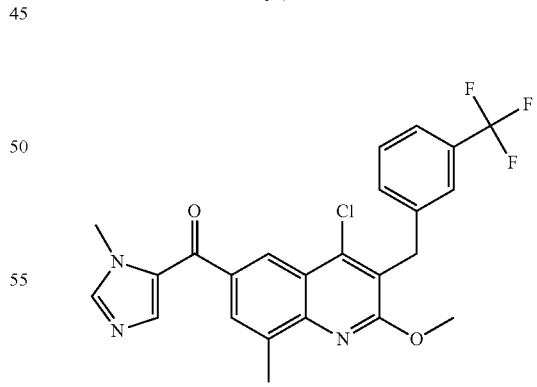

A mixture of (2,4-dichloro-8-methyl-3-(3-(trifluoromethyl)benzyl)quinolin-6-yl)(1-methyl-1H-imidazol-5-yl) methanone (0.87 g, 1.83 mmol, Intermediate 15: step c) and dry sodium methoxide (0.58 g, 10.75 mmol) in toluene was heated in a sealed tube at 110° C. for 12 hours. Starting material was still present, therefore additional $NaOCH_3$ (198 mg, 3.66 mmol) was added and stirring was continued at 110°

C. for another 24 hours. The mixture was then cooled to room temperature, diluted with DCM, stirred at room temperature for 30 minutes, and the resulting suspension filtered through Celite®, rinsing several times with DCM. The solvents were removed under reduced pressure and the white solid product was precipitated from MeOH, filtered and dried to provide the title compound.

Intermediate 16

2-(Azetidin-1-yl)-6-bromo-4-chloro-3-(4-(trifluoromethyl)benzyl)quinoline

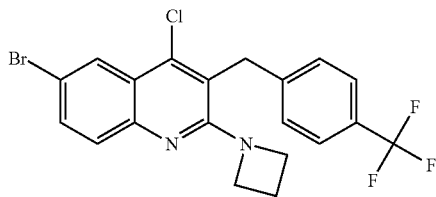 [SMILES: FC(F)(F)c1ccc(Cc2c(N3CCC3)nc3ccc(Br)cc3c2Cl)cc1]

6-Bromo-2,4-dichloro-3-[4-(trifluoromethyl)benzyl] quinoline (2.50 g, 5.75 mmol, Intermediate 10: step c), azetidine (0.984 g, 17.2 mmol) and DMF (29 mL) were combined in a reaction tube, then sealed and heated to 100° C. and maintained at that temperature overnight. The reaction vessel was then cooled and the contents were transferred to a separatory funnel with EtOAc dilution, then extracted once with a saturated, aqueous NH$_4$Cl solution and three times with deionized water. The organic phase was separated, dried over MgSO$_4$, filtered and concentrated under reduced pressure. The crude product was purified by flash column chromatography (silica gel, 0-20% hexane/ethyl acetate) to provide the title compound.

Intermediate 17

3-(4-(1H-pyrazol-1-yl)benzyl)-2-(azetidin-1-yl)-6-bromo-4-chloroquinoline

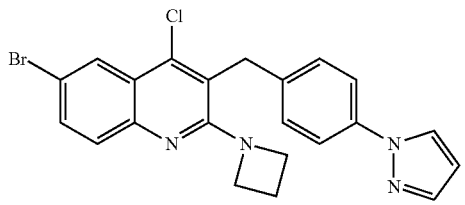 [SMILES: Clc1c(Cc2ccc(-n3cccn3)cc2)c(N2CCC2)nc2ccc(Br)cc12]

3-(4-(1H-Pyrazol-1-yl)benzyl)-6-bromo-2,4-dichloroquinoline (2.50 g, 5.77 mmol, Intermediate 4: step c), azetidine (988 mg, 17.3 mmol), and DMF (30 mL) were combined in a reaction tube, then sealed and heated to 100° C. and maintained at that temperature overnight. The vessel was then cooled and contents were transferred to a separatory funnel with EtOAc dilution, then extracted three times with deionized water. The organic phase was separated, dried over MgSO$_4$, filtered and concentrated under reduced pressure. The crude product was purified by flash column chromatography (silica gel, 0-20% hexane/ethyl acetate) to afford the title compound.

Intermediate 18

1-Methyl-1H-1,2,3-triazole-5-carbaldehyde

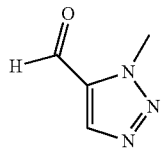

The title compound was prepared according to the patent application WO2008/135826. To a 50 mL 2-necked flask containing 1-methyl-1H-1,2,3-triazole (1.0 g, 12.0 mmol, prepared according to PCT Int. Appl., 2008098104) was added THF (45 mL) and the colorless solution was cooled to −40° C. Then, n–BuLi (2.5 M in hexanes, 4.8 mL, 12.0 mmol) was added dropwise which afforded a dark reddish-brown viscous solution. The mixture was stirred between −30 to −20° C. for 45 minutes, then neat DMF (3 mL, 38.5 mmol) was introduced at −10° C. The mixture was allowed to warm up to room temperature and stirred for 60 minutes, followed by pouring into water. The aqueous portion was extracted with EtOAc (4×50 mL) and the combined organics were washed with brine, dried over MgSO$_4$, filtered and concentrated. The aqueous portion was back-extracted with DCM (3×50 mL) and dried as above. The combined organics were concentrated to give a light brown oil that was much more UV active than the starting material. TLC in either 25% CH$_3$CN-DCM or 25% EtOAc-DCM showed the product to have a slightly higher R$_f$ than the starting material. Chromatography on silica gel (100% DCM increasing to 25% CH$_3$CN-DCM) provided the title compound as a colorless oil.

Example 1

(2,4-Dichloro-3-phenylquinolin-6-yl)(3,5-dimethylisoxazol-4-yl)methanol

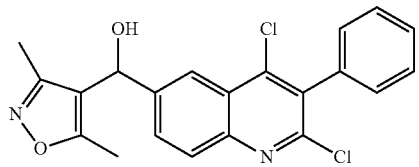 [SMILES: Cc1noc(C)c1C(O)c1ccc2nc(Cl)c(-c3ccccc3)c(Cl)c2c1]

THF (5 mL) was added to a mixture of 6-bromo-2,4-dichloro-3-phenylquinoline (363 mg, 1.03 mmol, Intermediate 1: step c) and 3,5-dimethylisoxazole-4-carbaldehyde (180 mg, 1.44 mmol) under a nitrogen atmosphere. The resulting colorless solution was cooled in a dry ice/acetone bath. n-BuLi (1.6 M in hexane, 0.77 mL, 1.23 mmol) was added dropwise and the mixture was stirred at −78° C. for 30 minutes, then moved to an ice bath and stirred for 30 minutes. The reaction was quenched by addition of saturated aqueous NH$_4$Cl and was diluted with water. The mixture was extracted three times with EtOAc. The organic phase was dried (Na$_2$SO$_4$), filtered, and concentrated to afford the crude title compound. ¹H NMR (400 MHz, DMSO-d₆) δ ppm 8.35 (s, 1H), 8.04 (d, J=8.80 Hz, 1H), 7.74 (dd, J=1.71, 8.80 Hz, 1H), 7.48-7.62 (m, 3H), 7.35-7.48 (m, 2H), 6.25 (d, J=4.16 Hz, 1H), 5.99 (d, J=3.42 Hz, 1H), 2.37 (s, 3H), 1.99 (s, 3H); MS m/e 398.9 (M+H)⁺.

Example 2

(2,4-Dichloro-3-phenylquinolin-6-yl)(1-methyl-1H-imidazol-5-yl)methanol

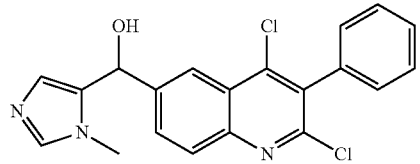 [SMILES: Cn1cncc1C(O)c1ccc2nc(Cl)c(-c3ccccc3)c(Cl)c2c1]

n-BuLi (2.5 M in hexanes, 0.52 mL, 1.3 mmol) was added dropwise to a solution of 6-bromo-2,4-dichloro-3-phenylquinoline (353 mg, 1 mmol, Intermediate 1: step c) in dry THF (10 mL) in a 100 mL three necked round bottomed flask at −78° C. under N₂. Stirring was continued for 30 minutes then a solution of 1-methyl-1H-imidazole-5-carbaldehyde (110 mg, 1 mmol) in dry THF (10 mL) was added at −78° C. The cooling bath was removed and the mixture was gradually warmed up to room temperature and stirred for 2 hours. The mixture was quenched by adding H₂O (10 mL) and then extracted with CH₂Cl₂ (2×50 mL). The combined organic phase was dried over Na₂SO₄, concentrated to dryness and purified by prep-TLC (developed by CH₃OH/CH₂Cl₂ 1:5) to afford the title compound as a white solid. MS (ESI): 384.1 [M+H]⁺. ¹H NMR (300 MHz, CD₃OD) δ ppm 8.45 (s, 1H), 7.94 (dd, J=42.2, 8.0 Hz, 2H), 7.73-7.24 (m, 6H), 6.56 (s, 1H), 6.16 (s, 1H), 3.70 (s, 3H).

Example 3

(2,4-Dichloro-3-(2-chlorophenyl) quinolin-6-yl)(1-methyl-1H-imidazol-5-yl) methanol

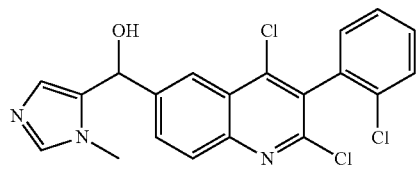 [SMILES: Cn1cncc1C(O)c1ccc2nc(Cl)c(-c3ccccc3Cl)c(Cl)c2c1]

n-BuLi (2.5 M in hexanes, 0.52 mL, 1.3 mmol) was added dropwise to a solution of 6-bromo-2,4-dichloro-3-(2-chlorophenyl)quinolone (387.5 mg. 1 mmol, Intermediate 2: step c) in dry THF (10 mL) in a 100 mL three necked round bottomed flask at −78° C. under N₂. Stirring was continued for 30 minutes then a solution of 1-methyl-1H-imidazole-5-carbaldehyde (110 mg, 1 mmol) in dry THF (10 mL) was added at −78° C. The cooling bath was removed and the mixture was gradually warmed to room temperature and stirred for 2 hours. The mixture was quenched by adding H₂O (10 mL) and then extracted with CH₂Cl₂ (2×50 mL). The combined organic phase was dried over Na₂SO₄, concentrated to dryness and purified by prep-TLC (developed by CH₃OH/CH₂Cl₂ 1:40) to afford the title compound as a white solid. MS (ESI): 418.1 [M+H]⁺. ¹H NMR (300 MHz, CD₃OD) δ ppm 8.47 (s, 1H), 8.06 (d, J=8.6 Hz, 1H), 7.98-7.84 (m, 1H), 7.68-7.34 (m, 5H), 6.57 (d, J=3.3 Hz, 1H), 6.17 (s, 1H), 3.71 (s, 3H).

Example 4

(2,4-Dichloro-8-methyl-3-phenylquinolin-6-yl)(1-methyl-1H-imidazol-5-yl)methanol.TFA

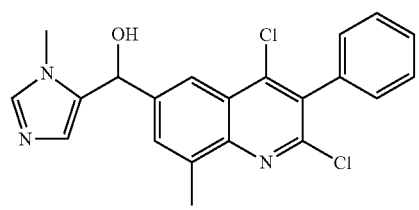 [SMILES: Cc1cc(C(O)c2cncn2C)cc2c(Cl)c(-c3ccccc3)c(Cl)nc12]

A solution of 5-bromo-1-methyl-1H-imidazole (342 mg, 2.12 mmol) in DCM (2.2 mL) was stirred in an ice bath while iPrMgCl—LiCl (1.77 mL, 1.2 M in THF, 2.1 mmol) was added dropwise over 1-2 minutes under argon. After 10 minutes stirring at room temperature, the homogeneous amber reaction was added dropwise over 1-2 minutes to a slurry of 2,4-dichloro-8-methyl-3-phenylquinoline-6-carbaldehyde (460 mg, 1.46 mmol, Intermediate 3: step b) in LaCl₃·2LiCl (7.60 mL, 0.56 M in THF, 1.46 mmol) on an ice bath. The reaction was removed from the ice bath immediately following Grignard addition and stirred for 45 minutes at ambient temperature. The mixture was then partitioned between 9:1 DCM/MeOH (14 mL) and 5 M aqueous NH₄Cl (0.72 mL). This mixture was filtered over Celite®, and the filter cake washed with 9:1 DCM/MeOH (1×5 mL). The combined clear dark yellow filtrates were dried (Na₂SO₄), filtered, and concentrated to provide a beige foam. A portion was purified by C18 HPLC (20-100% CH₃CN with 0.1% TFA throughout) to provide, after lyophilization, the title compound as a white solid. ¹H NMR (400 MHz, CD₃OD) δ ppm 8.90 (s, 1H), 8.34 (s, 1H), 7.75 (s, 1H), 7.46-7.59 (m 3H), 7.32-7.38 (m, 2H), 7.15 (s, 1H), 6.22 (s, 1H), 3.94 (s, 3H), 2.78 (s, 3H); MS m/e 398.1 [M+H]⁺.

Example 5a (3-(4-(1H-Pyrazol-1-yl)benzyl)-4-chloro-2-methoxyquinolin-6-yl)(1-methyl-1H-1,2,3-triazol-5-yl)methanol

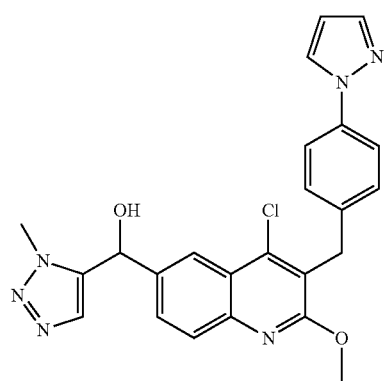 [SMILES: COc1nc2ccc(C(O)c3cnnn3C)cc2c(Cl)c1Cc1ccc(-n2cccn2)cc1]

A solution of n-butyllithium in hexanes (1.6 M, 0.71 mL, 1.1 mmol) was added dropwise to a stirring solution of 3-(4-(1H-pyrazol-1-yl)benzyl)-6-bromo-4-chloro-2-methoxyquinoline (490 mg, 1.1 mmol, Intermediate 4: step d) in tetrahydrofuran (11 mL) at −78° C. After 2 minutes, a solution of 1-methyl-1H-1,2,3-triazole-5-carbaldehyde (140 mg, 1.1 mmol, Intermediate 18) in tetrahydrofuran (1 mL) was added dropwise. After 5 minutes, the flask was placed into an ice-water bath. After 1 hour, water (10 mL) and ethyl acetate (60 mL) were added. The biphasic mixture was stirred for 10 minutes. Half-saturated aqueous sodium chloride solution (50 mL) was added and the layers were separated. The organic layer was dried with sodium sulfate and the dried solution was filtered. Silica gel (4 g) was added to the filtrate and the mixture was concentrated by rotary evaporation to afford a free-flowing powder. The powder was loaded onto a silica gel column for flash column chromatography purification. Elution with 100% hexanes initially, grading to 100% ethyl acetate provided the title compound as a white foam which was impure. The foam was suspended in methanol (20 mL) and the suspension was sonicated for 5 minutes. The solids were collected by filtration and rinsed with methanol (5 mL). The collected solids were dried to provide the title compound as a white solid. $^1$H NMR (600 MHz, DMSO-$d_6$) δ ppm 8.42 (d, J=2.5 Hz, 1H), 8.21 (d, J=1.8 Hz, 1H), 7.86 (d, J=8.6 Hz, 1H), 7.75-7.71 (m, 2H), 7.72-7.67 (m, 2H), 7.37-7.32 (m, 3H), 6.55 (d, J=5.2 Hz, 1H), 6.53-6.49 (m, 1H), 6.22 (d, J=5.2 Hz, 1H), 4.30 (s, 2H), 4.04 (s, 3H), 3.97 (s, 3H); MS (ESI): mass calcd. for $C_{24}H_{21}ClN_6O_2$, 460.1; m/z found, 461.1 $[M+H]^+$.

(3-(4-(1H-Pyrazol-1-yl)benzyl)-4-chloro-2-methoxyquinolin-6-yl)(1-methyl-1H-1,2,3-triazol-5-yl)methanol was purified by chiral SFC (Chiralpak IA, 5 μm, 250×20 mm, mobile phase: 55% $CO_2$, 45% methanol) to provide two enantiomers. Each enantiomer was further purified by preparative liquid chromatography (stationary phase: irregular 15-40 μm, 30 g Merck, mobile phase: 95% dichloromethane, 5% methanol). The first eluting enantiomer off the chiral column was Example 5b: $^1$H NMR (400 MHz, CDCl$_3$) δ ppm 8.17 (d, J=2.3 Hz, 1H), 7.90-7.82 (m, 2H), 7.68 (d, J=1.7 Hz, 1H), 7.60-7.53 (m, 3H), 7.41 (d, J=1.5 Hz, 1H), 7.40-7.33 (m, 2H), 6.46-6.39 (m, 1H), 6.14 (s, 1H), 4.33 (s, 2H), 4.10 (s, 3H), 3.99 (s, 3H), 2.92 (br s, 1H); MS (ESI): mass calcd. for $C_{24}H_{21}ClN_6O_2$, 460.1; m/z found, 460.9 $[M+H]^+$ and the second eluting enantiomer was Example 5c: $^1$H NMR (400 MHz, CDCl$_3$) δ ppm 8.17 (d, J=1.9 Hz, 1H), 7.90-7.82 (m, 2H), 7.68 (d, J=1.7 Hz, 1H), 7.60-7.52 (m, 3H), 7.41 (s, 1H), 7.40-7.33 (m, 2H), 6.46-6.40 (m, 1H), 6.14 (s, 1H), 4.33 (s, 2H), 4.10 (s, 3H), 3.99 (s, 3H), 2.92 (br s, 1H); MS (ESI): mass calcd. for $C_{24}H_{21}ClN_6O_2$, 460.1; m/z found, 460.9 $[M+H]^+$.

Example 6

(1-Acetylpiperidin-4-yl){4-chloro-2-methoxy-3-[4-(trifluoromethyl)benzyl]quinolin-6-yl}methanol

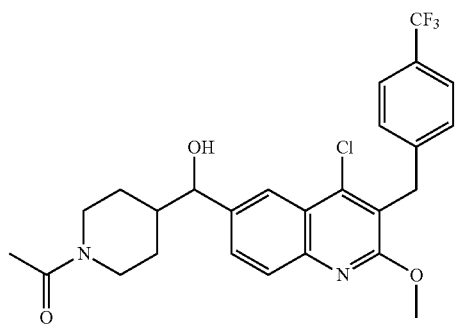 [SMILES: COc1nc2ccc(C(O)C3CCN(C(C)=O)CC3)cc2c(Cl)c1Cc1ccc(C(F)(F)F)cc1]

To a solution of (4-chloro-2-methoxy-3-(4-(trifluoromethyl)benzyl)quinolin-6-yl)(piperidin-4-yl)methanol (74 mg, 0.16 mmol, Intermediate 11: step b) in DCM (3 mL) was added Et$_3$N (24 L, 0.18 mmol) and the resulting solution cooled to 0° C. Then acetic anhydride (16 μL, 0.17 mmol) was added dropwise and the reaction stirred at 0° C. for 30 minutes. The mixture was diluted with DCM and washed with saturated aqueous NaHCO$_3$. The organic layer was dried (MgSO$_4$), filtered, concentrated to dryness and purified by reverse-phase HPLC (acetonitrile/water+ TFA). The acidic fractions were neutralized by diluting with EtOAc and washing with saturated aqueous NaHCO$_3$. The organics were concentrated to dryness, dissolved in 1/1 acetonitrile/water and lyophilized to provide the title compound as a white solid. $^1$H NMR (400 MHz, DMSO-$d_6$) δ ppm 8.02-7.99 (m, 1H), 7.84-7.80 (m, 1H), 7.72-7.68 (m, 1H), 7.64 (d, J=8.0 Hz, 2H), 7.43 (d, J=7.9 Hz, 2H), 5.49 (s, 1H), 4.57-4.50 (m, 1H), 4.43-4.30 (m, 3H), 4.01 (s, 3H), 3.83-3.71 (m, 1H), 2.94-2.84 (m, 1H), 2.40-2.33 (m, 1H), 1.94 (d, J=8.2 Hz, 3H), 1.84-1.72 (m, 2H), 1.32-1.19 (m, 2H), 1.16-1.03 (m, 1H). MS (ESI): mass calcd. for $C_{26}H_{26}ClF_3N_2O_3$, 506.2; m/z found, 507.1 $[M+H]^+$.

Example 7

(3-(4-(1H-Pyrazol-1-yl)benzyl)-2,4-dichloroquinolin-6-yl)(1-methyl-1H-imidazol-5-yl)methanol

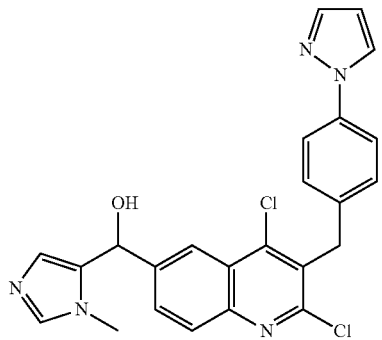 [SMILES: Cn1cncc1C(O)c1ccc2nc(Cl)c(Cc3ccc(-n4cccn4)cc3)c(Cl)c2c1]

A solution of n-BuLi (2.5 M in hexanes. 0.4 mL. 1 mmol) was added dropwise by syringe to a solution of 3-(4-(1H-pyrazol-1-yl)benzyl)-6-bromo-2,4-dichloroquinoline (0.500 g, 1.15 mmol, Intermediate 4: step c) in dry THF (13.5 mL) in a dry ice-acetone bath. After 1-2 minutes, a solution of 1-methyl-1H-imidazole-5-carbaldehyde (141.6 mg, 1.286 mmol) in dry THF (0.2 mL) was added dropwise. The reaction was stirred for 5 minutes and moved to an ice bath for 1.5 hours before allowing the reaction to warm to room temperature. The reaction was quenched with saturated aqueous ammonium chloride. The mixture was partitioned between water and dichloromethane. The separated aqueous phase was further extracted with dichloromethane. The combined organic phase was dried ($Na_2SO_4$), filtered, and concentrated. Crude product was purified by flash column chromatography (silica gel, 0-10% MeOH-DCM), followed by reverse-phase chromatography (acetonitrile/$H_2O$+0.05% TFA). Product fractions were basified with saturated aqueous sodium bicarbonate and extracted with DCM, before being dried ($Na_2SO_4$), filtered, and concentrated to provide the title compound. $^1$H NMR (400 MHz, $CD_3OD$) δ ppm 8.43 (s, 1H), 8.12 (d, J=2.4 Hz, 1H), 7.96 (dd, J=8.7, 3.8 Hz, 1H), 7.83 (dd, J=8.7, 1.6 Hz, 1H), 7.66 (dd, J=9.6, 2.2 Hz, 1H), 7.62 (d, J=8.8 Hz, 3H), 7.30 (dd, J=12.9, 6.5 Hz, 2H), 6.56 (s, 1H), 6.48 (t, J=2.1 Hz, 1H), 6.14 (s, 1H), 4.57 (d, J=6.1 Hz, 2H), 3.69 (s, 3H); MS m/e 464.1 [M+H]$^+$.

Example 8a

4-Chloro-3-(4-fluorobenzyl)-2-methoxyquinolin-6-yl) 1,2-dimethyl-1H-imidazol-5-yl)methanol

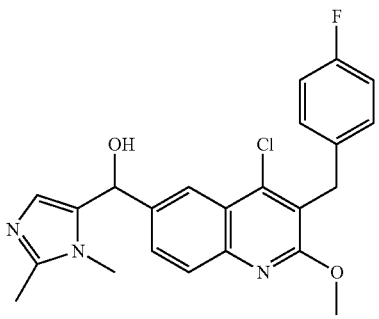 [SMILES: COc1nc2ccc(C(O)c3cnc(C)n3C)cc2c(Cl)c1Cc1ccc(F)cc1]

A solution of n-BuLi (2.5 M in hexanes, 0.52 mL, 1.3 mmol) was added dropwise by syringe to a solution of 6-bromo-4-chloro-3-(4-fluorobenzyl)-2-methoxyquinoline (0.5 g, 1.3 mmol, Intermediate 7: step d) in dry THF (13 mL) in a dry ice-acetone bath. After 1-2 minutes, a solution of 1,2-dimethyl-1H-imidazole-5-carbaldehyde (147.1 mg, 1.185 mmol) in dry THF (3 mL) was added dropwise. The reaction was stirred for 5 minutes, then was moved to an ice bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The residue was purified by flash column chromatography (silica gel, 0-3% MeOH-DCM) to provide the title compound. $^1$H NMR (400 MHz. $CDCl_3$) δ ppm 8.21 (d, J=0.8 Hz, 1H), 7.80 (d, J=8.6 Hz, 1H), 7.59 (dd, J=8.6, 1.9 Hz, 1H), 7.28-7.23 (m, 2H), 6.96-6.89 (m, 2H), 6.47 (s, 1H), 5.98 (s, 1H), 4.25 (s, 2H), 4.08 (s, 3H), 3.45 (s, 3H), 2.29 (s, 3H); MS m/e 425.9 [M+H]$^+$.

Example 8a was purified by chiral SFC (ChiralPak AD-H, 65:35 $CO_2$/iPrOH+0.3% iPrNH$_2$) to provide two pure enantiomers. The first eluting enantiomer was Example 8b: $^1$H NMR (400 MHz, $CDCl_3$) δ ppm 8.22 (s, 1H), 7.81 (d, J=8.6 Hz, 1H), 7.61 (dd, J=8.6, 1.9 Hz, 1H), 7.29-7.23 (m, 2H), 6.96-6.90 (m, 2H), 6.52 (s, 1H), 6.01 (s, 1H), 4.26 (s, 2H), 4.08 (s, 3H), 3.48 (s, 3H), 2.33 (s, 3H); MS m/e 425.1 [M]$^+$. The second eluting enantiomer was Example 8c: $^1$H NMR (400 MHz, $CDCl_3$) δ ppm 8.22 (s, 1H), 7.81 (d, J=8.6 Hz, 1H), 7.60 (dd. J=8.6, 1.9 Hz, 1H), 7.28-7.23 (m, J=5.6 Hz, 2H), 6.96-6.89 (m, 2H), 6.50 (s, 1H), 6.00 (s, 1H), 4.26 (s, 2H), 4.08 (s, 3H), 3.47 (s, 3H), 2.32 (s, 3H); MS m/e 425.1 [M]$^+$.

Example 9

4-((4-Chloro-3-(4-cyanobenzyl)-2-methoxyquinolin-6-yl)(hydroxy)methyl)benzonitrile

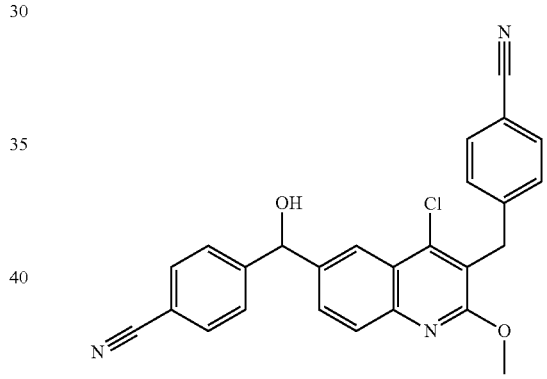

A solution of n-BuLi (2.5 M in hexanes, 1.25 mL. 3.12 mmol) was added dropwise by syringe to a solution of 4-((6-bromo-4-chloro-2-methoxyquinolin-3-yl)methyl)benzonitrile (1.211 g, 3.125 mmol, Intermediate 8: step d) in dry THF (15 mL) in a dry ice-acetone bath. After 1-2 minutes, a solution of 4-formylbenzonitrile (498.8 mg, 3.804 mmol) in dry THF (2 mL) was added dropwise. The reaction was stirred for 5 minutes and then removed from the cold bath and allowed to warm to room temperature. The reaction was quenched with saturated aqueous ammonium chloride. The mixture was partitioned between water and dichloromethane. The separated aqueous phase was further extracted with dichloromethane. The combined organic phase was dried ($Na_2SO_4$), filtered, and concentrated. Crude product was purified by flash column chromatography (silica gel, 100% EtOAc, followed by 0-5% MeOH-DCM), to provide the title compound. $^1$H NMR (500 MHz, $CDCl_3$) δ 8.13-8.11 (m, 1H), 7.79 (d, J=8.6 Hz, 1H), 7.63-7.59 (m, 2H), 7.56-7.51 (m, 5H), 7.38-7.34 (m, 2H), 6.03 (d, J=3.2 Hz, 1H), 4.33 (s, 2H), 4.05 (s, 3H); MS m/e 440.0 [M+H]+.

Example 10

4-Chloro-2-methoxy-8-methyl-3-(4-(methylsulfonyl) benzyl)quinolin-6-yl)(1-methyl-1H-imidazol-5-yl) methanol.TFA

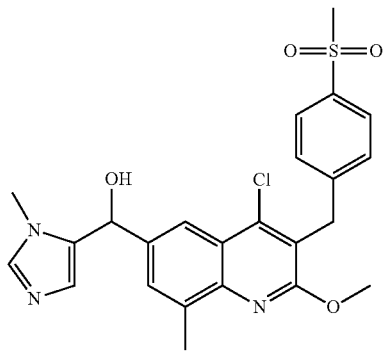 [SMILES: COc1nc2c(C)cc(C(O)c3cncn3C)cc2c(Cl)c1Cc1ccc(S(C)(=O)=O)cc1]

A mixture of (4-chloro-2-methoxy-8-methyl-3-(4-(methylsulfonyl)benzyl)quinolin-6-yl)(1-methyl-1H-imidazol-5-yl)methanone (0.12 g, 0.252 mmol, Intermediate 13: step e) and sodium borohydride (0.019 g, 0.504 mmol) in MeOH (3 mL) was stirred at room temperature for 2 hours and concentrated to remove MeOH. The residue was diluted with EtOAc, saturated aqueous NaHCO3 was added, and the resulting mixture was stirred at room temperature for 30 minutes. The layers were separated and the aqueous layer was further extracted with EtOAc. The combined EtOAc extracts were washed with brine, dried over Na2SO4, concentrated to dryness, and chromatographed (10% MeOH in DCM). Further purification by HPLC (H2O/acetonitrile/1% TFA) provided the TFA salt of the title compound as a white solid. 1H NMR (400 MHz, CD3OD) δ ppm 8.79-8.94 (m, 1H), 8.13-8.23 (m, 1H), 7.80-7.94 (m, 2H), 7.57-7.69 (m, 1H), 7.45-7.56 (m, 2H), 7.05-7.16 (m, 1H), 6.08-6.19 (m, 1H), 4.45 (s, 2H), 4.10 (s, 3H), 3.91 (s, 3H), 3.07 (s, 3H), 2.71 (s, 3H), 2.63 (s, 1H). MS (EI) 486 [M+H]+.

Example 11

(4-Chloro-2-methoxy-8-methyl-3-(3-(trifluoromethyl)benzyl)quinolin-6-yl)(1-methyl-1H-imidazol-5-yl)methanol

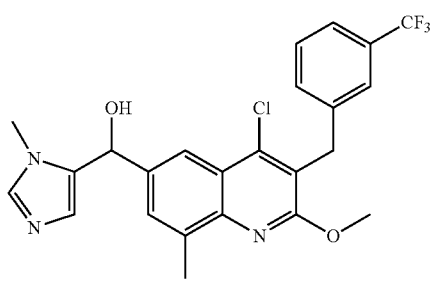 [SMILES: COc1nc2c(C)cc(C(O)c3cncn3C)cc2c(Cl)c1Cc1cccc(C(F)(F)F)c1]

Sodium borohydride (0.016 g, 0.422 mmol) was added in one portion to a suspension of (4-chloro-2-methoxy-8-methyl-3-(3-(trifluoromethyl)benzyl)quinolin-6-yl)(1-methyl-1H-imidazol-5-yl)methanone (0.1 g, 0.211 mmol, Intermediate 15: step d) in MeOH (3 mL). The mixture was stirred at room temperature overnight, then filtered, rinsing the solids with MeOH and H2O. The solid product was dried under reduced pressure to provide the title compound. 1H NMR (400 MHz, CDCl3) δ ppm 8.08 (s, 1H), 7.57-7.69 (m, 1H), 7.41-7.53 (m, 4H), 7.30-7.41 (m, 1H), 6.76 (s, 1H), 5.94-6.15 (m, 1H), 4.35 (s, 2H), 4.09 (s, 3H), 3.60 (s, 3H), 2.67 (s, 3H), 2.58 (m, 1H). MS (EI) 476 [M+H]+.

Example 12

(3-(4-(1H-Pyrazol-1-yl)benzyl)-4-chloro-2-methoxy-8-methylquinolin-6-yl)(1-methyl-1H-imidazol-5-yl) methanol.TFA

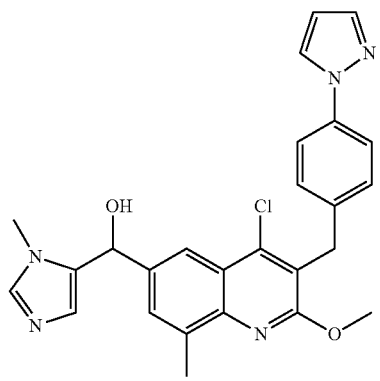 [SMILES: COc1nc2c(C)cc(C(O)c3cncn3C)cc2c(Cl)c1Cc1ccc(-n2cccn2)cc1]

A mixture of (3-(4-(1H-pyrazol-1-yl)benzyl)-4-chloro-2-methoxy-8-methylquinolin-6-yl)(1-methyl-1H-imidazol-5-yl)methanone (0.2 g, 0.424 mmol, Intermediate 14: step b) and sodium borohydride (0.032 g, 0.848 mmol) in MeOH (3 mL) was stirred at room temperature for 2 hours and concentrated to remove MeOH. The residue was diluted with EtOAc and saturated aqueous NaHCO3 was added and the mixture was stirred at room temperature for 30 minutes. The layers were separated and the aqueous layer was further extracted with EtOAc. The combined EtOAc extracts were washed with brine, dried over Na2SO4, concentrated to dryness, and chromatographed (10% MeOH in DCM). Further purification by HPLC (H2O/acetonitrile/1% TFA) provided the TFA salt of the title compound as a white solid. 1H NMR (400 MHz, CDCl3) δ ppm 8.42-8.56 (m, 1H), 8.02 (s, 1H), 7.82 (d, J=2.5 Hz, 1H), 7.68 (s, 1H), 7.51 (d, J=8.6 Hz, 2H), 7.30-7.46 (m, 3H), 6.94 (s, 1H), 6.43 (t, J=2.3 Hz, 1H), 5.96 (s, 1H), 4.32 (s, 2H), 4.11 (s, 3H), 3.72 (s, 3H), 2.67 (s, 3H). MS (EI) 474 [M+H]⁺.

Example 13

(2,4-Dichloro-3-phenylquinolin-6-yl)(1,2-dimethyl-1H-imidazol-5-yl)methanol

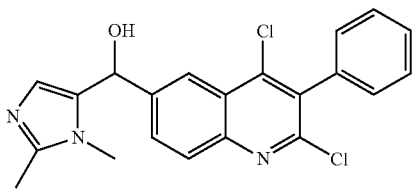 [SMILES: Cc1ncc(C(O)c2ccc3nc(Cl)c(-c4ccccc4)c(Cl)c3c2)n1C]

To a flask containing 6-bromo-2,4-dichloro-3-phenylquinoline (4 g, 11.33 mmol, Intermediate 1: step c) was added THF (200 mL) to give a homogeneous clear solution. The solution was cooled in a dry-ice/acetone bath and n-BuLi (2.5 M in hexanes, 4.25 mL, 10.63 mmol) was added which resulted in an immediate reddish-brownish mixture. After 2 minutes, a THF solution of 1,2-dimethyl-1H-imidazole-5-carbaldehyde (1.75 g, 14.1 mmol in 10 mL THF) was added and the reaction mixture became a light yellow color. The −78° C. bath was replaced with a 0° C. ice-bath and after 40 minutes, the reaction mixture was quenched with aqueous NH₄Cl solution and the aqueous portion was extracted with EtOAc (4×100 mL). The combined organics were washed with brine, dried over MgSO₄, filtered and concentrated. The resulting solid was triturated with Et₂O to provide the title compound as an off white powder. ¹H NMR (500 MHz, CDCl₃) δ ppm 8.39 (s, 1H), 8.03 (d, J=8.7 Hz, 1H), 7.76 (dd, J=8.7, 1.8 Hz, 1H), 7.51 (dd, J=9.7, 7.2 Hz, 3H), 7.40-7.31 (m, 2H), 6.47 (s, 1H), 6.05 (s, 1H), 4.47 (s, 1H), 3.47 (s, 3H), 2.31 (s, 3H). MS (ESI): mass calcd. for $C_{21}H_{17}Cl_2N_3O$, 397.1, m/z found 398.0 [M+H]⁺.

Example 14a (4-Chloro-2-methoxy-3-(4-(trifluoromethyl)benzyl)quinolin-6-yl)(2,6-dimethylpyridin-3-yl)methanol

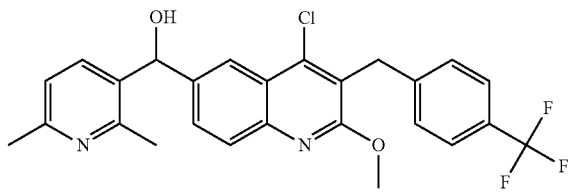 [SMILES: COc1nc2ccc(C(O)c3ccc(C)nc3C)cc2c(Cl)c1Cc1ccc(C(F)(F)F)cc1]

To a flask containing 6-bromo-4-chloro-2-methoxy-3-(4-(trifluoromethyl)benzyl)quinoline (1.85 g, 4.3 mmol, Intermediate 10: step d) was added THF (45 mL) at room temperature which resulted in a colorless homogeneous solution. The solution was cooled to −70° C. and then n-BuLi (2.5 M in hexanes, 1.75 mL, 4.38 mmol) was added dropwise. After 2 minutes, 2,6-dimethylnicotinaldehyde (755 mg, 5.59 mmol, in 2 mL THF) was introduced and the color of the mixture went from a reddish-brown to green. The reaction mixture was allowed to warm to −20° C. over 40 minutes at which time the reaction was quenched with aqueous NH₄Cl solution. The aqueous portion was extracted with EtOAc (3×50 mL) and the combined organics were washed with brine, dried over MgSO₄, filtered and concentrated. Chromatography on silica gel (10% acetone-hexane increasing to 30% acetone) afforded the title compound. ¹H NMR (500 MHz, CDCl₃) δ ppm 8.10 (d, J=1.8 Hz, 1H), 7.77 (d, J=8.6 Hz, 1H), 7.69 (d, J=7.9 Hz, 1H), 7.49 (dd, J=8.1, 2.7 Hz, 3H), 7.37 (d, J=8.1 Hz, 2H), 7.01 (d, J=7.9 Hz, 1H), 6.11 (s, 1H), 4.33 (s, 2H), 4.06 (s, 3H), 3.26 (s, 1H), 2.47 (s, 3H), 2.43 (s, 3H). MS (ESI): mass calcd. for $C_{26}H_{22}ClF_3N_2O_2$, 486.1, m/z found 487.1 [M+H]+. Example 14a was purified by chiral SFC (ChiralPak IC, 5 m 250×20 mm, Mobile phase: 65:35 CO₂/iPrOH) to provide two pure enantiomers. The first eluting enantiomer was Example 14b and the second eluting enantiomer was Example 14c.

Example 15a (4-Chloro-2-methoxy-3-(4-(trifluoromethyl)benzyl)quinolin-6-yl)(1,2-dimethyl-1H-imidazol-5-yl)methanol

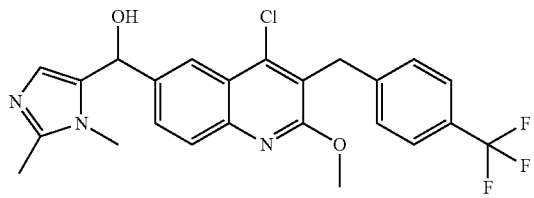 [SMILES: COc1nc2ccc(C(O)c3cnc(C)n3C)cc2c(Cl)c1Cc1ccc(C(F)(F)F)cc1]

To a flask containing 6-bromo-4-chloro-2-methoxy-3-(4-(trifluoromethyl)benzyl)quinoline (2.0 g, 4.64 mmol, Intermediate 10: step d) was added THF (25 mL). The solution was cooled to −70° C. and then n-BuLi (2.5 M in hexanes, 1.8 mL, 4.5 mmol) was added dropwise. After 2 minutes, 1,2-dimethyl-1H-imidazole-5-carbaldehyde (720 mg, 5.8 mmol in 5 mL THF) was introduced. The reaction mixture was allowed to warm to 0° C. over 60 minutes at which time it was quenched with aqueous NH₄Cl solution. The aqueous portion was extracted with EtOAc:THF (10:1, 5×50 mL). The combined organics were washed with brine, dried over MgSO₄, filtered and concentrated. The solid was triturated with EtOAc:Et₂O (1:1), collected by filtration, rinsed with additional Et₂O and dried to afford the title compound. The mother liquors were concentrated and chromatographed on silica gel (3% MeOH-DCM increasing to 10% MeOH) to provide additional title compound. ¹H NMR (500 MHz, CDCl₃) δ ppm 8.23 (s, 1H), 7.83 (d, J=8.6 Hz, 1H), 7.62 (dd, J=8.6, 1.9 Hz, 1H), 7.50 (d, J=8.2 Hz, 2H), 7.39 (d, J=8.1 Hz, 2H), 6.52 (s, 1H), 6.01 (s, 1H), 4.35 (s, 2H), 4.08 (s, 3H), 3.48 (s, 3H), 2.33 (s, 3H). MS (ESI): mass calcd. for $C_{24}H_{21}ClF_3N_3O_2$, 475.1, m/z found 476.1 [M+H]⁺. Example 15a was purified by chiral SFC (ChiralPak AD (20 μm) diacel, mobile phase: heptane/2-propanol +2% isopropylamine (90:10), column (50×41 mm)). The first eluting enantiomer was Example 15b. The second eluting enantiomer was Example 15c.

Example 16

(2,6-Dimethylpyridin-3-yl)(2-methoxy-3-(4-(trifluoromethyl)benzyl)quinolin-6-yl)methanol

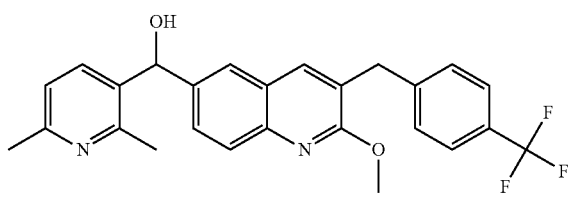 [SMILES: COc1nc2ccc(C(O)c3ccc(C)nc3C)cc2cc1Cc1ccc(C(F)(F)F)cc1]

A 250 mL Parr flask containing (4-chloro-2-methoxy-3-(4-(trifluoromethyl)benzyl)quinolin-6-yl)(2,6-dimethylpyridin-3-yl)methanol (155 mg, 0.32 mmol, Example 14a) was added EtOH (25 mL) and Et$_3$N (1 mL) followed by 5% palladium on carbon (75 mg). The flask was pressurized to 50 psi with H$_2$ gas and shaken for 18 hours. HPLC analysis indicated the conversion was approximately 40%. The reaction mixture was filtered through Celite® and concentrated. The residue was dissolved in MeOH and run in the H-cube hydrogenation apparatus using a 10% Pd/C cartridge at 50° C., 70 psi H$_2$ and 1.2 ml/minute (all with closed loop recycling). After the cycling was complete, the solution was concentrated to dryness and the residue was chromatographed on silica gel (10% EtOAc-DCM increasing to 5% MeOH-DCM) to provide the title compound as a white solid. $^1$H NMR (500 MHz, CDCl$_3$) δ ppm 7.76 (d, J=8.5 Hz, 1H), 7.58-7.47 (m, 3H), 7.40-7.31 (m, 3H), 7.30-7.20 (m, 2H), 6.94 (d, J=7.7 Hz, 1H), 4.05 (overlapping s, 6H), 2.51 (s, 3H), 2.45 (s, 3H). MS (ESI): mass calcd. for C$_{26}$H$_{23}$F$_3$N$_2$O$_2$, 452.2, m/z found 453.2 [M+H]$^+$.

Example 17a (4-Chloro-2-methoxy-3-(4-(trifluoromethyl)benzyl)quinolin-6-yl)(1-methyl-1H-1,2,3-triazol-5-yl)methanol

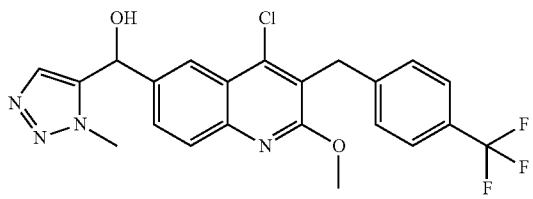 [SMILES: COc1nc2ccc(C(O)c3cnnn3C)cc2c(Cl)c1Cc1ccc(C(F)(F)F)cc1]

To a flask containing 6-bromo-4-chloro-2-methoxy-3-(4-(trifluoromethyl)benzyl)quinoline (1.45 g, 3.37 mmol, Intermediate 10: step d) was added THF (25 mL) and the solution was cooled to −75° C. n-BuLi (2.5 M in hexanes, 1.3 mL, 3.25 mmol) was added dropwise. After 2 minutes, 1-methyl-1H-1,2,3-triazole-5-carbaldehyde (580 mg, 5.22 mmol, Intermediate 18) in 3 mL THF was introduced. The reaction mixture was allowed to warm to −20° C. over 45 minutes at which time the reaction was quenched with aqueous NH$_4$Cl solution. The aqueous portion was extracted with EtOAc (5×40 mL) and the combined organics were washed with brine, dried over MgSO$_4$, filtered and concentrated. Chromatography on silica gel (5% CH$_3$CN-DCM increasing to 30% CH$_3$CN +2% MeOH) afforded the title compound as an off white amorphous solid. $^1$H NMR (600 MHz, CDCl$_3$) δ 8.15 (d, J=1.9 Hz, 1H), 7.82 (d, J=8.6 Hz, 1H), 7.54 (dd, J=8.6, 2.0 Hz, 1H), 7.49 (d, J=8.2 Hz, 2H), 7.38 (d, J=8.1 Hz, 2H), 7.27 (s, 1H), 6.14 (d, J=4.6 Hz, 1H), 5.01 (s, 1H), 4.33 (s, 2H), 4.07 (s, 3H), 3.95 (s, 3H). MS (ESI): mass calcd. for C$_{22}$H$_{18}$ClF$_3$N$_4$O$_2$, 462.1, m/z found 463.1 [M+H]$^+$. Example 17a was purified by chiral SFC (Chiracel AD-H column (50× 250 mm, 5 micron), Mobile phase: 12% EtOH-hexane with 0.2% Et$_3$N). The first eluting enantiomer was Example 17b. The second eluting enantiomer was Example 17c.

Example 18a (4-Chloro-2-methoxy-3-(4-(trifluoromethyl)benzyl)quinolin-6-yl)(1-methyl-1H-imidazol-5-yl)methanol

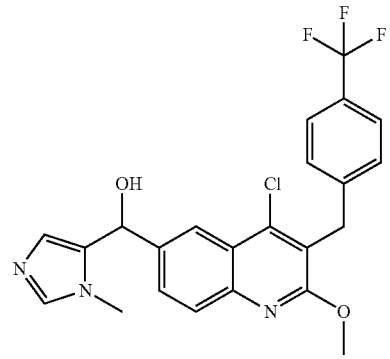 [SMILES: COc1nc2ccc(C(O)c3cncn3C)cc2c(Cl)c1Cc1ccc(C(F)(F)F)cc1]

To a flask containing 6-bromo-4-chloro-2-methoxy-3-(4-(trifluoromethyl)benzyl)quinoline (3.0 g, 6.97 mmol, Intermediate 10: step d) was added THF (40 ml) and the solution was cooled to −70° C. n-BuLi (2.5 M in hexanes, 2.8 mL, 7 mmol) was added dropwise. After 2 minutes, 1-methyl-1H-imidazole-5-carbaldehyde (1.2 g, 9 mmol, in 10 mL THF) was introduced. After 15 minutes, the dry-ice bath was replaced with a 0° C. bath. After 35 minutes the reaction mixture was quenched with aqueous NH$_4$Cl solution and the aqueous portion was extracted with EtOAc:THF (10:2) 5×50 mL. The combined organics were washed with brine, dried over Na$_2$SO$_4$, filtered and concentrated. Chromatography on silica gel (30% acetone-DCM increasing to 5% MeOH) provided the title compound. $^1$H NMR (500 MHz, CDCl$_3$) δ ppm 8.21 (s, 1H), 7.82 (d, J=8.6 Hz, 1H), 7.60 (dd, J=8.6, 1.9 Hz, 1H), 7.50 (d, J=8.2 Hz, 2H), 7.39 (d, J=8.1 Hz, 2H), 7.33 (s, 1H), 6.65 (s, 1H), 6.04 (s, 1H), 4.34 (s, 2H), 4.07 (s, 3H), 3.55 (s, 3H). MS (ESI): mass calcd. for C$_{23}$H$_{19}$ClF$_3$N$_3$O$_2$, 461.1, m/z found 462.1 [M+H]$^+$. Example 18a was purified by chiral SFC (Chiracel AD-H column (50×250 mm, 5 micron), Mobile phase: 15% EtOH-hexane with 0.2% Et$_3$N). The first eluting enantiomer was Example 18b. The second eluting enantiomer was Example 18c.

Example 19

(4-Chloro-2-methoxy-3-(4-(trifluoromethyl)benzyl) quinolin-6-yl)(2,4-dimethyloxazol-5-yl)methanol

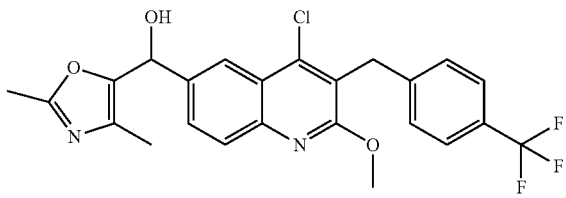 [SMILES: COc1nc2ccc(C(O)c3oc(C)nc3C)cc2c(Cl)c1Cc1ccc(C(F)(F)F)cc1]

To a flask containing 6-bromo-4-chloro-2-methoxy-3-(4-(trifluoromethyl)benzyl)quinoline (1.5 g, 3.48 mmol, Intermediate 10: step d) was added THF (65 mL) and the solution was cooled to −70° C. n-BuLi (2.5 M in hexanes, 1.62 mL, 4.04 mmol) was added dropwise. After 2 minutes, 2,4-dimethyloxazole-5-carbaldehyde (520 mg, 4.16 mmol in 3 mL THF) was introduced. After 25 minutes the reaction mixture was quenched with aqueous NH$_4$Cl solution and the aqueous portion was extracted with EtOAc (5×40 mL). The combined organics were washed with brine, dried over MgSO$_4$, filtered and concentrated. Chromatography on silica gel (10% CH$_3$CN-DCM increasing to 30% CH$_3$CN+1% MeOH) provided the title compound as a white amorphous solid. $^1$H NMR (500 MHz, CDCl$_3$) δ ppm 8.21 (d, J=1.9 Hz, 1H), 7.84 (d, J=8.6 Hz, 1H), 7.66 (dd, J=8.6, 1.8 Hz, 1H), 7.50 (d, J=8.1 Hz, 2H), 7.38 (d, J=8.0 Hz, 2H), 6.05 (d, J=4.6 Hz, 1H), 4.35 (s, 2H), 4.07 (s, 3H), 2.44 (d, J=4.6 Hz, 1H), 2.37 (s, 3H), 2.11 (s, 3H). MS (ESI): mass calcd. for C$_{24}$H$_{20}$ClF$_3$N$_2$O$_3$, 476.1, m/z found 477.1 [M+H]$^+$.

Example 20a (4-Chloro-2-methoxy-3-(4-(trifluoromethyl)benzyl) quinolin-6-yl)(3,5-dimethylisoxazol-4-yl)methanol

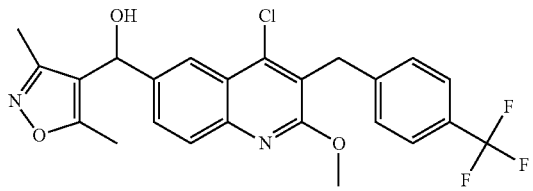 [SMILES: COc1nc2ccc(C(O)c3c(C)noc3C)cc2c(Cl)c1Cc1ccc(C(F)(F)F)cc1]

To a flask containing 6-bromo-4-chloro-2-methoxy-3-(4-(trifluoromethyl)benzyl)quinoline (2.0 g, 4.64 mmol, Intermediate 10: step d) was added THF (65 mL) at room temperature which resulted in a colorless homogeneous mixture. The solution was cooled to −70° C. which remained homogeneous and then n-BuLi (2.5 M in hexanes, 2.1 mL, 5.25 mmol) was added dropwise. The color of the solution became a dark opaque reddish-brown color. After 2 minutes, 3,5-dimethylisoxazole-4-carbaldehyde (705 mg, 5.63 mmol in 2 mL THF) was introduced. The reaction mixture immediately became a homogeneous yellow solution. After 25 minutes the reaction mixture was quenched with aqueous NH$_4$Cl solution and the aqueous layer was extracted with EtOAc (3×50 mL). The combined organics were washed with brine, dried over MgSO$_4$, filtered and concentrated to afford a faint yellow oil. FCC on silica gel (100% DCM increasing to 20% CH$_3$CN-DCM) afforded the title compound as an off white amorphous solid. $^1$H NMR (500 MHz, CDCl$_3$) δ ppm 8.17 (s, 1H), 7.82 (d, J=8.6 Hz, 1H), 7.56-7.48 (m, 3H), 7.39 (d, J=8.1 Hz, 2H), 5.96 (d, J=3.2 Hz, 1H), 4.35 (s, 2H), 4.07 (s, 3H), 2.34 (s, 3H), 2.32 (br. s, 1H), 2.10 (s, 3H). MS (ESI): mass calcd. for C$_{24}$H$_{20}$ClF$_3$N$_2$O$_3$, 476.1; m/z found, 476.9 [M+H]$^+$. Example 20a was purified by chiral SFC (Stationary phase: Chiralpak AD-H 5 μm 250×20 mm, Mobile phase: 70% CO$_2$, 30% mixture of MeOH/i-PrOH 50/50 v/v). The first eluting enantiomer was Example 20b and the second eluting enantiomer was Example 20c.

Example 21a (2-Azetidin-1-yl-4-chloro-3-[4-(1H-pyrazol-1-yl) benzyl]quinolin-6-yl)(1,2-dimethyl-1H-imidazol-5-yl)methanol

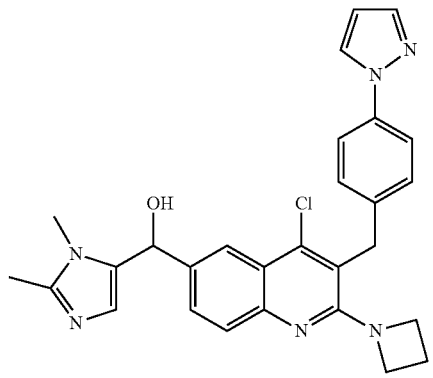 [SMILES: Cc1ncc(C(O)c2ccc3nc(N4CCC4)c(Cc4ccc(-n5cccn5)cc4)c(Cl)c3c2)n1C]

3-(4-(1H-Pyrazol-1-yl)benzyl)-2-(azetidin-1-yl)-6-bromo-4-chloroquinoline (1.03 g, 2.27 mmol, Intermediate 17) and THF (15 mL) were combined in the reaction vessel under an N$_2$ atmosphere and cooled to −78° C. in a dry ice acetone bath. n-BuLi (1.6 M in hexanes, 1.70 mL, 2.72 mmol) was then added dropwise via syringe over approximately one minute and contents were allowed to stir at −78° C. for an additional 5 minutes. 1,2-Dimethyl-1H-imidazole-5-carbaldehyde (0.31 g, 2.5 mmol) in THF (5 mL) was then cannulated into the reaction vessel and the reaction was stirred at −78° C. for 10 minutes. The dry ice bath was removed and replaced by an ice water bath and the reaction continued for approximately one hour at 0° C. The reaction was then quenched with a saturated, aqueous NH$_4$Cl solution, then transferred to a separatory funnel with EtOAc. The organic phase was separated and the aqueous layer was back extracted with EtOAc, then the combined organic layers were dried over MgSO$_4$, filtered and concentrated under reduced pressure. The crude product was purified by flash column chromatography (silica gel, 0-10% DCM/(10% of a 2 M NH$_3$ MeOH in DCM)) to provide the title compound. MS (ESI): mass calcd. for C$_{28}$H$_{27}$ClN$_6$O, 498.2; m/z found, 499.5 [M+H]$^+$. $^1$H NMR (400 MHz, CDCl$_3$) δ ppm 8.16-8.12 (m, 1H), 7.88 (dd, J=2.5, 0.6 Hz, 1H), 7.75 (d, J=8.6 Hz, 1H), 7.70 (dd, J=1.8, 0.6 Hz, 1H), 7.62-7.54 (m, 3H), 7.19 (d, J=8.5 Hz, 2H), 6.53 (s, 1H), 6.44 (dd, J=2.5, 1.8 Hz, 1H), 5.97 (s, 1H), 4.33 (s, 2H), 4.19-4.12 (m, 4H), 3.49 (s, 3H), 2.34 (s, 3H), 2.27-2.18 (m, 2H).

{2-Azetidin-1-yl-4-chloro-3-[4-(1H-pyrazol-1-yl)benzyl]quinolin-6-yl}(1,2-dimethyl-1H-imidazol-5-yl)methanol was purified via SFC with a Chiralpak AD-H column (5 μm 250×20 mm) using a mobile phase of 55% $CO_2$ and a 45% methanol (+0.3% i-$PrNH_2$) to provide two enantiomers. The first eluting enantiomer was Example 21b: MS (ESI): mass calcd. for $C_{28}H_{27}ClN_6O$, 498.2; m/z found, 499.5 $[M+H]^+$. $^1H$ NMR (400 MHz, $CDCl_3$) δ ppm 8.13 (s, 1H), 7.87 (d, J=2.5 Hz, 1H), 7.76-7.67 (m, 2H), 7.62-7.50 (m, 3H), 7.18 (d, J=8.2 Hz, 2H), 6.49 (s, 1H), 6.46-6.41 (m, 1H), 5.94 (s, 1H), 4.31 (s, 2H), 4.15 (t, J=7.5 Hz, 4H), 3.47 (s, 3H), 2.31 (s, 3H), 2.26-2.18 (m, 2H) and the second eluting enantiomer was Example 21c: MS (ESI): mass calcd. for $C_{28}H_{27}ClN_6O$, 498.2; m/z found, 499.5 $[M+H]^+$. $^1H$ NMR (400 MHz, $CDCl_3$) δ ppm 8.16-8.10 (m, 1H), 7.87 (d, J=2.5 Hz, 1H), 7.74 (d, J=8.6 Hz, 1H), 7.69 (d, J=1.8 Hz, 1H), 7.63-7.50 (m, 3H), 7.19 (d, J=8.2 Hz, 2H), 6.51 (s, 1H), 6.48-6.41 (m, 1H), 5.96 (s, 1H), 4.32 (s, 2H), 4.15 (t, J=7.5 Hz, 4H), 3.48 (s, 3H), 2.32 (s, 3H), 2.27-2.18 (m, 2H).

Example 22a

{2-Azetidin-1-yl-4-chloro-3-[4-(trifluoromethyl)benzyl]quinolin-6-yl}(1,2-dimethyl-1H-imidazol-5-yl)methanol

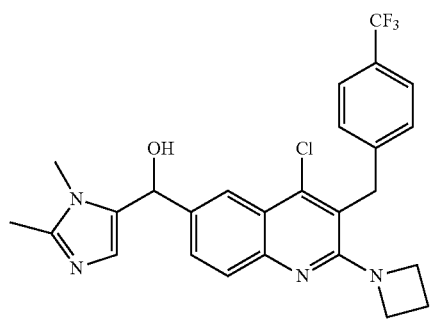 [SMILES: Cc1ncc(C(O)c2ccc3nc(N4CCC4)c(Cc4ccc(C(F)(F)F)cc4)c(Cl)c3c2)n1C]

2-(Azetidin-1-yl)-6-bromo-4-chloro-3-(4-(trifluoromethyl)benzyl)quinoline (1.00 g, 2.19 mmol, Intermediate 16) was dissolved in THF (20 mL) in a dry round bottom flask under an $N_2$ atmosphere, then cooled to −78° C. in dry ice acetone bath. n-BuLi (1.6 M in hexanes, 1.74 mL, 2.79 mmol) was then added dropwise via syringe over approximately 5 minutes. The contents were stirred at −78° C. for approximately 10 minutes, then a solution of 1,2-dimethyl-1H-imidazole-5-carbaldehyde (0.30 g, 2.4 mmol) in THF (20 mL) was added via cannula and stirred for 10 minutes at −78° C. The dry ice bath was then removed and replaced with an ice water bath and stirred at 0° C. for approximately one hour. The reaction was then quenched with a saturated, aqueous $NH_4Cl$ solution, then transferred to a separatory funnel with EtOAc. The organic phase was extracted with a saturated, aqueous $NH_4Cl$ solution and deionized water, then separated and dried over $MgSO_4$, filtered and concentrated under reduced pressure. The crude product was purified by flash column chromatography (silica gel, 0-10% DCM/(10% of a 2 M $NH_3$ MeOH in DCM) to provide the title compound. MS (ESI): mass calcd. for $C_{26}H_{24}ClF_3N_4O$, 500.2; m/z found, 501.4 $[M+H]^+$. $^1H$ NMR (600 MHz, $CDCl_3$) δ ppm 8.15-8.11 (m, 1H), 7.75 (d, J=8.6 Hz, 1H), 7.57 (dd, J=8.7, 2.0 Hz, 1H), 7.53 (d, J=8.2 Hz, 2H), 7.26-7.21 (m, 2H), 7.59-7.55 (m, 1H), 6.52 (d, 1H), 5.97 (s, 1H), 4.35 (s, 2H), 4.13 (t, J=7.5 Hz, 4H), 3.49 (s, 3H), 2.33 (s, 3H), 2.28-2.20 (m, 2H).

{2-Azetidin-1-yl-4-chloro-3-[4-(trifluoromethyl)benzyl]quinolin-6-yl}(1,2-dimethyl-1H-imidazol-5-yl)methanol was purified via SFC with a Chiralpak AD-H column (5 μm 250×20 mm) using a mobile phase of 60% $CO_2$ and a 40% isopropanol (+0.3% i-$PrNH_2$) to provide two enantiomers. The first eluting enantiomer was Example 22b: MS (ESI): mass calcd. for $C_{26}H_{24}ClF_3N_4O$, 500.2; m/z found, 501.4 $[M+H]^+$. $^1H$ NMR (600 MHz, $CDCl_3$) δ ppm 8.15-8.11 (m, 1H), 7.75 (d, J=8.6 Hz, 1H), 7.56 (dd, J=8.7, 2.0 Hz, 1H), 7.53 (d, J=8.0 Hz, 2H), 7.23 (d, J=8.0 Hz, 2H), 6.51 (s, 1H), 5.96 (s, 1H), 4.35 (s, 2H), 4.13 (t, J=7.5 Hz, 4H), 3.49 (s, 3H), 2.33 (s, 3H), 2.27-2.21 (m, 2H) and the second eluting enantiomer was Example 22c: MS (ESI): mass calcd. for $C_{26}H_{24}ClF_3N_4O$, 500.2; m/z found, 501.4 $[M+H]^+$. $^1H$ NMR (600 MHz, $CDCl_3$) δ ppm 8.12 (d, J=1.9 Hz, 1H), 7.74 (d, J=8.6 Hz, 1H), 7.56 (dd, J=8.7, 2.0 Hz, 1H), 7.53 (d, J=8.0 Hz, 2H), 7.23 (d, J=7.8 Hz, 2H), 6.50 (s, 1H), 5.96 (s, 1H), 4.35 (s, 2H), 4.13 (t, J=7.5 Hz, 4H), 3.48 (s, 3H), 2.32 (s, 3H), 2.29-2.20 (m, 2H).

Example 23a

{2-Azetidin-1-yl-4-chloro-3-[4-(trifluoromethyl)benzyl]quinolin-6-yl}(2,6-dimethylpyridin-3-yl)methanol

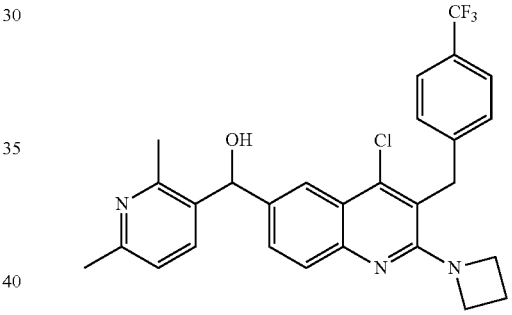

2-(Azetidin-1-yl)-6-bromo-4-chloro-3-(4-(trifluoromethyl)benzyl)quinoline (1.09 g, 2.40 mmol, Intermediate 16) was dissolved in THF (20 mL) in a dry round bottom flask under an $N_2$ atmosphere, then cooled to −78° C. in dry ice acetone bath. n-BuLi (1.6 M in hexanes, 1.74 mL, 2.79 mmol) was then added dropwise via syringe over approximately 5 minutes. The contents were stirred at −78° C. for approximately 10 minutes, then a solution of 2,6-dimethyl-pyridine-3-carbaldehyde (0.36 g, 2.6 mmol) in THF (20 mL) was added via cannula and stirred for 10 minutes at −78° C. The dry ice bath was then removed and replaced with an ice water bath and stirred at 0° C. for approximately one hour. The reaction was then quenched with a saturated, aqueous $NH_4Cl$ solution then transferred to a separatory funnel with EtOAc. The organic phase was extracted with a saturated, aqueous $NH_4Cl$ solution and deionized water, then separated and dried over $MgSO_4$, filtered and concentrated under reduced pressure. The crude product was purified by flash column chromatography (silica gel, 0-100% DCM/(10% of a 2 M $NH_3$ MeOH in DCM)) to afford the title compound. MS (ESI): mass calcd. for $C_{28}H_{25}ClF_3N_3O$, 511.2; m/z found, 512.5 $[M+H]^+$. $^1H$ NMR (400 MHz, $CDCl_3$) δ ppm 7.99 (d, J=2.0 Hz, 1H), 7.75 (d, J=7.9 Hz, 1H), 7.69 (d, J=8.6 Hz, 1H), 7.53 (d, J=8.1 Hz, 2H), 7.44 (dd, J=8.7, 2.0 Hz, 1H), 7.24-7.18 (m, 2H), 7.04 (d, J=7.9 Hz, 1H), 6.09 (s, 1H), 4.34 (s, 2H), 4.12 (t, J=7.6 Hz, 4H), 2.74 (s, 1H), 2.51 (s, 3H), 2.46 (s, 3H), 2.29-2.18 (m, 2H).

{2-Azetidin-1-yl-4-chloro-3-[4-(trifluoromethyl)benzyl]quinolin-6-yl}(1,2-dimethyl-1H-imidazol-5-yl)methanol was purified via SFC with a Chiralpak AD-H column (5 m 250×20 mm) using a mobile phase of 60% CO$_2$ and a 40% isopropanol (+0.3% i-PrNH$_2$) to provide two enantiomers. The first eluting enantiomer was Example 23b: MS (ESI): mass calcd. for C$_{28}$H$_{25}$ClF$_3$N$_3$O, 511.2; m/z found, 512.3 [M+H]$^+$. $^1$H NMR (400 MHz, CDCl$_3$) δ ppm 7.97 (d, J=1.9 Hz, 1H), 7.76 (d, J=7.9 Hz, 1H), 7.67 (d, J=8.6 Hz, 1H), 7.53 (dd, J=8.3, 1.0 Hz, 2H), 7.42 (dd, J=8.7, 2.0 Hz, 1H), 7.24-7.19 (m, 2H), 7.04 (d, J=7.9 Hz, 1H), 6.07 (s, 1H), 4.34 (s, 2H), 4.18-4.06 (m, 4H), 2.51 (s. 3H), 2.45 (s, 3H), 2.23 (p, J=7.5 Hz, 2H) and the second eluting enantiomer was Example 23c: MS (ESI): mass calcd. for C$_{28}$H$_{25}$ClF$_3$N$_3$O, 511.2; m/z found, 512.3 [M+H]$^+$. $^1$H NMR (400 MHz, CDCl$_3$) δ ppm 7.96 (d, J=1.9 Hz, 1H), 7.76 (d, J=7.9 Hz, 1H), 7.66 (d, J=8.7 Hz, 1H), 7.53 (d, J=8.0 Hz, 2H), 7.42 (dd, J=8.7, 2.0 Hz, 1H), 7.24-7.19 (m, 2H), 7.03 (d, J=7.9 Hz, 1H), 6.06 (s, 1H), 4.34 (s, 2H), 4.17-4.08 (m, 4H), 2.51 (s, 3H), 2.44 (s, 3H), 2.27-2.18 (m, 2H).

Example 24

(3-Benzyl-2,4-dichloroquinolin-6-yl)(pyridine-4-yl)methanol.TFA

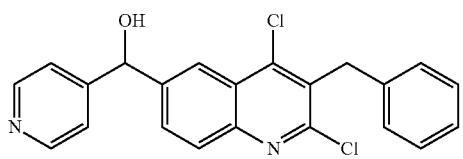 [SMILES: OC(c1ccncc1)c1ccc2nc(Cl)c(Cc3ccccc3)c(Cl)c2c1]

A solution of n-butyllithium (1.6 M in hexanes, 0.34 mL, 0.54 mmol) was added to a solution of 3-benzyl-6-bromo-2,4-dichloroquinoline (0.200 g, 0.545 mmol, Intermediate 6: step c) in THF (9.6 mL) at −78° C. and stirred for 1 minute. Then, isonicotinaldehyde (0.058 g, 0.545 mmol) was added and the reaction was warmed to room temperature. A solution of saturated aqueous sodium bicarbonate was added and the crude product was extracted with ethyl acetate and evaporated in vacuo. The crude product was purified via reverse phase HPLC (H$_2$O/acetonitrile/1% TFA) to provide the title compound. $^1$H NMR (400 MHz, DMSO-d$_6$) δ ppm 8.70 (br. s., 2H), 8.39 (s, 1H), 8.01 (d, 0.1=8.59 Hz, 1H), 7.89 (dd, J=2.02, 8.59 Hz, 1H), 7.83 (d, J=5.56 Hz, 2H), 7.26-7.34 (m, 2H), 7.19-7.25 (m, 1H), 7.17 (d, J=7.07 Hz, 2H), 6.21 (s, 1H), 4.48 (s, 2H); MS (ESI) 395.1 (M+H)$^+$.

Example 25

(2,4-Dichloro-3-phenylquinolin-6-yl)(pyridin-4-yl)methanol.TFA

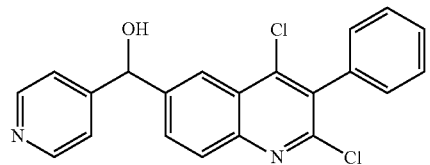 [SMILES: OC(c1ccncc1)c1ccc2nc(Cl)c(-c3ccccc3)c(Cl)c2c1]

A solution of n-butyllithium (1.6 M in hexanes, 0.177 mL, 0.283 mmol) was added to a solution of 6-bromo-2,4-dichloro-3-phenylquinoline (0.100 g, 0.283 mmol, Intermediate 1: step c) in THF (5 mL) at −78° C. and stirred for 1 minute. Then, isonicotinaldehyde (0.030 g. 0.283 mmol) was added and the reaction was warmed to room temperature. A solution of saturated aqueous sodium bicarbonate was added and the crude product was extracted with ethyl acetate and evaporated in vacuo. The crude product was purified twice via reverse phase HPLC (H$_2$O/acetonitrile/1% TFA) to provide the title compound. $^1$H NMR (400 MHz, CDCl$_3$) δ ppm 8.88 (br. s., 2H), 8.33 (s, 1H), 8.12 (d, J=8.59 Hz, 1H), 8.04 (br. s., 2H), 7.71 (d, J=9.09 Hz, 1H), 7.49-7.63 (m, 3H), 7.30-7.38 (m, 2H), 6.25 (s, 1H); MS (ESI) 381.0 (M+H)$^+$.

Example 26

(4-Chlorophenyl)(2,4-dichloro-3-(2-chlorophenyl)quinolin-6-yl)methanol

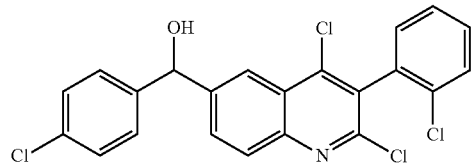 [SMILES: OC(c1ccc(Cl)cc1)c1ccc2nc(Cl)c(-c3ccccc3Cl)c(Cl)c2c1]

n-BuLi (2.5 M in hexanes, 0.52 mL, 1.3 mmol) was added dropwise to a solution of 6-bromo-2,4-dichloro-3-(2-chlorophenyl)quinolone (387.5 mg. 1 mmol, Intermediate 2: step c) in dry THF (10 mL) in a 100 mL three necked round bottomed flask at −78° C. under N$_2$. Stirring was continued for 30 minutes then a solution of 4-chlorobenzaldehyde (140.5 mg. 1 mmol) in dry THF (10 mL) was added at −78° C. The cooling bath was removed and the mixture was gradually warmed up to room temperature and stirred for 2 hours. The mixture was quenched by adding H$_2$O (10 mL) and then extracted with CH$_2$Cl$_2$ (2×50 mL). The combined organic phase was dried over Na$_2$SO$_4$, filtered, and concentrated to dryness and purified by prep-TLC (developed by petroleum ether/EtOAc=1:1) to provide the title compound as a white solid. MS (ESI): mass calcd. for C$_{22}$H$_{13}$Cl$_4$NO 447, m/z found 447.9 [M+H]$^+$. $^1$H NMR (300 MHz, CD$_3$OD) δ ppm 8.38 (s, 1H), 7.98 (d, J=8.8 Hz, 1H), 7.88-7.81 (m, 1H), 7.64-7.56 (m, 1H), 7.49 (d, J=4.4 Hz, 2H), 7.45-7.30 (m, 5H), 6.02 (s, 1H).

Example 27

(3-(4-(1H-Pyrazol-1-yl)benzyl)-4-chloro-2-methoxyquinolin-6-yl)(1,2-dimethyl-1H-imidazol-5-yl)methanol

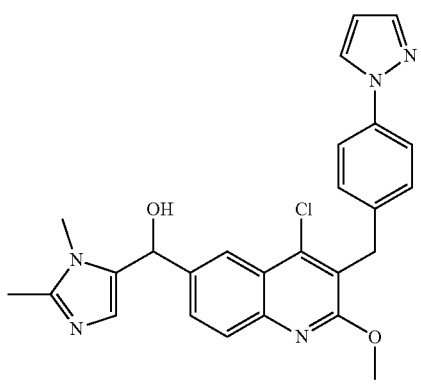 [SMILES: COc1nc2ccc(C(O)c3cnc(C)n3C)cc2c(Cl)c1Cc1ccc(-n2cccn2)cc1]

A solution of n-butyllithium in hexanes (1.6 M, 1.5 mL, 2.3 mmol) was added dropwise to a stirring solution of 3-(4-(1H-pyrazol-1-yl)benzyl)-6-bromo-4-chloro-2-methoxyquinoline (1 g, 2.3 mmol, Intermediate 4: step d) in tetrahydrofuran (18 mL) at −78° C. After 3 minutes, a solution of 1,2-dimethyl-1H-imidazole-5-carbaldehyde (347 mg, 2.8 mmol) in tetrahydrofuran (5 mL) was added dropwise. After 5 minutes, the flask was placed into an ice-water bath. After 30 minutes, water (10 mL) was added and the biphasic mixture was allowed to warm to 23° C. The mixture was partitioned between half-saturated sodium chloride solution (50 mL) and ethyl acetate (100 mL). The layers were separated. The organic layer was dried with sodium sulfate and the dried solution was filtered. Silica gel (3 g) was added to the filtrate and the solvent was removed by rotary evaporation to afford a free-flowing powder. The powder was loaded onto a column of silica gel for purification. Elution with ethyl acetate initially, grading to 7% methanol-ethyl acetate provided the title compound as an off-white solid. $^1$H NMR (500 MHz, CDCl$_3$) δ ppm 8.24-8.22 (m, 1H), 7.86-7.84 (m, 1H), 7.82 (d. J=8.6 Hz, 1H), 7.68 (d, J=1.7 Hz, 1H), 7.62-7.59 (m, 1H), 7.58-7.54 (m, 2H), 7.38-7.35 (m, 2H), 6.54 (s, 1H), 6.44-6.41 (m, 1H), 6.00 (s, 1H), 4.33 (s, 2H), 4.09 (s, 3H), 3.47 (s, 3H), 2.33 (s, 3H); MS (ESI): mass calcd. for C$_{26}$H$_{24}$ClN$_5$O$_2$, 473.2; m/z found, 474.0 [M+H]$^+$.

Example 28

(4-Chloro-2-ethyl-3-(4-(trifluoromethyl)benzyl)quinolin-6-yl)(1,2-dimethyl-1H-imidazol-5-yl)methanol

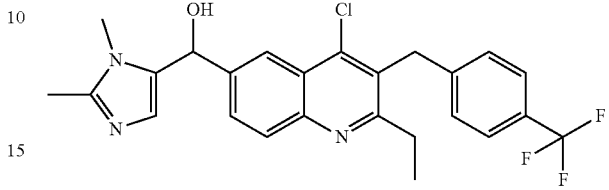

A solution of n-butyllithium in hexanes (2.5 M, 0.37 mL, 0.92 mmol) was added dropwise to a stirring solution of 6-bromo-4-chloro-2-ethyl-3-(4-(trifluoromethyl)benzyl)quinoline (393 mg, 0.917 mmol, Intermediate 5: step c) in tetrahydrofuran (7 mL) at −78° C. After 2 minutes, a solution of 1,2-dimethyl-1H-imidazole-5-carbaldehyde (125 mg, 1.01 mmol) in tetrahydrofuran (2 mL) was added dropwise. After 5 minutes, the flask was placed into an ice-water bath. After 30 minutes, water (5 mL) was added and the biphasic mixture was allowed to warm to 23° C. The mixture was partitioned between half-saturated sodium chloride solution (25 mL) and ethyl acetate (50 mL). The layers were separated. The organic layer was dried with sodium sulfate and the dried solution was filtered. Silica gel (5 g) was added to the filtrate and the solvent was removed by rotary evaporation to afford a free-flowing powder. The powder was loaded onto a column of silica gel for purification. Elution with dichloromethane initially, grading to 7% methanol-dichloromethane provided the title compound as an off-white solid. $^1$H NMR (400 MHz, CDCl$_3$) δ ppm 8.37-8.33 (m, 1H), 8.04 (d, J=8.7 Hz, 1H), 7.72-7.66 (m, 1H), 7.52 (d, J=7.9 Hz, 2H), 7.20 (d, J=7.9 Hz, 2H), 6.53 (s, 1H), 6.05 (s, 1H), 4.50 (s, 2H), 3.50 (s, 3H), 2.97-2.89 (m, 2H), 2.33 (s, 3H), 1.34-1.28 (m, 3H); MS (ESI): mass calcd. for C$_{25}$H$_{23}$ClF$_3$N$_3$O, 473.1; m/z found, 474.1 [M+H]$^+$.

Example 29

(4-Chloro-2-methoxy-3-((6-(trifluoromethyl)pyridin-3-yl)methyl)quinolin-6-yl)(1,2-dimethyl-1H-imidazol-5-yl)methanol

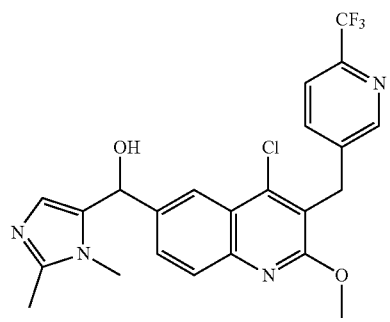 [SMILES: COc1nc2ccc(C(O)c3cnc(C)n3C)cc2c(Cl)c1Cc1ccc(C(F)(F)F)nc1]

A solution of n-BuLi (2.5 M in hexanes, 0.9 mL, 2.25 mmol) was added dropwise by syringe to a solution of 6-bromo-4-chloro-2-methoxy-3-((6-(trifluoromethyl)pyridin-3-yl)methyl)quinoline (1.009 g, 2.338 mmol, Intermediate 9: step c) in dry THF (12.5 mL) in a dry ice-acetone bath. After 1-2 minutes, a solution of 1,2-dimethyl-1H-imidazole-5-carbaldehyde (359.6 mg, 2.897 mmol) in dry THF (5 mL) was added dropwise. The reaction was stirred for 10 minutes, then was moved into an ice bath and allowed to warm to room temperature. The reaction was quenched with saturated aqueous ammonium chloride. Water was added and the separated aqueous layer was extracted with EtOAc/THF 10:1. The organic phase was dried ($Na_2SO_4$), filtered, and concentrated. The crude was triturated with EtOAc/ether 1:1 and filtered, rinsing with additional ether. The collected solids were purified by flash column chromatography (silica gel, 0-5% MeOH-DCM) to provide the title compound. $^1$H NMR (500 MHz, $CDCl_3$) δ ppm 8.76 (d, J=2.0 Hz, 1H), 8.24-8.22 (m, 1H), 7.84 (d, J=8.6 Hz, 1H), 7.79-7.75 (m, 1H), 7.67-7.62 (m, 1H), 7.56 (dd, J=8.2, 0.9 Hz, 1H), 6.54 (d, J=0.7 Hz, 1H), 6.03 (s, 1H), 4.37 (s, 2H), 4.09 (s, 3H), 3.49 (s, 3H), 2.35 (s, 3H); MS m/e 477.0 [M+H]$^+$.

Example 30

(4-Chloro-2-methoxy-3-((6-(trifluoromethyl)pyridin-3-yl)methyl)quinolin-6-yl)(2,6-dimethylpyridin-3-yl)methanol

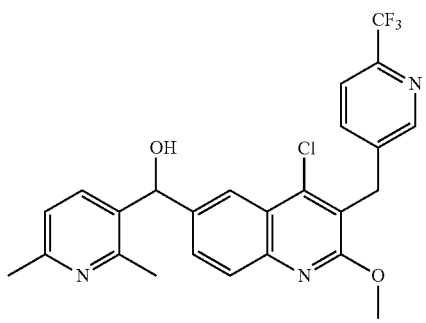 [SMILES: COc1nc2ccc(C(O)c3ccc(C)nc3C)cc2c(Cl)c1Cc1ccc(C(F)(F)F)nc1]

A solution of n-BuLi (2.5 M in hexanes, 1.6 mL, 4.0 mmol) was added dropwise by syringe to a solution of 6-bromo-4-chloro-2-methoxy-3-((6-(trifluoromethyl)pyridin-3-yl)methyl)quinoline (1.711 g, 3.964 mmol, Intermediate 9: step c) in dry THF (20 mL) in a dry ice-acetone bath.

After 1-2 minutes, a solution of 2,6-dimethylnicotinaldehyde (0.8 mL, 6.3 mmol) in dry THF (6 mL) was added dropwise. The reaction was stirred for 5 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The organic phase was dried ($Na_2SO_4$), filtered, and concentrated. The crude product was purified by flash column chromatography (silica gel, 0-3% MeOH-DCM) to provide the title compound. $^1$H NMR (500 MHz, $CDCl_3$) δ ppm 8.74 (d, J=2.0 Hz, 1H), 8.13 (dt, J=1.8, 0.7 Hz, 1H), 7.79 (d, J=8.6 Hz, 1H), 7.76-7.73 (m, 1H), 7.69 (d, J=7.9 Hz, 1H), 7.57-7.54 (m, 1H), 7.53 (dd, J=8.7, 2.0 Hz, 1H), 7.04 (d, J=7.9 Hz, 1H), 6.16 (d, J=3.3 Hz, 1H), 4.36 (s, 2H), 4.07 (s, 3H), 2.52 (s, 3H), 2.49 (s, 3H); MS m/e 488.0 [M+H]$^+$.

Example 31

(4-Chloro-3-(4-fluorobenzyl)-2-methoxyquinolin-6-yl)(2,6-dimethylpyridin-3-yl)methanol

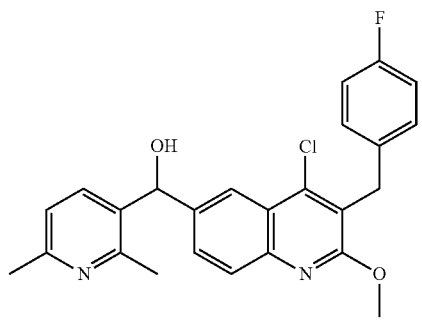 [SMILES: COc1nc2ccc(C(O)c3ccc(C)nc3C)cc2c(Cl)c1Cc1ccc(F)cc1]

A solution of n-BuLi (2.5 M in hexanes, 0.84 mL, 2.1 mmol) was added dropwise by syringe to a solution of 6-bromo-4-chloro-3-(4-fluorobenzyl)-2-methoxyquinoline (0.826 g, 2.17 mmol, Intermediate 7: step d) in dry THF (11 mL) in a dry ice-acetone bath. After 1-2 minutes, a solution of 2,6-dimethylnicotinaldehyde (0.23 mL, 1.8 mmol) in dry THF (3 mL) was added dropwise. The reaction was stirred for 5 minutes, then was removed from the cold bath and allowed to warm to room temperature. The reaction was quenched with saturated aqueous ammonium chloride. The mixture was partitioned between water and dichloromethane. The separated aqueous phase was further extracted with dichloromethane. The combined organic phases were dried ($Na_2SO_4$), filtered, and concentrated. The crude product was purified by flash column chromatography (silica gel, 0-3% MeOH-DCM) to provide the title compound. $^1$H NMR (500 MHz, $CDCl_3$) δ ppm 8.06 (d, J=1.9 Hz, 1H), 7.73 (d, J=8.6 Hz, 1H), 7.68 (d, J=7.9 Hz, 1H), 7.45 (dd, J=8.6, 2.0 Hz, 1H), 7.26-7.21 (m, 2H), 6.97 (d, J=7.9 Hz, 1H), 6.94-6.89 (m, 2H), 6.07 (s, 1H), 4.22 (s, 2H), 4.05 (s, 3H), 3.77 (s, 1H), 2.46 (s, 3H), 2.40 (s, 3H).

Example 32 tert-Butyl-3-((4-chloro-2-methoxy-3-(4-(trifluoromethyl)benzyl)quinolin-6-yl)(hydroxy)methyl)azetidine-1-carboxylate $CF_3$

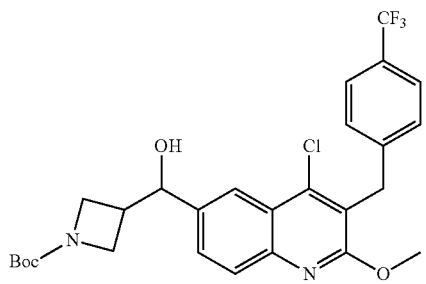 [SMILES: COc1nc2ccc(C(O)C3CN(C(=O)OC(C)(C)C)C3)cc2c(Cl)c1Cc1ccc(C(F)(F)F)cc1]

To a flask containing 6-bromo-4-chloro-2-methoxy-3-(4-(trifluoromethyl)benzyl)quinoline (1.0 g, 2.32 mmol. Intermediate 10: step d) was added THF (30 mL) resulting in a colorless homogeneous mixture. The solution was cooled to −70° C. and then n-BuLi (2.5 M in hexanes, 1.08 mL, 2.69 mmol) was added dropwise. The color of the solution became a dark opaque reddish-brown color. After 2 minutes, tert-butyl 3-formylazetidine-1-carboxylate (545 mg, 2.94 mmol) in 3 mL THF was introduced. After 5 minutes, the reaction mixture was placed in an ice-water bath and allowed to stir for 30 minutes at which time the mixture was quenched with aqueous NH$_4$Cl solution. The contents were diluted further with water and extracted with EtOAc (5×40 mL). The combined organics were washed with brine, dried over MgSO$_4$, filtered and concentrated to provide a yellow foam. The crude material was chromatographed on silica gel (20% EtOAc-hexanes increasing to 50% EtOAc) to provide the title compound as a white solid. $^1$H NMR (500 MHz, CDCl$_3$) δ ppm 8.06 (d, J=1.7 Hz, 1H), 7.84 (d, J=8.6 Hz, 1H), 7.63 (dd, J=8.6, 1.9 Hz, 1H), 7.50 (d, J=8.2 Hz, 2H), 7.38 (d, J=8.1 Hz, 2H), 4.99 (dd, J=8.0, 3.3 Hz, 1H), 4.35 (s, 2H), 4.05 (bs, 2H), 3.82 (t, J=8.7 Hz, 1H), 3.74-3.67 (m, 1H), 2.99-2.90 (m, 1H), 2.20-2.15 (m, 1H), 1.41 (s, 9H). MS (ESI): mass calcd. for C$_{27}$H$_{28}$ClF$_3$N$_2$O$_4$: 536.2, m/z found 537.2 [M+H]$^+$.

Example 33

(2,4-Dichloro-3-phenylquinolin-6-yl)(3-methylisoxazol-5-yl)methanol

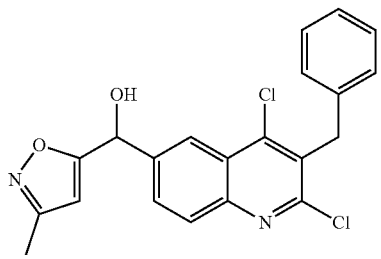 [SMILES: Cc1cc(C(O)c2ccc3nc(Cl)c(Cc4ccccc4)c(Cl)c3c2)on1]

To a mixture of 6-bromo-2,4-dichloro-3-phenylquinoline (363 mg, 1.03 mmol, Intermediate 1: step c) and 3-methylisoxazole-5-carbaldehyde (149 mg, 1.34 mmol) in THF (5 mL) at −78° C. was added n-BuLi (1.6 M in hexane, 0.707 mL, 1.13 mmol) dropwise. The mixture was stirred at −78° C. for 30 minutes, then moved to an ice bath and stirred for 30 minutes. The reaction was quenched by addition of saturated aqueous NH$_4$Cl and was diluted with water. The mixture was extracted three times with EtOAc. The organic phase was dried (Na$_2$SO$_4$), filtered, and concentrated to afford the crude title compound. MS (ESI): 385.0 [M+H]+.

Example 34a (4-Chloro-2-methoxy-3-(4-(trifluoromethyl)benzyl)quinolin-6-yl)(1,3,5-trimethyl-1H-pyrazol-4-yl)methanol

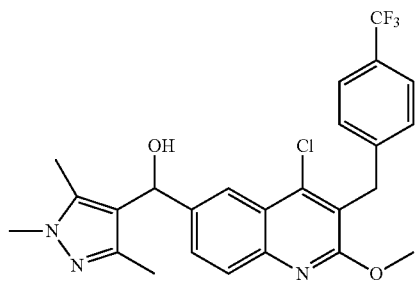

To a flask containing 6-bromo-4-chloro-2-methoxy-3-(4-(trifluoromethyl)benzyl)quinoline (1.37 g, 3.86 mmol, Intermediate 10: step d) was added THF (45 mL) at room temperature which resulted in a colorless homogeneous mixture. The solution was cooled to −78° C. and then n-BuLi (2.5 M in hexanes, 1.8 mL, 4.5 mmol) was added dropwise. The color of the solution became a reddish-brown color. After 4 minutes, 1,3,5-trimethyl-1H-pyrazole-4-carbaldehyde (300 mg, 2.17 mmol, in 3 mL THF) was introduced and the color of the mixture changed from reddish-brown to a yellow-greenish color over 5 minutes. The mixture was allowed to warm to 0° C. over 45 minutes at which time the reaction was quenched with aqueous NH$_4$Cl solution. The mixture was diluted further with water and extracted with EtOAc (3×150 mL). The combined organics were washed with brine, dried over MgSO$_4$, filtered and concentrated to give a light orange foam. FCC on silica gel (2% MeOH-DCM increasing to 8% MeOH-DCM) afforded the title compound as a light yellow amorphous solid. $^1$H NMR (500 MHz, CDCl$_3$) δ ppm 8.23 (s, 1H), 7.78 (d, J=8.6 Hz, 1H), 7.56-7.47 (m, 3H), 7.40 (d, J=8.1 Hz, 2H), 6.01 (d, J=3.0 Hz, 1H), 4.35 (s, 2H), 4.06 (s, 3H), 3.70 (s, 3H), 2.14 (s, 3H), 2.12 (s, 3H), 2.09 (d, J=3.3 Hz, 1H). MS (ESI): mass calcd. for C$_{25}$H$_{23}$ClF$_3$N$_3$O$_2$, 489.1; m/z found, 490.1 [M+H]$^+$. Example 34a was purified by chiral SFC (Stationary phase: Chiralpak AD-H 5 μm 250×21 mm, Mobile phase: 15% EtOH+0.2% TEA, 85% CO$_2$). The first eluting enantiomer was Example 34b and the second eluting enantiomer was Example 34c.

Example 35

(4-Chlorophenyl)(2,4-dichloro-3-phenylquinolin-6-yl)methanol

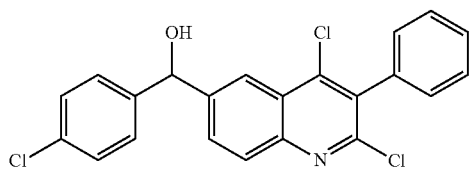 [SMILES: OC(c1ccc(Cl)cc1)c1ccc2nc(Cl)c(-c3ccccc3)c(Cl)c2c1]

n-Butyllithium (1.6 M in hexane, 0.292 mL, 0.467 mmol) was added to a solution of 6-bromo-2,4-dichloro-3-phenylquinoline (150 mg, 0.425 mmol, Intermediate 1: step c) in THF (1.5 mL) at −78° C. under a nitrogen atmosphere. The mixture was stirred at −78° C. for 5 minutes before addition of a solution of 4-chlorobenzaldehyde (89.6 mg, 0.637 mmol) in THF (1.2 mL) via cannula. The mixture was stirred at −78° C. for 25 minutes, then was quenched by addition of saturated aqueous NH$_4$Cl solution. The mixture was diluted with water and extracted with EtOAc (3×). The organic phase was dried (Na$_2$SO$_4$), filtered, and concentrated. The residue was purified by flash column chromatography (10% EtOAc-heptanes) to provide the title compound. $^1$H NMR (400 MHz, CDCl$_3$) δ ppm 8.35 (s, 1H), 8.03 (d, J=8.80 Hz, 1H), 7.71 (dd, J=1.71, 8.80 Hz, 1H), 7.45-7.60 (m, 3H), 7.30-7.41 (m, 6H), 6.05 (d, J=3.18 Hz, 1H), 2.44 (d, J=3.42 Hz, 1H); MS m/e 414/415.8 [M+H]$^+$.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants (K$_D$).

In a ThermoFluor® experiment where protein stability is monitored as the temperature is steadily increased, an equilibrium binding ligand causes the midpoint of an unfolding transition (T$_m$) to occur at a higher temperature. The shift in the melting point described as a ΔT$_m$ is proportional to the concentration and affinity of the ligand. The compound potency may be compared as a rank order of either ΔT$_m$ values at a single compound concentration or in terms of K$_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./minute for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt T$_m$: 47.8° C.
ΔH$_{(Tm)}$=115 kcal/mol
ΔC$_{p(Tm)}$=3 kcal/mol Cell Based Biological Data Compounds were assessed for RORgt functional modulation using either the RORgt ligand binding domain (LBD) reporter assay, or the RORgt full-length (FL) reporter assay. Data from either assay can be used to demonstrate functional modulation of RORgt activity by compounds RORγt (LBD) Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the *renilla luciferase* gene under control of the SV40 promoter. *Renilla luciferase* expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 μg of pBIND-RORγt LBD or pBIND-RORγt LBD-AF2 and 5 μg pGL4.31 (Promega Cat no. C935A) using Fugene 6 (Invitrogen Cat no. E2691) at a 1:6 ratio of DNA: Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 μL 1× Glo Lysis Buffer (Promega). Dual Glo Luciferase Reagent (50 μL/well) was then added and firefly luciferase luminescence was read on an Envision after a ten minute incubation. Finally, Stop and Glo reagent (50 μL/well) was added and *renilla luciferase* luminescence was read on an Envision after a ten minute incubation. To calculate the effect of compounds on RORγt activity, the ratio of firefly to *renilla luciferase* was determined and plotted against compound concentration. Agonist compounds increase RORγt-driven luciferase expression, and antagonist or inverse agonist compounds decrease luciferase expression.

RORγt (Full-Length Human) Reporter Assay

A reporter assay was used to test functional activity of RORγt modulatory compounds on transcriptional activation driven by full-length human RORγt. Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2× GAL4) and *Renilla luciferase* reporter under control of CMV promoter (pRL-CMV, Promega #E2261). The full-length coding sequence was used for human RORγt, i.e., nucleotides 142-1635 of human RORγt, transcript variant 2, NCBI Accession: NM_001001523.1 (SEQ ID NO: 1). HEK293T cells were plated at 35000 per well in 96-well plate in medium of MEM with 8.6% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.1% and DMSO 0.1%. After overnight (16 to 20 hours) incubation, media were removed and cells were lysed with 20 μL 1× Passive Lysis Buffer (Promega) for 10-15 minutes. Luminescence was measured using a BMG LUMIstar OPTIMA plate reader, after addition of 75 μL/well firefly luciferase buffer, followed by 75 μL/well *Renilla luciferase* buffer. To calculate the effect of compounds on RORγt activity, firefly values were normalized against values of DMSO only and values of reference compound at saturating concentration, then further normalized against *Renilla* signals. IC50s were generated by plotting final *Renilla* normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation.

Total CD4+ T cells were isolated from the peripheral blood mononuclear cells (PBMC) of healthy donors using a CD4+ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor ® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, $IC_{50}$ (μM) |
|---|---|---|---|---|---|---|
| 1 | 0.55 | >6 | 48 | ND | ND | ND |
| 2 | 1.6 | >6 | 12 | ND | ND | ND |
| 3 | 0.45 | ND | ND | ND | ND | ND |
| 4 | 4.9 | >6 | −1 | ND | ND | ND |
| 5a | 0.2 | 0.48 | 97 | ND | ND | ND |
| 5b | 0.069 | 0.27 | 98 | ND | ND | 1.5 |
| 5c | 0.091 | 0.3 | 97 | ND | ND | 0.61 |
| 6 | 0.22 | 0.79 | 95 | ND | ND | ND |
| 7 | 0.48 | ~2 | 93 | ND | ND | ND |
| 8a | 0.18 | >6 | 40 | ND | ND | ND |
| 8b | 0.18 | >6 | 31 | ND | ND | ND |
| 8c | 0.095 | >6 | 37 | ND | ND | ND |
| 9 | 0.68 | ND | ND | 0.15 | 42* | ND |

TABLE 1-continued

| Example Number | ThermoFluor® Assay, Kd (μM) | RORγt (LBD) Reporter Assay, IC50 (μM) | RORγt (LBD) Reporter Assay, % inhibition @ 6 μM | RORγt (FL) Reporter Assay, IC50 (μM) | RORγt (FL) Reporter Assay, % inhibition @ 2 μM | Human Th17 Assay, IC$_{50}$ (μM) |
|---|---|---|---|---|---|---|
| 10 | 3 | ~6 | 59 | ND | ND | ND |
| 11 | 0.15 | >6 | 24 | ND | ND | ND |
| 12 | 0.6 | ~1 | 92 | ND | ND | ND |
| 13 | 1.2 | >6 | 43 | ND | ND | ND |
| 14a | 0.071 | ND | ND | ND | ND | ND |
| 14b | 0.13 | 0.12 | 97 | ND | ND | 0.17 |
| 14c | 0.1 | 0.22 | 98 | ND | ND | 0.1 |
| 15a | 0.074 | 0.043 | 101 | ND | ND | ND |
| 15b | 0.069 | ~1 | 100 | 0.091 | 85* | 0.12 |
| 15c | 0.04 | 0.08 | 101 | 0.058 | 96 | 0.13 |
| 16 | 4.8 | 1.9 | 88 | ND | ND | ND |
| 17a | 0.064 | 0.31 | 99 | ND | ND | ND |
| 17b | 0.081 | 0.24 | 96 | ND | ND | 0.44 |
| 17c | 0.13 | 0.21 | 97 | ND | ND | 0.14 |
| 18a | 0.24 | 0.38 | 96 | ND | ND | ND |
| 18b | 0.29 | 0.51 | 98 | ND | ND | ND |
| 18c | 0.26 | 0.32 | 96 | ND | ND | 0.65 |
| 19 | 0.35 | 0.24 | 79 | ND | ND | ND |
| 20a | 0.086 | ND | ND | 0.052 | 97 | ND |
| 20b | 0.29 | ND | ND | 0.3 | 84 | ND |
| 20c | 0.022 | ND | ND | 0.023 | 99 | ND |
| 21a | 0.2 | 0.38 | 91 | ND | ND | ND |
| 21b | 0.26 | 0.69 | 88 | ND | ND | ND |
| 21c | 0.19 | 0.45 | 92 | ND | ND | 2.6 |
| 22a | 0.081 | 0.25 | 92 | ND | ND | ND |
| 22b | 0.055 | 0.24 | 95 | ND | ND | 0.0094 |
| 22c | 0.043 | ~0.4 | 96 | ND | ND | 0.0029 |
| 23a | 0.14 | 0.18 | 95 | ND | ND | ND |
| 23b | 0.11 | 0.22 | 98 | ND | ND | 0.38 |
| 23c | 0.2 | 0.28 | 99 | ND | ND | 0.48 |
| 24 | 0.23 | >6 | 41 | ND | ND | ND |
| 25 | 1.2 | >6 | 47 | ND | ND | ND |
| 26 | 1.4 | ~3 | 68 | ND | ND | ND |
| 27 | ND | ND | ND | ND | ND | ND |
| 28 | ND | ND | ND | ND | ND | ND |
| 29 | ND | ND | ND | ND | ND | ND |
| 30 | ND | ND | ND | ND | ND | ND |
| 31 | ND | ND | ND | ND | ND | ND |
| 32 | 16 | 2.2 | 84 | ND | ND | ND |
| 33 | ND | ND | ND | ND | ND | ND |
| 34a | 0.011 | ND | ND | 0.02 | 95* | ND |
| 34b | ND | ND | ND | ND | ND | ND |
| 34c | ND | ND | ND | ND | ND | ND |
| 35 | 25 | >6 | 45 | ND | ND | ND |

All data shown in Table 1 is either the value of one data point or the average of more than one data point.
ND—no data
*% inhibition is shown at 0.67 μM compound concentration.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. A compound of Formula I wherein:

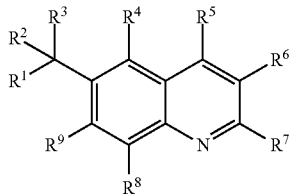

Formula I $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, quinazolinyl, cinnolinyl, benzothiazolyl, indazolyl, tetrahydropyranyl, tetrahydrofuranyl, furanyl, phenyl, oxazolyl, isoxazolyl, thiophenyl, benzoxazolyl, benzimidazolyl, indolyl, thiadiazolyl, oxadiazolyl or quinolinyl; wherein said piperidinyl, pyridyl, pyridyl N-oxide, pyrimidinyl, pyridazyl, pyrazinyl, quinazolinyl, cinnolinyl, benzothiazolyl, indazolyl, imidazolyl, phenyl, thiophenyl, benzoxazolyl, benzimidazolyl, indolyl, quinolinyl, and pyrazolyl are optionally substituted with $C(O)C_{(1-4)}$alkyl, $C(O)NH_2$, $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C_{(1-4)}$alkyl, $CF_3$, $CH_2CF_3$, Cl, F, —CN, $OC_{(1-4)}$alkyl, $N(C_{(1-4)}$alkyl$)_2$, —$(CH_2)_3OCH_3$, $SC_{(1-4)}$alkyl, OH, $CO_2H$, $CO_2C_{(1-4)}$alkyl, $C(O)CF_3$, $SO_2CF_3$, $OCF_3$, $OCHF_2$, $SO_2CH_3$, $SO_2NH_2$, $SO_2NHC_{(1-2)}$alkyl, $SO_2N(C_{(1-2)}$alkyl$)_2$, $C(O)NHSO_2CH_3$, or $OCH_2OCH_3$; and optionally substituted with up to two additional substituents independently selected from the group consisting of Cl, $C_{(1-2)}$alkyl, $SCH_3$, $OC_{(1-2)}$alkyl, $CF_3$, —CN, and F; and wherein said triazolyl, oxazolyl, isoxazolyl, pyrrolyl, and thiazolyl are optionally substituted with two substituents independently selected from the group consisting of $SO_2CH_3$, $SO_2NH_2$, $C(O)NH_2$, —CN, $OC_{(1-2)}$alkyl, $(CH_2)_{(2-3)}OCH_3$, $SCH_3$, $CF_3$, F, Cl, and $C_{(1-2)}$alkyl; and said thiadiazolyl and oxadiazolyl are optionally substituted with $C_{(1-2)}$alkyl; and said pyridyl, pyridyl-N-oxide, pyrimidinyl, pyridazyl, and pyrazinyl are optionally substituted with up to three additional substituents independently selected from the group consisting of $C(O)NHC_{(1-2)}$alkyl, $C(O)N(C_{(1-2)}$alkyl$)_2$, $NHC(O)C_{(1-4)}$alkyl, $NHSO_2C_{(1-4)}$alkyl, $C(O)CF_3$, $SO_2CF_3$, $SO_2NHC_{(1-2)}$alkyl, $SO_2N(C_{(1-2)}$alkyl$)_2$, $C(O)NHSO_2CH_3$, $SO_2CH_3$, $SO_2NH_2$, $C(O)NH_2$, —CN, $OC_{(1-4)}$alkyl, $(CH_2)_{(2-3)}OCH_3$, $SC_{(1-4)}$alkyl, $CF_3$, F, Cl, and $C_{(1-4)}$alkyl; and wherein said azetidinyl is optionally substituted with $CH_3$, $C(O)NH_2$, $CO_2C(CH_3)_3$, $SO_2CH_3$, or $C(O)CH_3$;

$R^2$ is H;

$R^3$ OH, $OCH_3$, or $NH_2$;

$R^4$ is H, or F;

$R^5$ is H, Cl, —CN, $CF_3$, $SC_{(1-4)}$alkyl, $OC_{(1-4)}$alkyl, OH, $C_{(1-4)}$alkyl, $N(CH_3)OCH_3$, $NH(C_{(1-4)}$alkyl), $N(C_{(1-4)}$alkyl$)_2$, 4-hydroxy-piperidinyl, azetidin-1-yl, or fur-2-yl; provided that $R^5$ may not be H if $R^7$ is also H;

$R^6$ is pyridyl, pyrimidinyl, pyridazyl, pyrazinyl, thiazolyl, isothiazolyl, furanyl, thiophenyl, oxazolyl, isoxazolyl, imidazolyl, pyrazolyl, pyrrolyl, triazolyl, oxadiazolyl, thiadiazolyl, or phenyl, any of which is optionally substituted with up to two substituents independently selected from the group consisting of piperidinyl, pyrrolidinyl, azetidinyl, pyrazolyl, triazolyl, imidazolyl, —CN, $C_{(1-4)}$alkyl, $OC_{(1-4)}$alkyl, $C(O)C_{(1-4)}$alkyl, $CO_2H$, $CO_2C_{(1-4)}$alkyl, $NH_2$, $NHC_{(1-2)}$alkyl, $N(C_{(1-2)}$alkyl$)_2$, $SO_2NH_2$, $SONH_2$, $SO_2NHC_{(1-2)}$alkyl, $SON(CH_3)_2$, $SO_2N(C_{(1-2)}$alkyl$)_2$, $SCH_3$, $OCH_2CF_3$, $SO_2CH_3$, $CF_3$, Cl, F, OH, and $OCF_3$; or $R^6$ is —O-phenyl, —NHphenyl, —$N(C_{(1-3)}$alkyl)phenyl, —$N(CO_2C(CH_3)_3)$phenyl, $N(COCH_3)$phenyl, —O-pyridyl, —NHpyridyl, —$N(C_{(1-3)}$alkyl)pyridyl, $N(CO_2C(CH_3)_3)$pyridyl, $N(COCH_3)$pyridyl, —O-pyrimidinyl, —NHpyrimidinyl, —$N(C_{(1-3)}$alkyl)pyrimidinyl, $N(CO_2C(CH_3)_3)$pyrimidinyl, $N(COCH_3)$pyrimidinyl, —O-pyridazyl, —NHpyridazyl, —$N(C_{(1-3)}$alkyl)pyridazyl, $N(CO_2C(CH_3)_3)$pyridazyl, $N(COCH_3)$pyridazyl, —O-pyrazinyl, —NHpyrazinyl, —$N(C_{(1-3)}$alkyl)pyrazinyl, $N(CO_2C(CH_3)_3)$pyrazinyl, or $N(COCH_3)$pyrazinyl; wherein said pyrimidinyl, pyridazyl, or pyrazinyl portions thereof are optionally substituted with Cl, F, $CH_3$, $SCH_3$, $OC_{(1-4)}$alkyl, —CN, $CONH_2$, $SO_2NH_2$, or $SO_2CH_3$; and wherein said phenyl portions thereof or said pyridyl portions thereof are optionally substituted with up to two substituents independently selected from the group consisting of $OCF_3$, $OCHF_2$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally substituted with $CH_3$; or $R^6$ is —$CH_2R^{6'}$, wherein $R^{6'}$ is pyridyl, phenyl, benzothiophenyl, thiophenyl, pyrimidinyl, pyridazyl, or pyrazinyl; wherein said pyrimidinyl, pyridazyl, or pyrazinyl are optionally substituted with Cl, F, $CH_3$, $SCH_3$, $OC_{(1-4)}$alkyl, —CN, $CONH_2$, $SO_2NH_2$, or $SO_2CH_3$; and wherein said pyridyl or phenyl is optionally substituted with up to two substituents independently selected from the group consisting of $OCF_3$, $SO_2C_{(1-4)}$alkyl, $CF_3$, $CHF_2$, pyrazolyl, triazolyl, imidazolyl, tetrazolyl, oxazolyl, thiazolyl, $C_{(1-4)}$alkyl, $C_{(3-4)}$cycloalkyl, $OC_{(1-4)}$alkyl, $N(CH_3)_2$, $SO_2NH_2$, $SO_2NHCH_3$, $SO_2N(CH_3)_2$, $CONH_2$, $CONHCH_3$, $CON(CH_3)_2$, Cl, F, —CN, $CO_2H$, OH, $CH_2OH$, $NHCOC_{(1-2)}$alkyl, $COC_{(1-2)}$alkyl, $SCH_3$, $CO_2C_{(1-4)}$alkyl, $NH_2$, $NHC_{(1-2)}$alkyl, and $OCH_2CF_3$; and wherein said pyrazolyl, triazolyl, imidazolyl, tetrazolyl, oxazolyl, and thiazolyl are optionally substituted with $CH_3$;

$R^7$ is H, Cl, —CN, $C_{(1-4)}$alkyl, $OC_{(1-4)}$alkylCF_3$, $OCF_3$, $OCHF_2$, $OCH_2CH_2OC_{(1-4)}$alkyl, $CF_3$, $SCH_3$, $C_{(1-4)}$alkyl$NA^1A^2$, $CH_2OC_{(2-3)}$alkyl$NA^1A^2$, $NA^1A^2$, $C(O)NA^1A^2$, $CH_2NHC_{(2-3)}$alkyl$NA^1A^2$, $CH_2N(CH_3)C_{(2-3)}$alkyl$NA^1A^2$, $NHC_{(2-3)}$alkyl$NA^1A^2$, $N(CH_3)C_{(2-4)}$alkyl$NA^1A^2$, $OC_{(2-4)}$alkyl$NA^1A^2$, $OC_{(1-4)}$alkyl, $OCH_2$-(1-methyl)-imidazol-2-yl, phenyl, thiophenyl, furyl, pyrazolyl, imidazolyl, pyridyl, pyridazyl, pyrazinyl, pyrimidinyl, indazolyl, phenyl, or

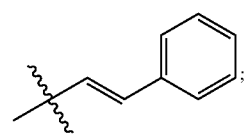 [SMILES: */C=C/c1ccccc1]

wherein said phenyl, thiophenyl, furyl, pyrazolyl, imidazolyl, pyridyl, pyridazyl, pyrazinyl, pyrimidinyl, and indazolyl are optionally substituted with up to three substituents independently selected from the group consisting of F, Cl, $CH_3$, $CF_3$, and $OCH_3$;

$A^1$ is H or $C_{(1-4)}$alkyl;

$A^2$ is H, $C_{(1-4)}$alkyl, $C_{(1-4)}$alkyl$OC_{(1-4)}$alkyl, $C_{(1-4)}$alkylOH, $C(O)C_{(1-4)}$alkyl, or $OC_{(1-4)}$alkyl; or $A^1$ and $A^2$ may be taken together with their attached nitrogen to form a ring selected from the group consisting of:

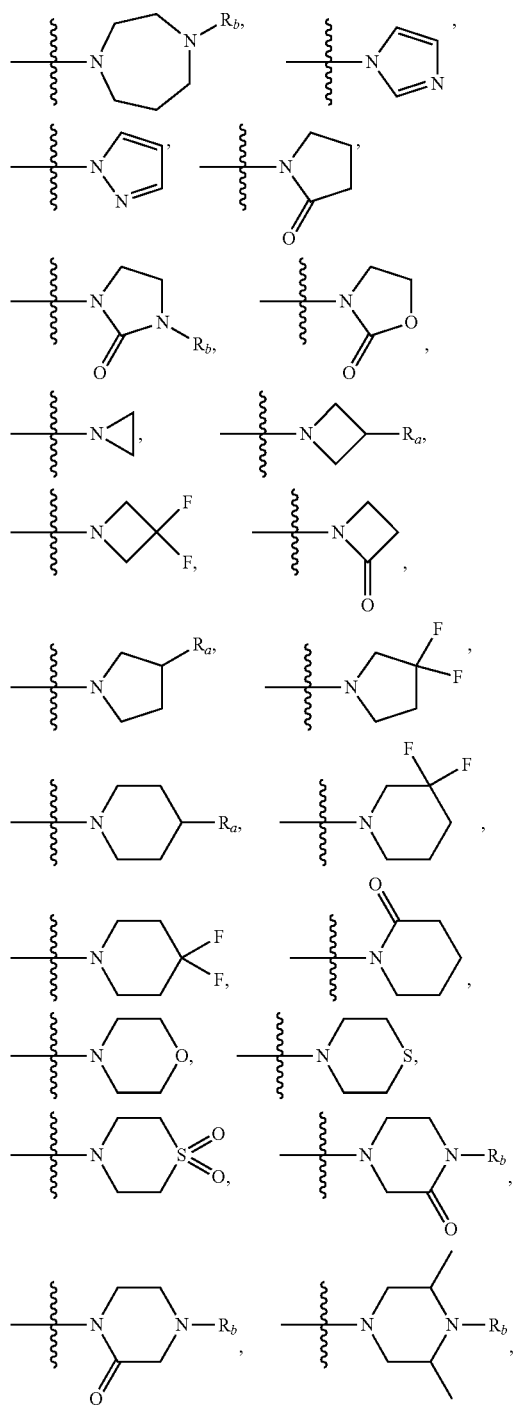

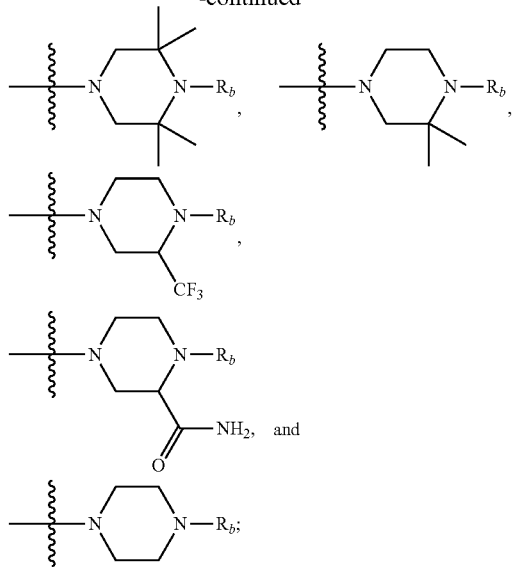

$R_a$ is H, $OC_{(1-4)}$alkyl, $CH_2OH$, $NH(CH_3)$, $N(CH_3)_2$, $NH_2$, $CH_3$, F, $CF_3$, $SO_2CH_3$, or OH;

$R_b$ is H, $CO_2C(CH_3)_3$, $C_{(1-4)}$alkyl, $C(O)C_{(1-4)}$alkyl, $SO_2C_{(1-4)}$alkyl, $CH_2CH_2CF_3$, $CH_2CF_3$, $CH_2$-cyclopropyl, phenyl, $CH_2$-phenyl, or $C_{(3-6)}$cycloalkyl;

$R^8$ is H, $C_{(1-3)}$alkyl, $OC_{(1-3)}$alkyl, $CF_3$, $NH_2$, $NHCH_3$, —CN, or F;

$R^9$ is H, or F;

and pharmaceutically acceptable salts thereof;

provided that azetidin-3-yl(4-chloro-2-methoxy-3-(4-(trifluoromethyl)benzyl)quinolin-6-yl)methanol, and tert-butyl 4-((4-chloro-2-methoxy-3-(4-(trifluoromethyl)benzyl) quinolin-6-yl)(hydroxy)methyl)piperidine-1-carboxylate are excluded from the claim.

2. A compound of claim 1 wherein:

$R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $C(O)CH_3$, $C(O)NH_2$, $C_{(1-2)}$alkyl, $CF_3$, Cl, F, —CN, $OCH_3$, $N(CH_3)_2$, —$(CH_2)_3OCH_3$, $SCH_3$, OH, $CO_2H$, $CO_2C_{(1-4)}$alkyl, $SO_2CH_3$, or $OCH_2OCH_3$; and optionally substituted with up to two additional substituents independently selected from the group consisting of Cl, $CH_3$, and $OCH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $SO_2CH_3$, or $C(O)CH_3$;

$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, 4-hydroxy-piperidinyl, azetidin-1-yl, or fur-2-yl;

$R^6$ is pyridyl or phenyl, either of which is optionally substituted with Cl, F, $CF_3$, $SO_2CH_3$, —CN, or $OCF_3$; or $R^6$ is —O-phenyl, —NHphenyl, —N($C_{(i-3)}$alkyl)phenyl, —N($CO_2C(CH_3)_3$)phenyl, —O-pyridyl, —NHpyridyl, —N($C_{(1-3)}$alkyl)pyridyl, or —N($CO_2C(CH_3)_3$)pyridyl wherein said phenyl portions thereof or said pyridyl portions thereof are optionally substituted with $OCF_3$, $SO_2CH_3$, $CF_3$, $CHF_2$, imidazol-1-yl, pyrazol-1-yl, 1,2, 4-triazol-1-yl, CH$_3$, OCH$_3$, Cl, F, or —CN; or R$^6$ is —CH$_2$R$^{6'}$, wherein R$^{6'}$ is pyridyl, phenyl, benzothiophenyl, or thiophenyl; wherein said pyridyl or phenyl is optionally substituted with OCF$_3$, SO$_2$CH$_3$, CF$_3$, CHF$_2$, imidazol-1-yl, pyrazol-1-yl, 1,2,4-triazol-1-yl, CH$_3$, OCH$_3$, Cl, F, or —CN;

R$^7$ is H, Cl, —CN, C$_{(1-4)}$alkyl, OCH$_2$CF$_3$, OCH$_2$CH$_2$OCH$_3$, CF$_3$, SCH$_3$, NA$^1$A$^2$, C(O)NHCH$_3$, N(CH$_3$)CH$_2$CH$_2$NA$^1$A$^2$, OCH$_2$CH$_2$NA$^1$A$^2$, OC$_{(1-3)}$alkyl, OCH$_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

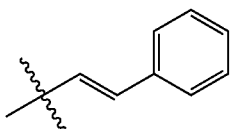 [SMILES: */C=C/c1ccccc1]

wherein said imidazolyl or pyrazolyl can be optionally substituted with a CH$_3$ group;

A$^1$ is H or C$_{(1-4)}$alkyl;

A$^2$ is H, C$_{(1-4)}$alkyl, C$_{(1-4)}$alkylOC$_{(1-4)}$alkyl, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

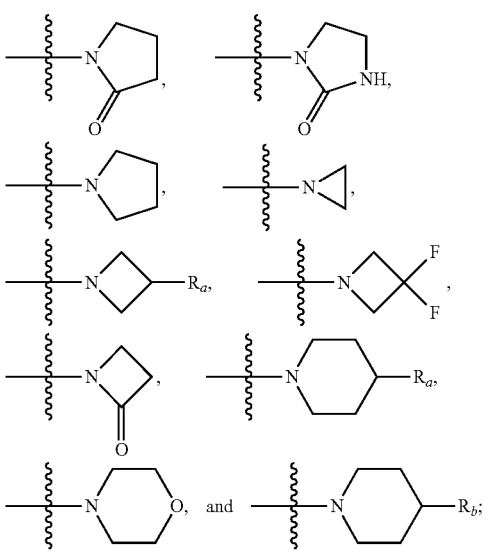

R$_a$ is H, F, OCH$_3$, or OH;
R$_b$ is CH$_3$, or phenyl;
R$^8$ is H, CH$_3$, OCH$_3$, or F;
and pharmaceutically acceptable salts thereof.

3. A compound of claim 2 wherein:

R$^1$ is azetidinyl, pyrazolyl, imidazolyl, triazolyl, thiazolyl, pyridyl, pyrimidinyl, piperidinyl, phenyl, isoxazolyl, or oxazolyl; wherein said piperidinyl, pyridyl, imidazolyl, phenyl, and pyrazolyl are optionally substituted with C(O)CH$_3$, C(O)NH$_2$, C$_{(1-2)}$alkyl, CF$_3$, Cl, —CN, or OCH$_3$; and optionally substituted with up to two additional CH$_3$ groups; and wherein said triazolyl, oxazolyl, and isoxazolyl, are optionally substituted with one or two CH$_3$ groups; and wherein said azetidinyl is optionally substituted with CO$_2$C(CH$_3$)$_3$;

R$^3$ is OH;

R$^5$ is H, —CN, CF$_3$, CH$_3$, Cl, OC$_{(1-2)}$alkyl, OH, C$_{(1-4)}$alkyl, NH(CH$_3$),N(C$_{(1-2)}$alkyl)$_2$, or 4-hydroxy-piperidinyl;

R$^6$ is phenyl, or pyridyl; wherein said phenyl or said pyridyl is optionally substituted with Cl, OCF$_3$, F, or —CN; or R$^6$ is —O-phenyl, —NHphenyl, —N(C$_{(1-3)}$alkyl)phenyl, or —N(CO$_2$C(CH$_3$)$_3$)phenyl; wherein said phenyl portion thereof is optionally substituted with Cl, F, or —CN; or R$^6$ is —CH$_2$R$^{6'}$, wherein R$^{6'}$ is pyridyl, or phenyl, wherein said phenyl is optionally substituted with pyrazol-1-yl, 1,2,4-triazol-1-yl, OCH$_3$, SO$_2$CH$_3$, Cl, F, CF$_3$, or —CN; and wherein said pyridyl is optionally substituted with CF$_3$;

R$^7$ is Cl, NA$^1$A$^2$, —CN, C$_{(1-2)}$alkyl, OC$_{(1-2)}$alkyl, CONHCH$_3$, or CF$_3$;

A$^1$ is C$_{(1-2)}$alkyl;

A$^2$ is C$_{(1-4)}$alkyl, CH$_2$CH$_2$OCH$_3$, C$_{(1-4)}$alkylOH, C(O)C$_{(1-2)}$alkyl, or OCH$_3$; or A$^1$ and A$^2$ may be taken together with their attached nitrogen to form a ring selected from the group consisting of:

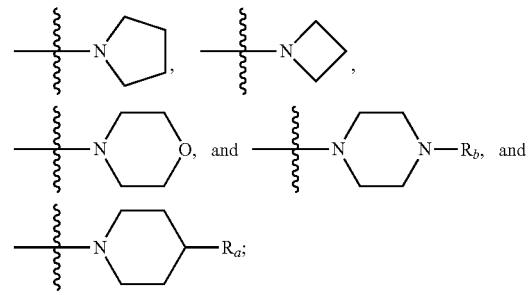

R$_a$ is OCH$_3$, or OH;
R$_b$ is CH$_3$, or phenyl;
and pharmaceutically acceptable salts thereof.

4. A compound of claim 3, wherein

R$^1$ is N-Boc-azetidin-3-yl, 1,3,5-trimethyl-pyrazol-4-yl, 1-methyl-imidazol-5-yl, 1,2-dimethyl-imidazol-5-yl, 1-methyl-1,2,3-triazol-5-yl, pyrid-4-yl, 2,6-dimethyl-pyrid-3-yl, N-acetyl-piperidin-4-yl, phenyl, 3,5-dimethyl-isoxazol-4-yl, 3-methyl-isoxazol-5-yl, or 2,4-dimethyl-oxazol-5-yl; wherein said phenyl is optionally substituted with Cl, or CN;

R$^4$ is H;

R$^5$ is H, or Cl;

R$^6$ is phenyl, wherein said phenyl is optionally substituted with Cl; or R$^6$ is —CH$_2$R$^{6'}$, wherein R$^{6'}$ is pyridyl, or phenyl, wherein said phenyl is optionally substituted with pyrazol-1-yl, SO$_2$CH$_3$, F, CF$_3$, or —CN; and wherein said pyridyl is optionally substituted with CF$_3$;

R$^7$ is Cl, azetidin-1-yl, CH$_2$CH$_3$, or OCH$_3$;

R$^8$ is H, or CH$_3$;

R$^9$ is H;

and pharmaceutically acceptable salts thereof.

5. A compound of claim 1 selected from the group consisting of:

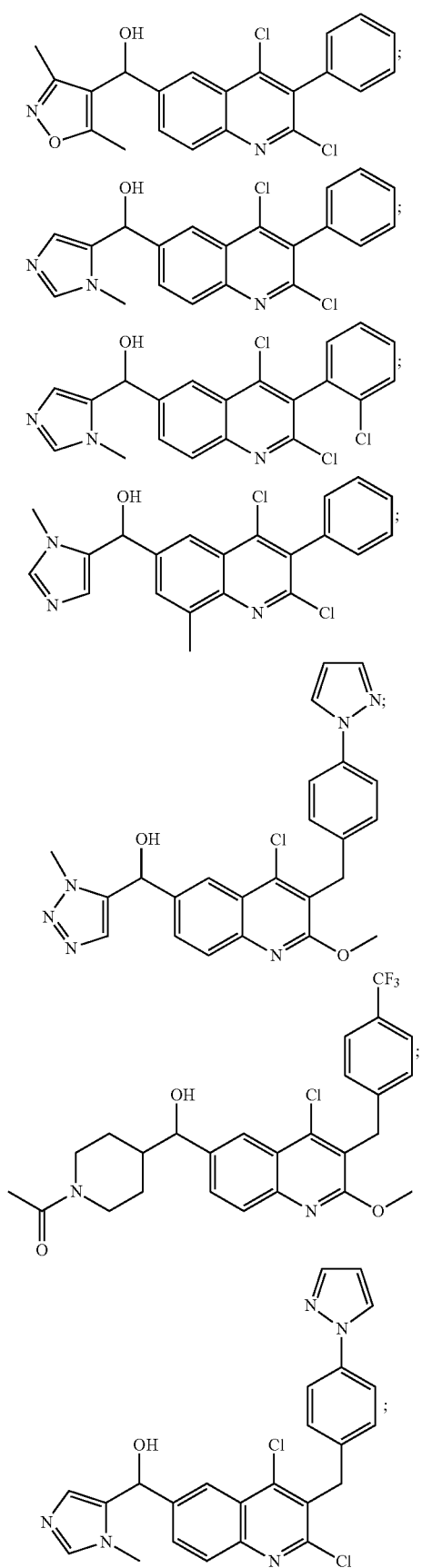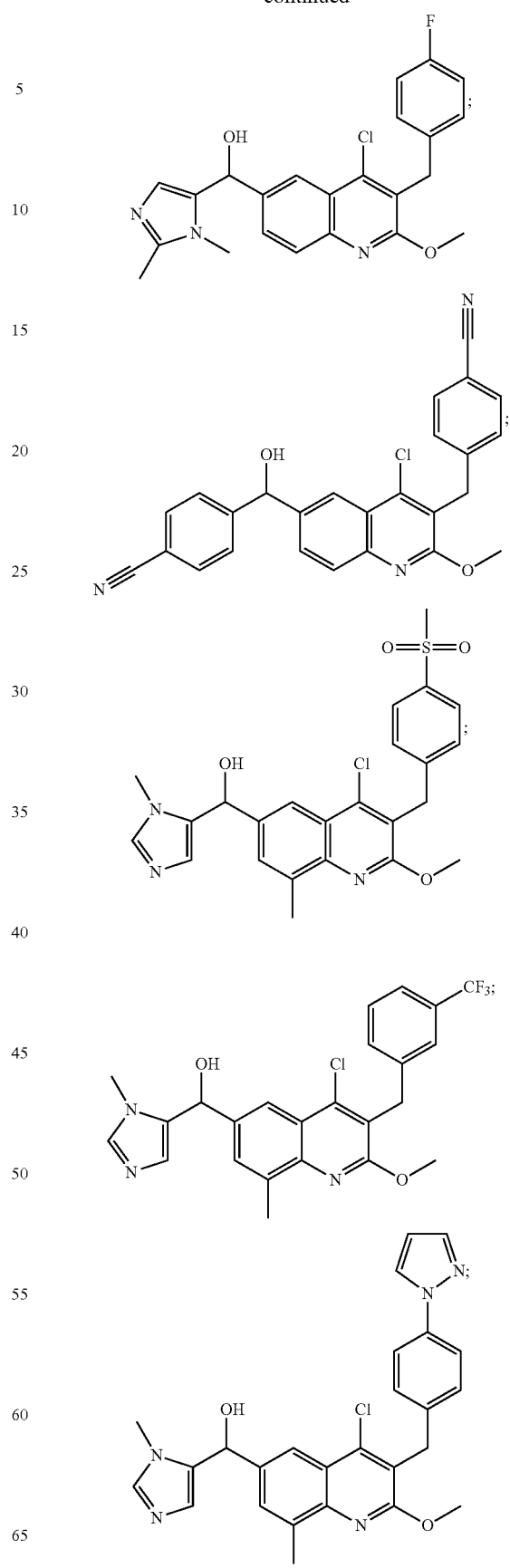

127
-continued
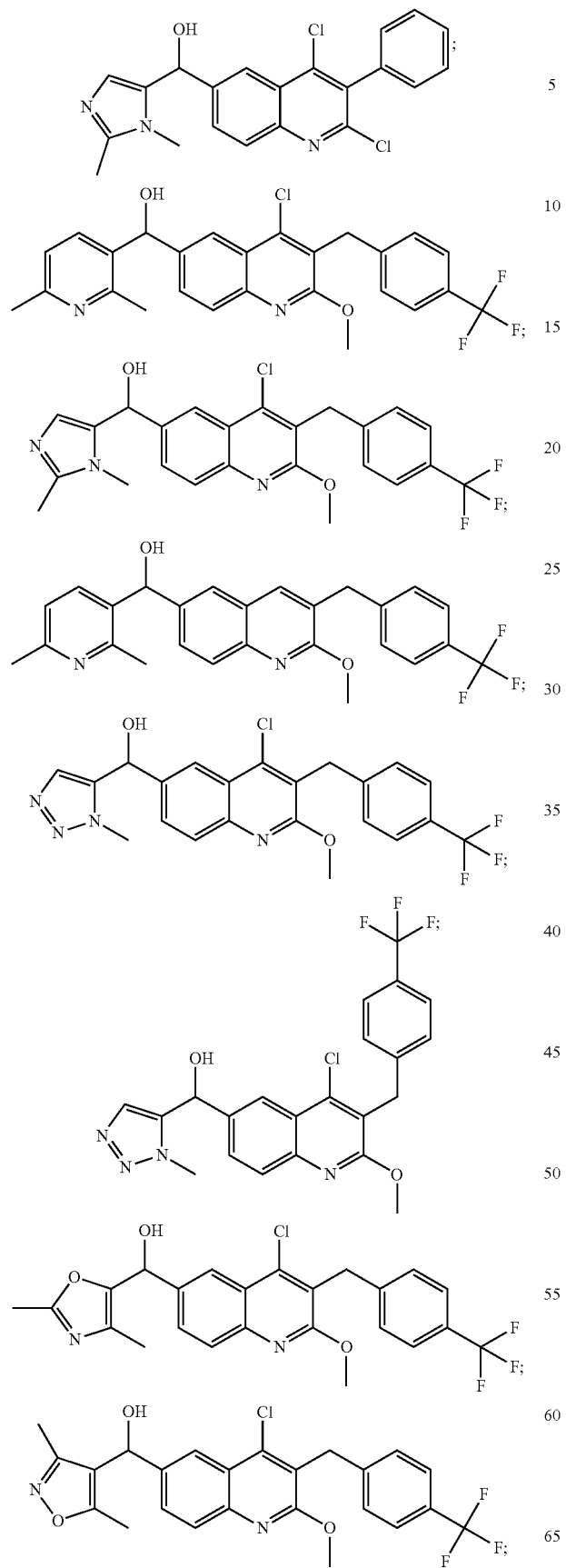
128
-continued
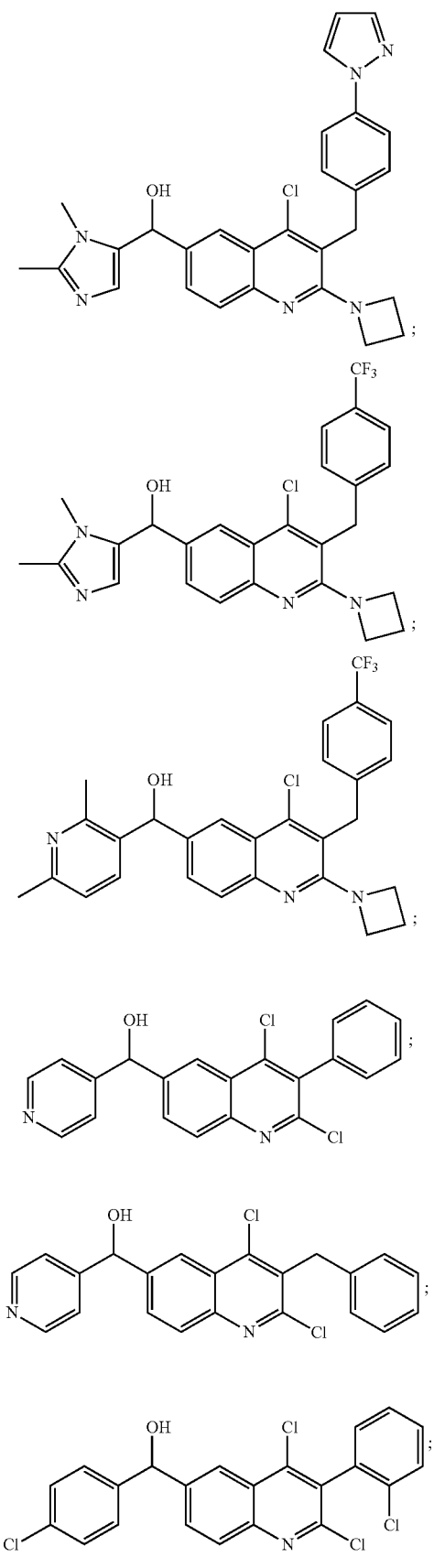

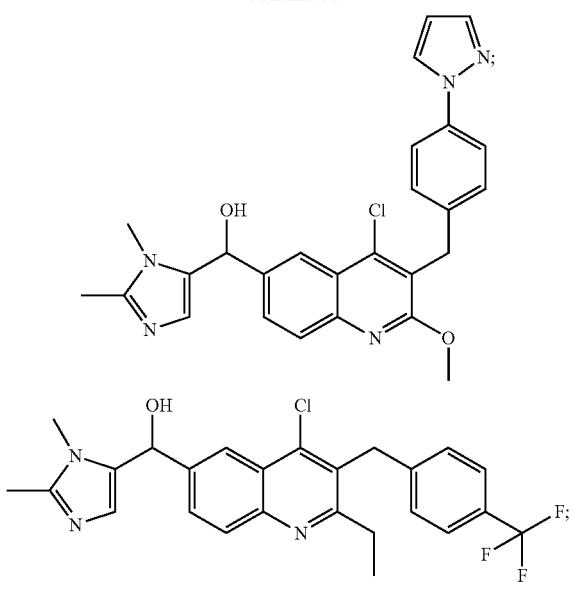
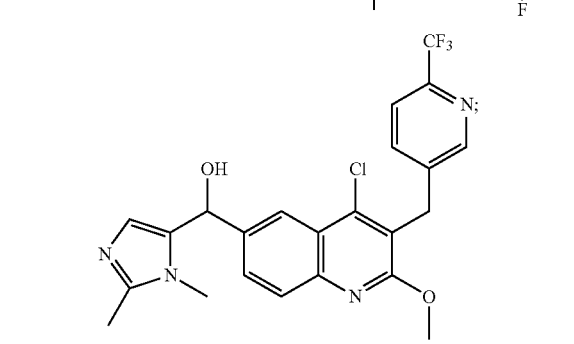
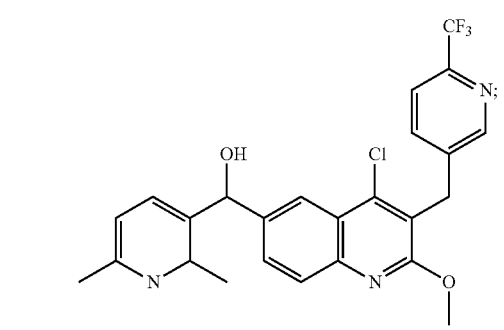
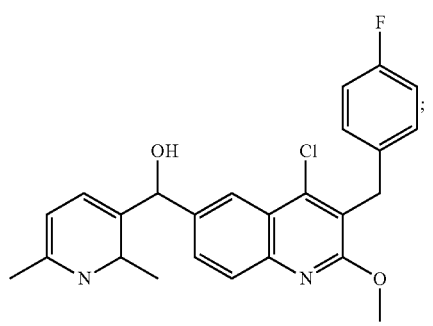
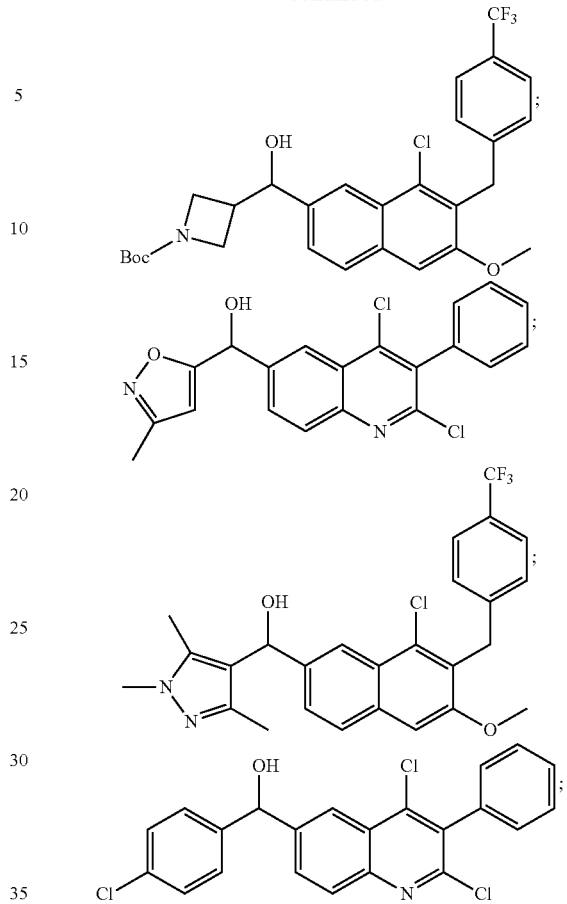

and pharmaceutically acceptable salts thereof.

6. A pharmaceutical composition, comprising a compound of claim 1 and a pharmaceutically acceptable carrier.

7. A pharmaceutical composition made by mixing a compound of claim 1 and a pharmaceutically acceptable carrier.

8. A process for making a pharmaceutical composition comprising mixing a compound of claim 1 and a pharmaceutically acceptable carrier.

9. A method for treating or ameliorating a RORγt mediated inflammatory syndrome, disorder or disease comprising administering to a subject in need thereof an effective amount of a compound of claim 1, wherein the disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus.

10. The method of claim 9, wherein the disease is psoriasis.

11. The method of claim 9, wherein the disease is rheumatoid arthritis.

12. The method of claim 9, wherein the inflammatory bowel disease is ulcerative colitis.

13. The method of claim 9, wherein the inflammatory bowel disease is Crohn's disease.

14. The method of claim 9, wherein the disease is multiple sclerosis.

15. The method of claim 9, wherein the disease is neutrophilic asthma.

16. The method of claim 9, wherein the disease is steroid resistant asthma.

17. The method of claim 9, wherein the disease is psoriatic arthritis.

18. The method of claim 9, wherein the disease is ankylosing spondylitis.

19. The method of claim 9, wherein the disease is systemic lupus erythematosus.

20. The method of claim 9, wherein the disease is chronic obstructive pulmonary disorder.

21. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis, and psoriasis.

22. A method for treating or ameliorating a RORγt mediated inflammatory syndrome, disorder or disease comprising administering to a subject in need thereof an effective amount of a compound of claim 5, wherein the disease is selected from the group consisting of: rheumatoid arthritis and psoriasis.

23. A method of inhibiting production of interleukin-17, comprising administering to a subject in need thereof an effective amount of a compound of claim 1.

\* \* \* \* \*

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180

```
ggggacaagt cgtctgggat ccactacggg gttatcacct gtgaggggtg caagggcttc      240
ttccgccgga gccagcgctg taacgcggcc tactcctgca cccgtcagca gaactgcccc      300
atcgaccgca ccagccgaaa ccgatgccag cactgccgcc tgcagaaatg cctggcgctg      360
ggcatgtccc gagatgctgt caagttcggc cgcatgtcca agaagcagag ggacagcctg      420
catgcagaag tgcagaaaca gctgcagcag cggcaacagc agcaacagga accagtggtc      480
aagacccctc cagcagggc ccaaggagca gataccctca cctacacctt ggggctccca       540
gacgggcagc tgcccctggg ctcctcgcct gacctgcctg aggcttctgc ctgtccccct      600
ggcctcctga agcctcagg ctctgggccc tcatattcca caacttggc caaggcaggg        660 ctcaatgggg cctcatgcca ccttgaatac agccctgagc ggggcaaggc tgagggcaga      720
gagagcttct atagcacagg cagccagctg acccctgacc gatgtggact tcgtttttgag     780 gaacacaggc atcctgggct tggggaactg ggacagggcc cagacagcta cggcagcccc     840
agtttccgca gcacaccgga ggcacctat gcctccctga cagagataga gcacctggtg       900
cagagcgtct gcaagtccta cagggagaca tgccagctgc ggctggagga cctgctgcgg     960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt ttgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agccttgtt ctcatcaatg cccatcggcc agggctccaa      1380
gagaaaagga agtagaaca gctgcagtac aatctggagc tggcctttca tcatcatctc     1440
tgcaagactc atcgccaaag catcctggca aagctgccac ccaaggggaa gcttcggagc    1500
ctgtgtagcc agcatgtgga aaggctgcag atcttccagc acctccaccc catcgtggtc    1560
caagccgctt tccctccact ctacaaggag ctcttcagca ctgaaaccga gtcacctgtg    1620
gggctgtcca agtgacctgg aagagggact ccttgcctct ccctatgcc tgctggccca    1680 cctccctgga ccccgttcca ccctcaccct tttcctttcc catgaaccct ggagggtggt   1740
ccccaccagc tctttggaag tgagcagatg ctgcggctgg ctttctgtca gcaggccggc    1800
ctggcagtgg gacaatcgcc agagggtggg gctggcagaa caccatctcc agcctcagct    1860
ttgacctgtc tcatttccca tattccttca cacccagctt ctggaaggca tggggtggct    1920
gggatttaag gacttctggg ggaccaagac atcctcaaga aaacaggggc atccagggct    1980
ccctggatga atagaatgca attcattcag aagctcagaa gctaagaata agcctttgaa    2040
atacctcatt gcatttccct ttgggcttcg gcttgggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctggggtct    2220
aaccaaaaat ggatgggatg aggatgagag gctggagata attgttttat gggatttggg    2280
tgtgggacta gggtacaatg aaggccaaga gcatctcaga catagagtta aaactcaaac    2340 ctccttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
```

```
cagggaaag   tcccaatcct   gagggaccct   cccaaacatt   tccatggtgc   tccagtccac   2580
tgatcttggg   tctggggtga   tccaaatacc   accccagctc   cagctgtctt   ctaccactag   2640
aagacccaag   agaagcagaa   gtcgctcgca   ctggtcagtc   ggaaggcaag   atcagatcct   2700
ggaggacttt   cctggcctgc   ccgccagccc   tgctcttgtt   gtggagaagg   aagcagatgt   2760
gatcacatca   ccccgtcatt   gggcaccgct   gactccagca   tggaggacac   cagggagcag   2820
ggcctgggcc   tgtttcccca   gctgtgatct   tgcccagaac   ctctcttggc   ttcataaaca   2880
gctgtgaacc   ctcccctgag   ggattaacag   caatgatggg   cagtcgtgga   gttgggggggg   2940 ttggggggtgg   gattgtgtcc   tctaagggga   cgggttcatc   tgagtaaaca   taaaccccaa   3000
cttgtgccat   tctttataaa   atgattttaa   aggcaaaaaa   aaaaaaaaaa   aaaa   3054

<210> SEQ ID NO 2
<211> LENGTH: 786
<212> TYPE: DNA
<213> ORGANISM: Homo sapiens

<400> SEQUENCE: 2
agcacaccgg   aggcacccta   tgcctccctg   acagagatag   agcacctggt   gcagagcgtc   60
tgcaagtcct   acagggagac   atgccagctg   cggctggagg   acctgctgcg   gcagcgctcc   120
aacatcttct   cccgggagga   agtgactggc   taccagagga   agtccatgtg   ggagatgtgg   180
gaacggtgtg   cccaccacct   caccgaggcc   attcagtacg   tggtggagtt   cgccaagagg   240
ctctcaggct   ttatggagct   ctgccagaat   gaccagattg   tgcttctcaa   agcaggagca   300
atggaagtgg   tgctggttag   gatgtgccgg   gcctacaatg   ctgacaaccg   cacggtcttt   360
tttgaaggca   aatacggtgg   catggagctg   ttccgagcct   gggctgcag   cgagctcatc   420 agctccatct   ttgacttctc   ccactcccta   agtgccttgc   acttttccga   ggatgagatt   480
gccctctaca   cagcccttgt   tctcatcaat   gcccatcggc   cagggctcca   agagaaaagg   540
aaagtagaac   agctgcagta   caatctggag   ctggcctttc   atcatcatct   ctgcaagact   600
catcgccaaa   gcatcctggc   aaagctgcca   cccaagggga   agcttcggag   cctgtgtagc   660
cagcatgtgg   aaaggctgca   gatcttccag   cacctccacc   ccatcgtggt   ccaagccgct   720
ttccctccac   tctacaagga   gctcttcagc   actgaaaccg   agtcacctgt   ggggctgtcc   780
aagtga   786

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His His Ala Gly Gly Ala Glu Asn Leu Tyr
1               5                   10                  15
```

-continued

Phe Gln Gly Ala Met Asp Ser Thr Pro Glu Ala Pro Tyr Ala Ser Leu
                20                  25                  30

Thr Glu Ile Glu His Leu Val Gln Ser Val Cys Lys Ser Tyr Arg Glu
            35                  40                  45

Thr Cys Gln Leu Arg Leu Glu Asp Leu Leu Arg Gln Arg Ser Asn Ile
50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
                100                 105                 110

Asp Gln Ile Val Leu Leu Lys Ala Gly Ala Met Glu Val Val Leu Val
                115                 120                 125

Arg Met Cys Arg Ala Tyr Asn Ala Asp Asn Arg Thr Val Phe Phe Glu
130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
                180                 185                 190

Ala His Arg Pro Gly Leu Gln Glu Lys Arg Lys Val Glu Gln Leu Gln
                195                 200                 205

Tyr Asn Leu Glu Leu Ala Phe His His His Leu Cys Lys Thr His Arg
                210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
                260                 265                 270

Thr Glu Thr Glu Ser Pro Val Gly Leu Ser Lys
                275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain

<400> SEQUENCE: 6

Leu Phe Lys Glu Leu Phe
1               5

<210> SEQ ID NO 7
<211> LENGTH: 786

<212> TYPE: DNA
<213> ORGANISM: Artificial Sequence
<220> FEATURE:
<223> OTHER INFORMATION: LBD with mutated AF2 domain

<400> SEQUENCE: 7

```
agcacaccgg aggcacccta tgcctccctg acagagatag agcacctggt gcagagcgtc    60
tgcaagtcct acagggagac atgccagctg cggctggagg acctgctgcg cagcgctcc    120
aacatcttct cccggagga agtgactggc taccagagga gtccatgtg ggagatgtgg     180
gaacggtgtg cccaccacct caccgaggcc attcagtacg tggtggagtt cgccaagagg    240
ctctcaggct tatggagct ctgccagaat gaccagattg tgcttctcaa agcaggagca     300
atggaagtgg tgctggttag gatgtgccgg gcctacaatg ctgacaaccg cacggtcttt    360
tttgaaggca atacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaaggga agcttcggag cctgtgtagc    660
cagcatgtgg aaaggctgca gatcttccag cacctccacc ccatcgtggt ccaagccgct    720
ttccctccac tcttcaagga gctcttcagc actgaaaccg agtcacctgt ggggctgtcc    780
aagtga                                                                786
```

<210> SEQ ID NO 8
<211> LENGTH: 261
<212> TYPE: PRT
<213> ORGANISM: Homo sapiens

<400> SEQUENCE: 8

```
Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190
```

```
Phe His His His Leu Cys Lys Thr His Arg Gln Ser Ile Leu Ala Lys
            195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
            260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
            20                  25                  30

Glu Asp Leu Leu Arg Gln Arg Ser Asn Ile Phe Ser Arg Glu Glu Val
        35                  40                  45

Thr Gly Tyr Gln Arg Lys Ser Met Trp Glu Met Trp Glu Arg Cys Ala
    50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
            180                 185                 190

Phe His His His Leu Cys Lys Thr His Arg Gln Ser Ile Leu Ala Lys
        195                 200                 205

Leu Pro Pro Lys Gly Lys Leu Arg Ser Leu Cys Ser Gln His Val Glu
    210                 215                 220

Arg Leu Gln Ile Phe Gln His Leu His Pro Ile Val Val Gln Ala Ala
225                 230                 235                 240

Phe Pro Pro Leu Phe Lys Glu Leu Phe Ser Thr Glu Thr Glu Ser Pro
                245                 250                 255

Val Gly Leu Ser Lys
            260
```